US009681948B2

(12) United States Patent
Levi et al.

(10) Patent No.: US 9,681,948 B2
(45) Date of Patent: Jun. 20, 2017

(54) HEART ANCHOR DEVICE

(75) Inventors: Tamir Levi, Doar-Na Hevel Megiddo (IL); Meir Rosenberg, Newton, MA (US); Ori Ben-Amotz, Caesarea (IL); Yoram Rozy, Caesarea (IL); Eyal Benbenisti, Hod-HaSharon (IL); Roey Shafrir, Modiln (IL); Doron Kopelman, Caesarea (IL); Itshak Cohen, Ramat-HaSharon (IL); Tamar Harel, Haifa (IL)

(73) Assignee: V-Wave Ltd., Caesarea (IL)

( * ) Notice: Subject to any disclaimer, the term of this patent is extended or adjusted under 35 U.S.C. 154(b) by 1285 days.

(21) Appl. No.: 12/223,080

(22) PCT Filed: Jan. 23, 2007

(86) PCT No.: PCT/IB2007/050234
§ 371 (c)(1),
(2), (4) Date: Jul. 16, 2014

(87) PCT Pub. No.: WO2007/083288
PCT Pub. Date: Jul. 26, 2007

(65) Prior Publication Data
US 2015/0039084 A1    Feb. 5, 2015

Related U.S. Application Data

(60) Provisional application No. 60/862,496, filed on Oct. 23, 2006, provisional application No. 60/777,315, (Continued)

(51) Int. Cl.
*A61F 2/06*  (2013.01)
*A61F 2/24*  (2006.01)
(Continued)

(52) U.S. Cl.
CPC ........ *A61F 2/2409* (2013.01); *A61B 17/0057* (2013.01); *A61B 2017/00004* (2013.01);
(Continued)

(58) Field of Classification Search
CPC .... A61F 2/2418; A61F 2/2409; A61F 2/2412; A61F 2220/0016; A61F 2230/0054
See application file for complete search history.

(56) References Cited

U.S. PATENT DOCUMENTS 3,874,388 A    4/1975    King et al.
4,601,309 A    7/1986    Chang
(Continued)

FOREIGN PATENT DOCUMENTS

FR        2827153       1/2003
WO    WO-99/60941 A1   12/1999
(Continued)

OTHER PUBLICATIONS

International Preliminary Report on Patentability Dated Aug. 7, 2008 From the International Bureau of WIPO Re.: Application No. PCT/IB2007/050234.
(Continued)

*Primary Examiner* — Thomas J Sweet
*Assistant Examiner* — Tiffany Shipmon
(74) *Attorney, Agent, or Firm* — Foley & Lardner LLP; Christopher C. Bolten; Nicola A. Pisano

(57) ABSTRACT

A medical implant including an anchor portion including a plurality of arms adapted to engage an internal tissue wall of a body from two opposite faces, wherein the anchor portion is configured such that at least one of the arms does not have an entirely overlapping arm on the other side of the wall and an opening portion adapted to define an opening for blood flow through the internal tissue wall, when the anchor portion engages the wall.

39 Claims, 24 Drawing Sheets

Related U.S. Application Data filed on Feb. 28, 2006, provisional application No. 60/761,192, filed on Jan. 23, 2006.

(51) Int. Cl.
*A61B 17/00* (2006.01)
*A61B 17/06* (2006.01)

(52) U.S. Cl.
CPC ............ *A61B 2017/00017* (2013.01); *A61B 2017/00035* (2013.01); *A61B 2017/00084* (2013.01); *A61B 2017/00398* (2013.01); *A61B 2017/00411* (2013.01); *A61B 2017/00557* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61B 2017/00734* (2013.01); *A61B 2017/00862* (2013.01); *A61B 2017/061* (2013.01)

(56) References Cited

U.S. PATENT DOCUMENTS

| | | |
|---|---|---|
| 4,662,355 A | 5/1987 | Pieronne et al. |
| 4,705,507 A | 11/1987 | Boyles |
| 4,836,204 A | 6/1989 | Landymore et al. |
| 4,979,955 A | 12/1990 | Smith |
| 4,995,857 A | 2/1991 | Arnold |
| 5,186,431 A | 2/1993 | Tamari |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,556,386 A | 9/1996 | Todd |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,795,307 A | 8/1998 | Krueger |
| 5,810,836 A | 9/1998 | Hussein et al. |
| 5,824,071 A | 10/1998 | Nelson et al. |
| 5,916,193 A | 6/1999 | Stevens et al. |
| 5,941,850 A | 8/1999 | Shah et al. |
| 5,957,949 A | 9/1999 | Leonhardt et al. |
| 6,039,759 A | 3/2000 | Carpentier et al. |
| 6,120,534 A | 9/2000 | Ruiz |
| 6,126,686 A | 10/2000 | Badylak et al. |
| 6,165,188 A | 12/2000 | Saadat et al. |
| 6,210,318 B1 | 4/2001 | Lederman |
| 6,217,541 B1 | 4/2001 | Yu |
| 6,242,762 B1 | 6/2001 | Brown et al. |
| 6,254,564 B1 | 7/2001 | Wilk et al. |
| 6,260,552 B1 | 7/2001 | Mortier et al. |
| 6,270,526 B1 | 8/2001 | Cox |
| 6,277,078 B1 | 8/2001 | Porat et al. |
| 6,302,892 B1 | 10/2001 | Wilk |
| 6,328,699 B1 | 12/2001 | Eigler et al. |
| 6,344,022 B1 | 2/2002 | Jarvik |
| 6,358,277 B1 | 3/2002 | Duran |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,478,776 B1 | 11/2002 | Rosenman et al. |
| 6,491,705 B2 | 12/2002 | Gifford et al. |
| 6,527,698 B1 | 3/2003 | Kung et al. |
| 6,544,208 B2 | 4/2003 | Ethier et al. |
| 6,562,066 B1 | 5/2003 | Martin |
| 6,572,652 B2 | 6/2003 | Shaknovich |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 7,001,409 B2 | 2/2006 | Amplatz |
| 7,149,587 B2 | 12/2006 | Wardle et al. |
| 7,294,115 B1 | 11/2007 | Wilk |
| 7,794,473 B2 | 9/2010 | Tessmer et al. |
| 7,988,724 B2 | 8/2011 | Salahieh et al. |
| 8,016,877 B2 | 9/2011 | Seguin et al. |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,147,545 B2 | 4/2012 | Avior |
| 8,157,860 B2 | 4/2012 | McNamara et al. |
| 8,235,916 B2 | 8/2012 | Whiting et al. |
| 8,235,933 B2 | 8/2012 | Keren et al. |
| 8,246,677 B2 | 8/2012 | Ryan |
| 8,303,511 B2 | 11/2012 | Eigler et al. |
| 8,328,751 B2 | 12/2012 | Keren et al. |
| 8,348,996 B2 | 1/2013 | Tuval et al. |
| 8,398,708 B2 | 3/2013 | Meiri et al. |
| 8,460,366 B2 | 6/2013 | Rowe |
| 8,597,225 B2 | 12/2013 | Kapadia |
| 8,696,611 B2 | 4/2014 | Nitzan et al. |
| 9,034,034 B2 | 5/2015 | Nitzan et al. |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1* | 11/2002 | Keren ............ A61B 17/00234 604/9 |
| 2003/0100920 A1 | 5/2003 | Akin et al. |
| 2003/0125798 A1 | 7/2003 | Martin |
| 2003/0136417 A1* | 7/2003 | Fonseca ............ A61B 5/03 128/899 |
| 2003/0209835 A1 | 11/2003 | Chun et al. |
| 2003/0216679 A1 | 11/2003 | Wolf et al. |
| 2004/0010219 A1 | 1/2004 | McCusker et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0162514 A1 | 8/2004 | Alferness et al. |
| 2004/0193261 A1* | 9/2004 | Berreklouw ............ A61B 17/11 623/2.11 |
| 2004/0210190 A1 | 10/2004 | Kohler et al. |
| 2004/0210307 A1 | 10/2004 | Khairkhahan |
| 2005/0033351 A1 | 2/2005 | Newton |
| 2005/0065589 A1 | 3/2005 | Schneider et al. |
| 2005/0148925 A1 | 7/2005 | Rottenberg et al. |
| 2005/0165344 A1 | 7/2005 | Dobak, III |
| 2005/0182486 A1* | 8/2005 | Gabbay ............ A61F 2/2409 623/2.11 |
| 2005/0283231 A1 | 12/2005 | Haug et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122647 A1 | 6/2006 | Callaghan et al. |
| 2006/0167541 A1 | 7/2006 | Lattouf |
| 2006/0212110 A1 | 9/2006 | Osborne et al. |
| 2006/0282157 A1 | 12/2006 | Hill et al. |
| 2007/0010852 A1* | 1/2007 | Blaeser ............ A61B 17/0057 606/213 |
| 2007/0043435 A1 | 2/2007 | Seguin et al. |
| 2007/0213813 A1 | 9/2007 | Von Segesser et al. |

(56) References Cited

U.S. PATENT DOCUMENTS

| | | |
|---|---|---|
| 2007/0282157 A1 | 12/2007 | Rottenberg et al. |
| 2007/0299384 A1 | 12/2007 | Faul et al. |
| 2008/0086205 A1 | 4/2008 | Gordy et al. |
| 2008/0262602 A1 | 10/2008 | Wilk et al. |
| 2009/0054976 A1 | 2/2009 | Tuval et al. |
| 2009/0125104 A1 | 5/2009 | Hoffman |
| 2009/0276040 A1 | 11/2009 | Rowe et al. |
| 2010/0057192 A1 | 3/2010 | Celermajer |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0306916 A1 | 12/2011 | Nitzan et al. |
| 2012/0071918 A1 | 3/2012 | Amin et al. |
| 2012/0165928 A1 | 6/2012 | Nitzan et al. |
| 2012/0271398 A1 | 10/2012 | Essinger et al. |
| 2013/0030521 A1 | 1/2013 | Nitzan et al. |
| 2013/0197423 A1 | 8/2013 | Keren et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0213959 A1 | 7/2014 | Nitzan et al. |
| 2014/0350565 A1 | 11/2014 | Yacoby et al. |
| 2015/0245908 A1 | 9/2015 | Nitzan et al. |

FOREIGN PATENT DOCUMENTS

| | | | |
|---|---|---|---|
| WO | WO-2005/027752 A1 | 3/2005 | |
| WO | WO-2005/074367 A1 | 8/2005 | |
| WO | WO-2006/127765 A1 | 11/2006 | |
| WO | WO-2007/083288 A2 | 7/2007 | |
| WO | WO-2008/055301 A1 | 5/2008 | |
| WO | WO-2009/029261 A1 | 3/2009 | |
| WO | WO-2010/128501 A1 | 11/2010 | |

OTHER PUBLICATIONS

Ewert et al. "Masked Left Ventricular Restriction in Elderly Patients With Atrial Septal Defects: A Contraindication for Closure", Catherization and Cardiovascular Interventions, 52: 177-180, 2001.
Zhou et al. "Unidirectional Valve Patch for Repair of Cardiac Septal Defects With Pulmonary Hypertension", Annals of Thoracic Surgeons, 60: 1245-1249, 1995.
Ando et al., "Left vetricular decompression through a patent foramen ovale in a patient with hypertrophic cardiomyopathy: A case report," Cardiovascular Ultrasound, (2004), 2:1-7.
Article 34 Amendments dated Nov. 27, 2012, as filed in related Int'l PCT Application No. PCT/IS2011/000958.
Bristow et al., "Improvement in cardiac myocite function by biological effects of medical therapy: A new concept in the treatment of heart failure," European Heart Journal, (1995), 16(Suppl.F):20-31.
Case et al., "Relief of High Left-Atrial Pressure in Left-Ventricular Failure," Lancet, (Oct. 17, 1964), pp. 841-842.
Coats et al., "Controlled trial of physical training in chronic heart failure: Exercise preformance, hemodynamics, ventilation, and autonomic function," Circulation, (1992), 85:2119-2131.
Davies et al., "Reduced contraction and altered frequency response of isolated ventricular myocytes from patients with heart failure," Circulation, (1995), 92:2540-2549.
Ennezat et al., "An unusual case of low-flow, low gradient severe aortic stenosis: Left-to-right shunt due to atrial septal defect," Cardiology, (2009), 113(2):146-148.
Ewert et al., "Acute left heart failure after interventional occlusion of an atrial septal defect," Z. Kardiol., (May 2001), 90(5):362-366.
Ewert et al., "Masked left ventricular restriction in elderly patients with atrial septal defects: A contraindication for closure?" Catheterization and Cardiovascular Interventions, (2001), 52:177-180.
Geiran et al., "Changes in cardiac dynamics by opening an interventricular shunt in dogs," J. Surg. Res., (Jan. 1990), 48(1):6-12.
Gelernter-Yaniv et al., "Transcatheter closure of left-to-right interatrial shunts to resolve hypoxemia," Congenit. Heart Dis., (Jan. 2008), 31(1):47-53.
Gewillig et al., "Creation with a stent of an unrestrictive lasting atrial communication," Cardio. Young, (2002), 12(4):404-407.
International Search Report for PCT/IL2005/000131 dated Apr. 7, 2008, (3 pages).
International Search Report for PCT/IL2010/000354 dated Aug. 25, 2010 (1 pg).
Int'l Preliminary Report on Patentability dated Mar. 5, 2013, in related Int'l PCT Patent Appl No. PCT/IL2011/000958.
Kramer et al., "Controlled study of captopril in chronic heart failure: A rest and exercise hemodynamic study," Circulation, (1983), 67(4):807-816.
Lai et al., "Bidirectional shunt through a residual atrial septal defect after percutaneous transvenous mitral commissurotomy," Cardiology, (1993), 83(3):205-207.
Lemmer et al., "Surgical implications of atrial septal defect complicating aortic balloon valvuloplasty," Ann. thorac. Surg., (Aug. 1989), 48(2):295-297.
Merriam-Webster "Definition of 'Chamber'," OnLine Dictionary 2004, Abstract.
Schubert et al., "Left ventricular conditioning in the elderly patient to prevent congestive heart failure after transcatheter closure of the atrial septal defect," Catheter Cardiovasc. Interv., (2005), 64(3):333-337.
Stormer et al., "Comparative study of in vitro flow characteristics between a human aortic valve and a designed aortic and six corresponding types of prosthetic heart valves," European Surgical Research, (1976), 8(2):117-131.
Stumper et al., "Modified technique of stent fenestration of the atrial septum," Heart, (2003), 89:1227-1230.
Zhou et al., "Unidirectional valve patch for repair of cardiac septal defects with pulmonary hypertension," Annals of Thoracic Surgeons, (1995), 60:1245-1249.
Braunwald, Heart Disease, Chapter 6, p. 186.
Bridges, et al., The Society of Thoracic Surgeons Practice Guideline Series: Transmyocardial Laser Revascularization, Ann Thorac Surg., 77:1494-1502 (2004).
Roven et al., "Effect of Compromising Right Ventricular Function in Left Ventricular Failure by Means of Interatrial and Other Shunts," American Journal Cardiology, 24:209-219 (1969).
Salehian et al., Improvements in Cardiac Form and Function After Transcatheter Closure of Secundum Atrial Septal Defects, Journal of the American College of Cardiology, 45(4):499-504 (2005).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Schmitto et al., Chronic heart failure induced by multiple sequential coronary microembolization in sheep, The International Journal of Artificial Organs, 31(4):348-353 (2008).
Trainor et al., Comparative Pathology of an Implantable Left Atrial Pressure Sensor, ASAIO Journal, Clinical Cardiovascular/Cardiopulmonary Bypass, 59(5):486-92 (2013).

* cited by examiner

US 9,681,948 B2

HEART ANCHOR DEVICE

RELATED APPLICATIONS

This Application is a National Phase of PCT Patent Application No. PCT/IB2007/050234 having International filing date of Jan. 23, 2007, which claims the benefit under 35 USC 119(e) of US Provisional applications Nos. 60/862,496, filed on Oct. 23, 2006; 60/777,315, filed on Feb. 28, 2006 and 60/761,192, filed on Jan. 23, 2006, the disclosures of all of which are incorporated herein by reference in their entirety.

FIELD OF THE INVENTION

The present invention relates to heart implants for example to implants for the heart which can be delivered in a minimally invasive procedure.

BACKGROUND OF THE INVENTION

The heart operates as a pump which causes blood to flow throughout the body. In various cases, patients suffer from blockages and/or pressure elevation and it is required to keep a passage open for blood flow. In other patients, an undesired flow path opens and it is required to close the flow path. In such patients, stents, valves or seals are implanted to achieve a required blood flow pattern.

An article titled "Creation with a stent of an unrestrictive lasting atrial communication", by Marc Gewillig et a., Cardiol Young 2002; 12(4):404-7, the disclosure of which is incorporated herein by reference, describes use of a stent to create an unrestrictive and atrial communication. An article titled "Modified technique of stent fenestration of the atrial septum", Stümper et al., 89 (10): 1227, Heart 2003, the disclosure of which is incorporated herein by reference, describes placing a stent across a fenestration and expanding the stent by a balloon.

Various closure devices are known in the art.

PCT publication WO 2005/027752, filed Sep. 13, 2004, the disclosure of which is incorporated herein by reference, describes a closure device formed of a pair of anchor members and a center flexible joint, which press on the septum and hold it closed.

US patent publication 2006/0122647 to Callaghan et al., published Jun. 8, 2006, describes an occlusion device formed of a polymer tube that includes distal and proximal ends for securing to opposite ends of the septum.

US patent publication 2007/0010852, to Blaeser et al., published Jan. 11, 2007, the disclosure of which is incorporated herein by reference, describes a device for sealing a patent foramen ovale (PFO) in the heart. The device includes a right atrial member including a plurality of arms and a cover attached to the arms, and a left atrial anchor including a plurality of arms.

There are also various valves known in the art.

PCT publication WO 2005/074367, published Aug. 18, 2005, the disclosure of which is incorporated herein by reference, describes a plurality of valves and methods of anchoring the valves in the heart. One anchoring method described is use of support arms opposite each other on both sides of a wall through which the valve passes.

US patent publication 2006/0167541 to Lattouf, published Jul. 27, 2006, disclosure of which is incorporated herein by reference, describes a valve formed of a tube with hooks on both ends for anchoring in the heart and a leaflet valve placed in the tube.

US patent publication 2004/0162514 to Alferness, the disclosure of which is incorporated herein by reference, describes a pop-off valve for placement in the heart between the left and right atriums. The valve includes spikes, referred to as anchor guides, which pierce a wall of the heart and thus keep the device in place. Such piercing is not always desirable as it may damage heart tissue.

US patent publication 2006/0116710 to Corcoran et al., the disclosure of which is incorporated herein by reference, describes an occlusion device having a relatively low profile against the occluded tissue.

SUMMARY OF THE INVENTION

An aspect of some embodiments of the present invention relates to a medical implant adapted to define a passage in a tissue wall and to be anchored to the wall by a plurality of arms on both sides of the wall, at least some of the arms not having a matching overlapping arm on the other side of the wall.

The arms optionally extend radially from the defined passage.

In some embodiments of the invention, at least some of the arms do not have a corresponding arm on the other side of the wall, even not a corresponding arm which only partially matches the area of the arm. Alternatively or additionally, one or more of the arms have a corresponding arm on the other side of the wall whose area only partially matches the arm. In this alternative, one or more of the arms having a corresponding arm on the other side of the wall optionally have less than 50% of their length and/or area, matching to an arm on the other side of the wall.

In one embodiment, all the arms do not meet an matching arm on the other side of the wall. By having the arms not press against each other on opposite sides of the wall, the pressure applied by the arms may be more evenly distributed, avoiding forming high pressure stress points on the tissue, which may result in deterioration of tissue at the stressed point and/or may damage the arms themselves.

An aspect of some embodiments of the present invention relates to an anchor device adapted to be implanted across a wall of a body organ such as the heart. The anchor device is adapted to define an opening for blood flow with minimal contact of the blood in the opening with the implant. The length of the opening, measured in the perpendicular axis to the orifice plane, in which blood passing through the opening comes in contact with the implant is less than 3 millimeters or two millimeters. In some embodiments of the invention, the length of the opening is less than a millimeter or even less than half a millimeter. Optionally, the length of the opening is substantially equal to the thickness of the wall around the opening. In some embodiments of the invention, the anchor device defines the opening together with the wall tissue, such that the perimeter of the opening is mostly tissue and only less than 20%, less than 15% or even less than 10% or 7% of the perimeter is covered by the anchor device. Minimizing the length of a blood passage through the opening defined by the device, may improve washout and/or reduce residence time of the blood in the opening, which may result in avoiding tissue growth and/or blood clotting that will obstruct the opening.

An aspect of some embodiments of the present invention relates to an anchor device adapted to define a passage through a wall of a body organ such as the heart, and to be implanted in the wall in a substantially flat configuration, in which the anchor device has a low profile minimal protrusion out of tissue wall. The anchor device is optionally adapted to have a thickness after implantation substantially equal to the thickness of the wall before implantation, for example up to 1 millimeter thicker than the wall or even not more than half a millimeter thicker.

Optionally, in a deployed state of the anchor device its thickness is less than 3 millimeters, less than 2 millimeters or even less than 1 millimeter. In some embodiments of the invention, the thin dimension of the anchor device is perpendicular to the orifice axis and parallel the orifice plane. In some embodiments of the invention, the thickness of the anchor device when implanted on the wall is less than 5%, less than 2% or even less than 1% of the maximum end to end extent of the anchor device in the flat configuration. One potential advantage of using a flat device is that it may allow the device to be absorbed in the wall tissue.

The term low profile refers herein to devices having a thin dimension that does not protrude substantially above a wall on which it is implanted. It is noted, however, that due to irregularity of the wall, the anchor device may not conform entirely to the surface of the wall, possibly diverging from the wall over 20% or even 40% of the area of the anchor device. In some embodiments of the invention, the anchor device is included in a flat plane regardless of the form of the wall. Alternatively, the anchor device may have a thin curved shape.

It is a feature of some embodiments of the invention that the anchor device may serve as a base on which various units may be mounted. These units, which are not necessary for connecting the anchor device to the wall and holding the device in place, are not necessarily included in the low profile of the anchor device.

In some embodiments of the invention, the anchor device is adapted in its flat configuration to hold an orifice in the body wall open, although the orifice is possibly blocked by a valve or closure sheet mounted on the anchor device. For example, the anchor device may hold the orifice open by applying a force in a radial direction, while carrying a closure unit which blocks the orifice in an axial direction. The anchor device optionally holds the orifice open by having some of the parts of the device on one side of the wall and some parts of the device on another side of the wall and the parts on the opposite sides of the wall being connected through the orifice.

In some embodiments of the invention, the anchoring device is adapted for implantation in membranous tissue. Alternatively or additionally, the anchoring device is adapted for implantation in muscle tissue.

The anchoring device optionally defines a central orifice which remains clear from portions of the anchoring device and/or elements mounted thereon, along the length of the anchor device. Optionally, in its deployed configuration, the device includes a plurality of petal shaped elements (referred to herein as petals) extending radially from the central orifice, some of which petals are adapted to be located on one side of the wall and others on the other side of the wall.

In some embodiments of the invention, the anchoring device is formed using a minimal number of pieces (e.g., less than 5), requiring a minimal number of welds or other attachments. Optionally, the device is formed basically of a single elongate piece, e.g., a single wire. In an exemplary embodiment of the invention, the device is produced from a sheet by removing excess material, using a suitable cutting method (e.g., laser, water jet, chemical etching).

The anchoring device optionally does not include sharp points, such as pins or spikes, adapted to penetrate the tissue in order to fasten to the wall. In some embodiments of the invention, the anchoring is performed without penetrating the tissue. Alternatively, spikes may be used to add to the strength of the bonding to the wall.

An aspect of some embodiments of the present invention relates to an anchor device adapted to self expand from a folded state in which the anchor device has a first cross-section area to a deployed state in which the anchor device defines an orifice having a second cross-section area substantially larger than the first cross-section area. Optionally, the anchor device is adapted to be implanted in an orifice in a wall of a body organ such as the heart.

In some embodiments of the invention, the second cross section area is at least 50%, 100% or even by at least 150% greater than the first area. Alternatively or additionally, the diameter of the orifice defined by the anchor device in the deployed state is at least 20%, 30%, 50% or even at least 100% larger than the diameter in the folded state.

In an exemplary embodiment of the invention, the anchor device is delivered in a delivery tool (e.g., a delivery sheath) having a diameter of less than 12 French or even less than 10 French (e.g., 8 French). The anchor device is optionally inserted into a previously dilated orifice with a diameter close to that of the delivery tool, which orifice is expanded by the anchor device to a diameter of at least 12 French, or even to a diameter of 15 French, for example about 18 French. In an exemplary embodiment of the invention, the anchor device is adapted to expand from a diameter of about 4 millimeters when inserted into a deployed state in which it defines an orifice having a diameter of at least 6 millimeters.

In some embodiments of the invention, the dimensions of the orifice defined by the anchor device depend on the thickness and structure of the wall tissue.

The anchoring device may be adapted to keep the orifice open or may carry a flap or other unit which is adapted to close the orifice some times or all the time or may carry a tube, cardiac assist device, a sensor or any other device.

An aspect of some embodiments of the invention relates to a method of perforating an orifice in the septum. The method includes puncturing a small orifice in the septum, inserting an expandable unit into the punctured orifice and expanding the expandable unit to increase the size of the orifice. In some embodiments of the invention, the expandable unit comprises a balloon. Alternatively or additionally, the expandable unit comprises an implant which is implanted in the orifice and remains in the orifice for at least a day, a week or even a month after expanding the orifice.

In some embodiments of the invention, the punctured orifice before expansion has a diameter of less than 3 millimeters, less than 2 millimeters or even not more than 1 millimeter.

Optionally, the anchor device expands most of its expansion upon being released from a delivery tool on which it is brought to the orifice. Alternatively or additionally, the anchor device is adapted to continue its expansion minutes, hours or even days after it is implanted in the hole.

An aspect of some embodiments of the present invention relates to a valve adapted for implantation in a human body in a minimally invasive procedure, formed of an anchoring unit adapted to define a blood passage, and a single flap which covers the entire blood passage. Using a single flap for the valve may make the valve simpler and/or more robust. In some embodiments of the invention, using a single flap directs the blood flow passing through the orifice in an angle relative to the orifice, possibly even perpendicular to the flap, and thus generates in some of these embodiments, a washout flow in a direction different from the primary flow. In addition, the use of a single large flap may allow easier viewing of the flap operation using medical imaging modalities, such as fluoroscopy and ultrasound imaging.

The blood passage may be defined by the anchoring unit itself, such that along the blood passage the blood comes in contact substantially only with the anchoring unit, or by the anchoring unit together with human tissue, such that blood passing through the blood passage contacts both human tissue and the anchoring device.

In some embodiments of the invention, the flap has an area at least 20%, 40%, 70% or even at least 100% greater than the area of the blood passage. Using a flap substantially larger than the blood passage may provide a better closing of the blood passage and/or assure overlap and seal in a relatively flexible and compliant organ. In addition, the large flap may make it easier to open the flap and/or may add to the stability, predictability and/or accuracy of the valve's performance. In some embodiments of the invention, the flap has an area even 120% or 150% greater than the blood passage.

Possibly, a flat sheet, for example having a disc like shape with an orifice larger than the blood passage (referred to herein as a skirt) radially surrounds the blood passage, parallel to the cross section of the orifice. In some embodiments of the invention, the flap is adapted to close against the skirt, such that the skirt optionally protects tissue underneath it from being hit by movements of the flap and/or prevents tissue growth toward the flap. Optionally, the skirt has a width of at least 1 millimeter or even at least two millimeters. In some embodiments of the invention, larger widths of the disc shape are used, for example with a width of at least 5 or even 9 millimeters. Using a large width is expected to prevent cell growth on the skirt. The skirt optionally has a thickness of at least 0.5 millimeters or even at least 0.8 millimeters, which thickness is expected to prevent tissue growth and wrapping on the skirt. Optionally, the distance from the outer edge of the blood passage to the inner edge of the skirt is at least 1 or even at least 2 millimeters, in order to prevent tissue growth in the blood passage.

An aspect of some embodiments of the present invention relates to a valve adapted for implantation in a human body in which a flap of the valve has a hinge substantially remote from the passage covered by the flap. A single flap may cover the entire passage or a plurality of flaps may cooperate to cover the passage. A remote hinge allows for a safe location of the hinge, where it does not obstruct blood flow through the orifice. In addition, when the movement of the flap is based on the spring properties of an arm holding the flap, a long arm provides a low spring constant.

In some embodiments of the invention, a maximal curvature point of the hinge of the flap is at least 1 millimeter, at least 3 millimeters or even at least 5 millimeters or 10 millimeters away from the passageway blocked by the flap. Optionally, the hinge of the flap is separated from the blocked passageway by at least 20%, 40% or even 60% of an end to end extent (referred to herein as the diameter even in non circular shapes) of the cross-section of the passageway.

The hinge optionally extends over a long length of an arm carrying the flap. In such cases when a distance from the hinge is referred to herein, the distance relates to a distance to a maximal curvature point along the hinge. In some embodiments of the invention, the arm is produced with a single hinge. Alternatively, the arm carrying the flap has a plurality of weak points adapted to serve as hinges. In some embodiments of the invention, an integral pivot point of the arm is located in the hinge, optionally close to the maximal curvature point of the hinge. Alternatively to a U shaped hinge in an arm, other hinges may be used, such as a hinge formed of a rotating pin.

An aspect of some embodiments of the present invention relates to a valve adapted for implantation in a human body in which a flap of the valve has a hinge around which it moves between an open and a closed state. The valve also includes a movement restrictor separate from the hinge, which restricts the movement of the flap.

Optionally, the movement restrictor limits at least some movements of the flap allowed by its mounting at the hinge. In some embodiments of the invention, the movement restrictor prevents movements of the flap due to large pressures on the valve, above an allowed level. Alternatively or additionally, a movement restrictor connects the flap to a different point on the valve, in a manner which does not limit the movement of the flap at the hinge, but restricts movement of the flap if the mounting at the hinge breaks.

In some embodiments of the invention, a wire, string or other stopper is positioned in the opening direction of the flap at a position which blocks or at least restricts the movement of the flap beyond the position. Alternatively or additionally, the wire, string and/or stopper is positioned in a manner which restricts the closing of the flap, forcing the flap to be in a partially open state. Further alternatively or additionally, a thin flexible element, such as a wire or string connects the flap to a stationary point, in a manner which prevents undesired movements of the flap. In some embodiments of the invention, the thin flexible element is connected along an arm of the flap, attached to the flap. In some embodiments of the invention, a spring is used instead of or in addition to the thin flexible element.

An aspect of some embodiments of the present invention relates to a valve adapted for implantation in a human body including a flap held by an arm including a hinge. The arm of the flap is adapted to be spread out over the hinge of the arm to an angle of more than 150°, more than 165°, or even substantially 180°. In some embodiments of the invention, the arm is adapted to be spread out during delivery, before being put into operation.

An aspect of some embodiments of the present invention relates to an orifice closing device adapted for use within a human body. The closing device is formed of an anchoring portion which defines an orifice and a closing portion which is adapted to seal the orifice upon deployment, without the aid of tissue growth on the closing device.

In some embodiments of the invention, the anchoring portion is adapted to contact tissue surrounding the orifice in at least two, three or even at least five points. The relative positions of the points at which the anchoring portion is adapted to contact tissue are optionally predetermined before deployment. In some embodiments of the invention, the positions of the contact points are only partially predetermined, for example when the anchoring portion is elastic.

The anchoring portion is optionally a single unit connected at one or more points to the closing portion. Alternatively, the anchoring portion comprises a plurality of separate anchors, which are separately connected to the closure device.

The closing portion optionally covers a larger area than an orifice defined by the anchoring portion, in order to achieve a tight seal. Optionally, the area covered by the closing portion is at least 10%, 20% or even at least 40% greater than the maximal orifice defined by the anchoring portion.

In some embodiments of the invention, the closing device is adapted for use in percutaneous procedures, optionally being deliverable through a catheter having a maximal diameter of less than 18 French or even less than 12 French.

An aspect of some embodiments of the present invention relates to a method of treatment of humans in which an orifice is closed by percutaneously bringing a closure device to an orifice and implanting the closure device in the orifice in a manner which seals the orifice substantially immediately (e.g., less than a minute or even less than ten seconds) upon deployment. The term seal refers herein to a state in which no blood or very little blood (e.g., less than 10 milliliters per minute) passes through the orifice.

An aspect of some embodiments of the present invention relates to an orifice closing device for closing an orifice in a tissue wall of a human, which comprises an opening unit adapted to hold the orifice open and a cover unit adapted to at least partially cover the orifice.

In some embodiments of the invention, the cover unit entirely covers the orifice and prevents flow of blood through the orifice. Alternatively or additionally, the cover unit comprises a mesh which covers the orifice but allows flow therethrough. Optionally, the mesh supports and/or serves as a scaffold for tissue growth. In some embodiments of the invention, the density of the mesh is selected to achieve a desired rate of tissue growth thereon. Further alternatively or additionally, the cover unit has one or more orifices defined therein.

An aspect of some embodiments of the present invention relates to a method of closing an orifice in a body organ. The method includes implanting in the orifice a valve including a bio-degradable material which maintains the valve in an open position or in a state in which it may open and close. As the bio-degradable material dissolves or after it dissolves, the valve changes to a permanently closed state.

In some embodiments of the invention, the bio-degradable material (e.g., Poly Ethylene Glycol (Peg)) prevents tissue growth on one or more portions of the valve. After the bio-degradable material dissolves, tissue growth on the valve closes the valve permanently and thus closes the orifice.

Optionally, the bio-degradable material dissolves after more than 24 hours, more than 3 days or even more than a week or a month.

In some embodiments of the invention, the valve is coated by a material which increases tissue growth, such as vascular endothelial growth factor (VEGF). Alternatively, the valve has rough surfaces which encourages tissue growth. The surface and/or materials that induce tissue growth are optionally coated by the bio-degradable material, such that they do not come in contact with tissue until the bio-degradable material has dissolved. The inducement of tissue growth may be on moving parts of the valve, for example, in order to quickly disable the valve, or on non-moving parts, possibly allowing more time until the orifice closes permanently.

Alternatively or additionally, the bio-degradable material forms a stopper that prevents the valve from closing until it dissolves.

An aspect of some embodiments of the present invention relates to a method of closing an orifice within a heart. The method includes diagnosing a patient to determine a desired time and/or rate at which to close the orifice and selecting a valve having a desired closure profile. The selected valve is then implanted in the patient and gradually moves to a permanently closed state.

In some embodiments of the invention, the rate at which the valve closes is controlled by selecting an amount and/or type of a bio-degradable material which delays the movement of the valve to a permanently closed state. Alternatively or additionally, the rate at which the valve closes is controlled by selecting an amount, location and/or type of a tissue growth enhancement drug. Further alternatively or additionally, the rate at which the valve closes is controlled by selecting dimensions and/or structures of surfaces of the valve. For example, a mesh structure or density may be selected to control tissue growth. Alternatively or additionally, a roughness level of one or more surfaces may be selected.

In some embodiments of the invention, the valve is used in CHF patients and is adapted to gradually close only if it has not encountered high pressures for over a predetermined time. If, however, the valve encounters high pressures, the flow through the valve washes off beginnings of tissue growth and prevents permanent closure due to tissue growth. Thus, if after a while of operation the patient is cured, the valve closes and is covered by tissue. Optionally, the time for which the valve needs to not encounter high pressures until it closes is a feature of the valve and may be adjusted, for example, by setting the roughness of surfaces of the valve, drug amounts and/or the amount of blood it passes when it does not under high pressures.

Optionally, in accordance with these embodiments, if although the patient did not suffer from high pressures, a physician determined that it is too early to allow the valve to permanently close, an override mechanism may be applied from outside the patient in order to open the valve, for example using magnetic or RF coupling, and thus restart the counting of the period until closure. Alternatively or additionally, the valve is adapted to open when the patient performs special exercises and/or other activities, which the patient may be instructed to perform to prevent closure.

Optionally, a kit of closure devices includes a plurality of closure devices which are each marked with an average closure time and/or an opening pressure threshold.

An aspect of some embodiments of the present invention relates to a method of closing an orifice within a heart. The method includes implanting a valve which is adapted to open and close in the patient's heart and at a later time moving the valve to a state in which it is permanently closed by an external intervention.

In some embodiments of the invention, the external intervention is performed by magnetic or RF coupling which is used to change the conditions governing the opening of the valve. Alternatively or additionally, the external intervention includes a percutaneous procedure which accesses the valve to change its operation parameters.

An aspect of some embodiments of the present invention relates to a method of treating an aneurism, for example a septal aneurism. The method includes perforating an orifice in the aneurism and implanting a closure device in the perforated orifice. The closure device strengthens the wall including the aneurism and this avoids the problems associated with the aneurism.

An aspect of some embodiments of the present invention relates to a delivery tool, for delivering a thin element into a patient. The tool includes a central rod, a partially cut tube and an external channel, which surrounds the rod and tube. Delivering a flat element using the delivery tool comprises confining the flat element between the central rod and the partially slotted tube and delivering the tube within a channel which prevents the tube from expanding and releasing the flat element. When the flat element is at its desired location, the channel is retracted relative to the slotted tube, the tube is allowed to expand and releases the flat element.

In some embodiments of the invention, the flat element is a springy element which is held forcefully in the tube. Upon release of the tube from the channel, the springy element exits the tube radially relative to a long axis of the elongate tube, perpendicular to the tube.

In some embodiments of the invention, the delivery tool comprises a percutaneous tool, such as a minimally invasive tool, a catheter or a laparoscope.

An aspect of some embodiments of the present invention relates to a delivery device for leading an implant including one or more loops into a human body. The delivery device includes one or more protrusions which hold the loop between an inner core and an outer channel. As long as the inner core is within the outer channel, the one or more loops of the implant are held by the protrusion. When, however, the inner core is moved beyond the outer channel, the loops are released from the protrusion.

In some embodiments of the invention, until release, the protrusions are adapted to engage the loops in a manner which allows both pull and push the implant.

The implant is optionally mounted into the delivery device in a collapsed state in a manner in which at least portions of the implant are allowed to expand upon release from the channel. In some embodiments of the invention, at least some portions of the implant are allowed to expand without the protrusion releasing one or more of the loops. Optionally, as long as the loop is not released from the protrusion, the expanded portions can be re-collapsed by pulling the implant backwards.

An aspect of some embodiments of the present invention relates to a method of mounting an implant including one or more arms into a delivery tube. The implant is originally packaged in a separate magazine of a diameter substantially equal to the diameter of the delivery tube. The magazine is optionally inserted into a proximal port of the delivery tube, e.g., a haemostatic valve, and the implant is pushed therein from the magazine to the delivery tube.

An aspect of some embodiments of the present invention relates to an implant including a plurality of arms, which includes a string or wire connecting between a plurality of the arms. The string is attached to the arms such that pulling on the string collapses the implant and introduces the implant back into a removal tube, which may be a same tube used for delivery of the implant or a different tube.

In some embodiments of the invention, the implant includes distal and proximal arms and the string connects to each of the proximal arms. Optionally, the string has a central point at which string portions connecting to all the proximal arms meet.

An aspect of some embodiments of the present invention relates to an implant including a plurality of arms having different lengths. Optionally, the arms define loops which may be held by a delivery device during delivery. In some embodiments of the invention, the implant includes at least three or even at least four arms of different lengths. Optionally, the arms of different lengths are adapted to be included in a single plane in a deployed state of the implant and/or are adapted to be directed in a single direction in a folded state, for delivery.

An aspect of some embodiments of the present invention relates to a delivery tool for delivering an implant into a human body. The delivery tool includes an outer channel and an inner rod adapted to engage arms of an implant together with the channel. Pushing the rod distally releases the arms when the point at which they are held is pushed beyond the distal end of the channel. The rod is adapted to engage the arms of the implant at different points along the length of the rod's distal portion, such that pushing the rod distally within the channel gradually releases the arms.

An aspect of some embodiments of the present invention relates to a method of delivering an implant having a plurality of arms in a percutaneous and/or minimally invasive procedure. The method includes separately releasing the arms until a last arm is released and the implant moves into place.

An aspect of some embodiments of the present invention relates to a delivery tool for delivering an implant including a plurality of arms, the delivery tool including a coil adapted to receive the arms. Rotation of the coil optionally separately releases the arms.

An aspect of some embodiments of the present invention relates to an implant including a plurality of arms adapted to participate in anchoring the implant to internal body tissue and a flat sheet fixed to the arms. Optionally, the length of the arms is fixed parallel to the sheet. In some embodiments of the invention, the arms are embedded within the skirt.

In some embodiments of the invention, the implant defines an orifice in the a wall to which it anchors and the sheet does not cover the orifice.

Optionally, the sheet is coated to prevent tissue growth on the sheet. Alternatively, the sheet is coated to induce tissue growth thereon.

In some embodiments of the invention, the implant includes a flap that is adapted to close against the sheet, and the sheet serves to protect tissue from the flap's contact as it closes.

An aspect of some embodiments of the invention relates to a valve adapted to be implanted in internal tissue of a patient. The valve is adapted to open under pressures normally encountered during the cardiac cycle in patients between the right and left atrium, for a first duration of the cardiac cycle and under higher pressures for a second duration of the cardiac cycle different from the first duration.

Optionally, the valve is adapted to open for a larger percentage of the cardiac cycle under pressures encountered between the right and left atrium in patient's under stress than under pressures in normal conditions between the right and left atrium.

In an exemplary embodiment of the invention, the valve is adapted to open in a healthy patient for less than 100 milliseconds or even less than 50 milliseconds in each cardiac cycle. In a patient under a high pressure episode, the valve optionally opens for at least 150 milliseconds, 200 milliseconds or even at least 400 milliseconds in each cardiac cycle. Optionally, the valve is adapted to open at a pressure of at least 2 mmHg, 4 mmHg or even at least 6 mmHg. In some embodiments of the invention, the valve is adapted to open at a pressure difference of at least 6 mmHg or even at least 10 mmHg.

In some embodiments of the invention, when implanted between the right and left atrium, the valve is adapted to pass during the second duration at least 50% more blood than during the first duration. Optionally, during the second duration, the valve is adapted to shunt blood at a rate of at least 600 or even at least 800 milliliters per minute, while during the first duration the valve is adapted to shunt blood at a rate of less than 400 or even less than 300 milliliters per minute.

There is therefore provided in accordance with an exemplary embodiment of the invention, a medical implant, comprising an anchor portion including a plurality of arms adapted to engage an internal tissue wall of a body from two opposite faces, wherein the anchor portion is configured such that at least one of the arms does not have an entirely overlapping arm on the other side of the wall and an opening portion adapted to define an opening for blood flow through the internal tissue wall, when the anchor portion engages the wall.

Optionally, the opening portion is adapted to radially expand in changing from a collapsed state to a deployed state. Optionally, a largest end to end extent of the anchor portion in a deployed state is at least twice the largest end to end extent of the opening defined by the opening portion. Optionally, a largest end to end extent of the anchor portion is at least four times the largest end to end extent of the opening defined by the opening portion. Optionally, the opening portion comprises a ring surrounding the defined opening. Optionally, the anchor portion and opening portion are configured to have a low profile of less than 3 millimeters in a deployed state not on a tissue wall. Optionally, the plurality of arms comprise flexible elongate elements and/or petals. Optionally, in the deployed state at least one of the arms does not have an even a partially overlapping arm on the other side of the wall. Optionally, the arms are configured to surround the orifice in a deployed state and wherein most of the arms are neighbored along a line surrounding the orifice by two arms configured to be on an opposite side of the wall.

Optionally, most of the arms of the anchoring portion do not have arms overlapping them on the other side of the wall, in the deployed state. Optionally, the anchor portion and the opening portion are comprised in a single element. The medical implant optionally includes a mesh mounted on the opening portion.

There is further provided in accordance with an exemplary embodiment of the invention, a medical implant optionally includes a valve mounted on the anchor portion in a manner which regulates flow through an opening defined by the opening portion.

Optionally, the valve is formed together with the anchor portion from a same sheet, wire or tube. Optionally, the valve is at least partially formed from a different material from the anchor portion. Optionally, portions of the implant are covered by ePTFE or polyurethane.

The medical implant optionally includes a motor mounted on the anchor portion and adapted to control the valve. The medical implant optionally includes a sensor mounted on the anchor portion.

There is further provided in accordance with an exemplary embodiment of the invention, a medical implant, comprising an anchor portion adapted to attach to internal tissue of a body; and an opening portion adapted to define an opening for blood flow when deployed within the body, which opening has a length of less than 3 millimeters, in which blood passing through the opening comes in contact with the implant.

Optionally, the anchor portion includes a plurality of arms adapted to be located on opposite sides of the attach to the tissue by including parts adapted to be located on opposite sides of a tissue wall. Optionally, the anchor portion comprises a plurality of elongate elements extending radially from the opening portion, wherein a first group of the elongate elements are adapted to be located on one side of the wall and a second group of the elongate elements is adapted to be located on a second side of the wall.

Optionally, each of the first and second groups comprises at least three elongate elements. Optionally, at least some of the elongate elements comprise petal and/or hoof shaped elements. Optionally, the anchor portion and opening portion are formed from a single piece. Optionally, the implant has a collapsed state and a deployed state and wherein the opening portion is adapted to apply a radial force when released from the collapsed state. Optionally, the opening portion is adapted to cover less than 20% of the perimeter of the opening it defines. Optionally, the anchor portion is configured to engage a tissue wall such that a length in which blood passing through the opening comes in contact with the implant is less than 1 millimeter thicker than the wall. Optionally, the anchor portion and opening portion are configured to have in a deployed state a low profile of less than 3 millimeters. Optionally, the anchor portion and opening portion are configured to have a low profile of less than 15% of an end to end extent of the anchor portion in a deployed state. Optionally, the anchor portion and opening portion are configured to have a low profile of less than 10% of an end to end extent of the anchor portion in a deployed state. Optionally, in the deployed state, the implant does not include parts within the opening defined by the opening portion, beyond parts of the opening portion defining the opening. Optionally, implant optionally includes a skirt surrounding the opening defined by the opening portion.

Optionally, the implant includes a closure unit adapted to block blood flow through the opening. Optionally, the closure unit is part of a valve which controls the extent of blood flow through the opening. Optionally, the anchor portion does not include sharp points. Optionally, the anchor portion includes at least one spike adapted to penetrate the tissue.

There is further provided in accordance with an exemplary embodiment of the invention, a medical implant, comprising an anchor portion adapted to attach to an internal tissue wall of a body; and an opening portion adapted to define an opening in the wall, wherein the implant is configured to have a low profile of less than 5 millimeters in a released state in which it is not subject to external forces.

Optionally, the implant is configured to have a low profile of less than 12% of its largest end to end length in its released state. Optionally, the anchor portion and opening portion are configured to have a low profile of less than 8% of an end to end extent of the anchor portion in the released state. Optionally, the implant is configured to have a low profile not adding to the thickness of the wall more than a millimeter in a deployed state in which the anchor portion is attached to the wall. Optionally, the anchor portion does not include sharp spikes. Optionally, the anchor portion includes a plurality of arms adapted to be located on opposite sides of the tissue wall and to engage the tissue wall between them. Optionally, the anchor portion and opening portion are formed from a single sheet, tube or wire. Optionally, the implant has a collapsed state and a deployed state and wherein the opening portion is adapted to apply a radial force when released from the collapsed state. Optionally, in the deployed state, the implant does not include parts within the opening defined by the opening portion, beyond parts of the opening portion defining the opening. Optionally, the opening portion is adapted to cover less than 40% of the perimeter of the opening it defines.

Optionally, the implant is configured to have a low profile of less than 2.5 millimeters in a released state in which it is not subject to external forces. Optionally, the implant is configured to have a low profile of less than 1 millimeters in a released state in which it is not subject to external forces. Optionally, the anchor portion comprises a plurality of arms adapted to engage a tissue wall from opposite sides and wherein in the released state a height difference between the arms is less than 2 millimeters.

Optionally, the anchor portion comprises a plurality of arms adapted to engage a tissue wall from opposite sides and wherein in the released state the arms intended for the different sides of the wall are in the same plane.

There is further provided in accordance with an exemplary embodiment of the invention, a medical implant, comprising an anchor portion adapted to attach to an internal tissue wall of a body; and an opening portion adapted to define an opening in the wall, wherein the implant is configured to have a collapsed state in which the implant is contained in a cylinder shape of a first diameter, and a deployed state in which the anchor portion engages the wall and the opening portion has a rest state in which it defines an orifice having a second diameter larger than the first diameter.

Optionally, the implant is adapted to self expand from the collapsed state to the deployed state. Optionally, the second diameter is larger than the first diameter by at least 50%.

There is further provided in accordance with an exemplary embodiment of the invention, a method of placing an implant in an orifice in a tissue wall in a body, comprising inserting the implant into the orifice in a collapsed state, releasing the implant so that it engages the tissue wall and allowing the implant to elastically expand while engaging the wall, such that it radially expands within the orifice and expands the orifice. Optionally, the implant expands the diameter of the orifice by at least 20%. Optionally, inserting the implant into the orifice comprises inserting into an orifice in a septum.

Optionally, inserting the implant into the orifice comprises inserting into an orifice made less than six hours before inserting the implant. Optionally, inserting the implant into the orifice comprises inserting into an orifice existent in the patient for at least a week.

There is further provided in accordance with an exemplary embodiment of the invention, a medical valve for implant in a human body, comprising an anchor portion adapted to attach to internal tissue of a body, an opening portion adapted to define an opening for blood flow and a single flap adapted to control the amount of blood flowing through the opening defined by the opening portion.

Optionally, the single flap is adapted to have a closed state in which substantially no blood can flow through the opening. Optionally, the single flap has at least one orifice in the flap which allows flow through the opening even when the flap is in a closed state covering the opening. The valve optionally includes a stopper adapted to prevent the flap from entirely covering the opening defined by the opening portion. Optionally, the single flap has an area at least 10% greater than the cross-section area of the opening. Optionally, the single flap is mounted on an arm with a hinge having a maximal curvature point distanced from the opening defined by the opening portion by more than 0.5 millimeters or even more than five millimeters. Optionally, the single flap is mounted on an arm with a hinge having a maximal curvature point distanced from the opening defined by the opening portion by more than a diameter of the opening. Optionally, the single flap is mounted on an arm with a hinge having a maximal curvature point distanced from a distal point of the anchor portion by more than 1 millimeter. Optionally, the single flap is mounted on an arm with a hinge having a maximal curvature point distanced from a distal point of the anchor portion by more than five millimeters.

Optionally, the valve is configured to open and close without bending the single flap in an area covering the opening. Optionally, the single flap is coated by a biodegradable material. Optionally, the single flap is formed of a metal coated by a polymer. Optionally, the single flap is made of nitinol. Optionally, the single flap comprises a frame and a sheet carried by the frame. Optionally, the single flap and anchor portion are formed in a monolithic process. Optionally, the single flap and anchor portion are produced separately and then combined. Optionally, the single flap is mounted on the anchor portion through an arm having a plurality of weak points adapted to serve as hinges. Optionally, the single flap is mounted on the anchor portion through an arm with an angle of at least 30° between the flap and the arm in a closed state of the flap. Optionally, the single flap is mounted on the anchor portion through a plurality of arms.

There is further provided in accordance with an exemplary embodiment of the invention, a medical valve for implant in a human body, comprising an anchor portion adapted to attach to internal tissue of a body, an opening portion adapted to define an opening for blood flow, a flap adapted to cover at least a portion of the opening; and an arm connecting the flap to a hinge at least 1 millimeter away from the opening. Optionally, the hinge is distanced from the opening by more than 3 millimeters. Optionally, the hinge is distanced from the anchor portion by more than 3 millimeters. Optionally, the flap and arm are formed as a single piece. Optionally, the arm, anchor portion and opening portion are formed as a single piece. Optionally, the arm is folded in a manner which forms a hinge around which the flap opens and closes. Optionally, the arm is adapted to be stretched out during delivery into the patient such that the arm around the maximal curvature point of the hinge has an angle of at least 160°. Optionally, the arm comprises a plurality of arms.

There is further provided in accordance with an exemplary embodiment of the invention, a medical valve for implant in a human body, comprising an anchor portion adapted to attach to internal tissue of a body, an opening portion adapted to define an opening for blood flow, a flap adapted to controllably cover at least a portion of the opening, a hinge on which the flap moves between an open state and a closed state in which it covers the opening and a movement restrictor separate from the hinge, adapted to restrict the movement of the flap.

Optionally, the valve is adapted to be delivered into a body in a percutaneous procedure, for example through a catheter. Optionally, the movement restrictor comprises a thin flexible element stretched behind the flap in a manner which limits its movement away from the opening portion. Optionally, the thin flexible element is connected at a plurality of points to the anchoring portion or to a skirt mounted on the anchoring portion. Optionally, the movement restrictor comprises a thin flexible element which connects the flap or an arm connecting the flap to the hinge, to the anchor portion or another element which does not move with the flap. Optionally, the movement restrictor is configured to restrict movement of the flap only if another portion of the valve fails. Optionally, the movement restrictor comprises a tab or sheet.

There is further provided in accordance with an exemplary embodiment of the invention, a medical valve for implant in a human body, comprising an anchor portion adapted to attach to internal tissue of a body, an opening portion adapted to define an opening for blood flow, a flap adapted to controllably cover at least a portion of the opening and an arm connecting the flap to the anchor portion, wherein the arm is adapted to have an operation state in which it is folded and defines a hinge for the flap and a delivery state in which the arm has an angle of at least 150 degrees at the hinge.

Optionally, the arm is adapted to have an angle of substantially 180 degrees at the hinge in the delivery state.

There is further provided in accordance with an exemplary embodiment of the invention, an orifice closing implant, comprising an opening portion adapted to define an opening for blood flow in internal tissue of humans and to hold the opening open; and a cover mounted on the opening portion and covering the opening.

Optionally, the cover and opening portion are adapted to be delivered together into a patient in a percutaneous procedure. Optionally, the cover is adapted to seal the opening defined by the opening portion. Optionally, the opening portion is adapted to anchor the implant to the internal tissue. Optionally, the cover comprises at least one hole allowing blood flow therethrough. Optionally, the cover comprises a mesh pre-attached to the opening portion.

Optionally, the cover comprises a material which encourages tissue growth. Optionally, the cover and anchor portion are produced separately and later combined. Optionally, the cover and anchor portion are produced together in a monolithic process. Optionally, the cover and anchor portion are produced from different materials.

There is further provided in accordance with an exemplary embodiment of the invention, an orifice closing implant, comprising an anchoring portion adapted to connect to tissue within a patient and define an opening for blood flow in internal tissue of humans; and a closing portion adapted to seal the opening upon deployment without the aid of tissue growth, the closing portion and the anchoring portion are adapted to be delivered together into a patient in a percutaneous procedure.

Optionally, the closing portion has an area at least 20% greater than the opening defined by the anchoring portion. Optionally, the anchoring portion is connected to the closing portion in at least three points.

There is further provided in accordance with an exemplary embodiment of the invention, a method of closing an orifice in internal human tissue, comprising bringing a closure device to an orifice in a percutaneous procedure; and placing the closure device on the orifice in a manner which seals the orifice immediately upon placement.

There is further provided in accordance with an exemplary embodiment of the invention, an implant, comprising a valve adapted for implantation in a patient; and a bio-degradable material placed on the valve in a manner which prevents permanent closure of the valve and in a manner which slowly dissolves when the valve is implanted in a patient.

Optionally, the valve is adapted to be delivered to an internal body organ in a percutaneous procedure. Optionally, the bio-degradable material is adapted to dissolve over a period longer than a week. Optionally, the bio-degradable material prevents tissue growth.

Optionally, at least one surface of the valve is coated by a drug which enhances tissue growth, and the drug is coated by a bio-degradable material which delays the tissue growth until it is dissolved. Optionally, the biodegradable material forms a stopper which prevents closing of the valve. Optionally, the valve is adapted to move to a permanently closed state due to its interaction with body tissue, after the biodegradable material dissolves.

There is further provided in accordance with an exemplary embodiment of the invention, a method of closing an orifice in the blood system of a patient, comprising diagnosing a patient to determine a desired closure profile of an internal orifice, selecting a valve responsive to the determined closure profile and implanting the selected valve in the internal orifice, such that after implantation the valve is adapted to open and close and allowing the selected valve to change to a permanently closed state.

Optionally, selecting the valve comprises selecting a valve having an average time between implantation and permanent closure closest to a desired time for the patient.

Optionally, implanting the valve comprises implanting in a percutaneous procedure. Optionally, selecting the valve comprises selecting a valve which includes a biodegradable material which delays the movement to permanent closure. Optionally, selecting the valve comprises selecting a valve having one or more surfaces adapted to encourage tissue growth. Optionally, selecting the valve comprises selecting a valve which moves to a permanently closed state if the valve is not opened for at least a predetermined amount of time. Optionally, selecting the valve comprises selecting a valve adapted to change to the permanently closed state not less than a month after implantation.

There is further provided in accordance with an exemplary embodiment of the invention, a method of closing an orifice in the blood system of a patient, comprising implanting a valve in the patient such that closing the valve prevents passage of blood through the orifice and changing a state of the valve to a state in which it is permanently closed and does not allow passage of blood. Optionally, moving the valve to the state in which it is permanently closed comprises transferring the valve to the permanently closed state at least a week after implanting the valve.

Optionally, the valve opens and closes a plurality of times before moving to the permanently closed state. Optionally, implanting the valve comprises implanting a valve coated by a bio-degradable material which prevents tissue growth on the valve. Optionally, moving the valve to the permanently closed state comprises having tissue grow on the valve.

There is further provided in accordance with an exemplary embodiment of the invention, a method of treating an aneurism, comprising identifying an aneurism in a patient, perforating a hole in the aneurism and implanting a closure device in the hole.

There is further provided in accordance with an exemplary embodiment of the invention, a delivery tool for delivering an implant into a patient in a percutaneous procedure, comprising a central rod, a slotted tube along part of its perimeter at a distal end thereof, mounted on the central rod, the tube being adapted to receive a flat implant part between the tube and the central rod; and an outer channel surrounding the central rod and the tube, the channel being adapted to be retracted relative to the tube, edges of the tube around the cut are adapted to expand the tube when the outer channel is retracted, and allow the flat implant part to exit the tube in a direction perpendicular to the rod.

Optionally, the tube is cut over between 10-25% of its perimeter along at least a portion of its length.

There is further provided in accordance with an exemplary embodiment of the invention, a delivery tool for delivering an implant into a patient in a percutaneous procedure, comprising a channel adapted to be placed in a blood vessel of a patient for leading an implant to an internal organ of the patient, an elongate rod adapted to pass into the channel; and a notched head mounted on a distal end of the rod, the head having areas in which its radial size is smaller than the inner cross-section of the channel, such that a wire of an implant can fit between the notched head and the channel and having at least the protrusion which substantially touches the channel, such that a loop of an implant can fit around the protrusion and can be pulled proximally by pulling the rod proximally.

Optionally, the head comprises at least three protrusions adapted to receive respective loops of an implant. Optionally, the head comprises behind the at least one protrusion a protruding ring, such that a loop head of the implant is caught between the protrusion and the protruding ring and moving the head distally pushes the implant distally.

There is further provided in accordance with an exemplary embodiment of the invention, a method of delivering an implant in a percutaneous procedure, comprising providing a delivery tool including a channel and internal rod, mounting an implant including arms with loops in the delivery tool, in a manner such that the implant moves distally and radially with movements of the rod and delivering the implant through the delivery tool to an internal body organ; and releasing the implant in the internal body organ.

Optionally, mounting the implant comprises mounting the loops on a coil shaped wire. Optionally, mounting the implant comprises mounting the loops between protrusions on a distal end of the rod and the channel.

Optionally, releasing the implant comprises releasing a plurality of arms together. Alternatively or additionally, releasing the implant comprises releasing at least two of the arms separately. Optionally, the method includes diagnosing the patient and selecting the implant responsive to the diagnosis.

Optionally, diagnosing the patient comprises determining a thickness of a tissue wall in the patient. Optionally, diagnosing the patient comprises diagnosing the patient using the delivery tool. Optionally, selecting the implant comprises selecting an implant having a desired anchor portion responsive to the diagnosis.

There is further provided in accordance with an exemplary embodiment of the invention, a method of delivering an implant into a patient, comprising providing an implant including an anchor portion, an opening defining portion, a flap and an arm connecting the flap to the anchor portion, mounting the implant with the arm at least partially folded over itself; and inserting the implant with the folded arm into a catheter channel.

Optionally, the implant is adapted to operate in a first configuration in which the arm is folded over itself, and wherein inserting the implant into the catheter channel comprises inserting with the arm folded at a different point than in the first configuration.

There is further provided in accordance with an exemplary embodiment of the invention, a method of delivering an implant into a patient, comprising inserting an implant into a magazine having an inner diameter, passing the magazine into a proximal port of a delivery tube having an inner diameter substantially the same as the inner diameter of the magazine and advancing the implant from the magazine into the delivery tube.

Optionally, inserting the implant into the magazine comprises inserting the implant into the magazine in a folded state in which arms of the implant attempt to expand and are prevented from expanding by the magazine. Optionally, passing the magazine into a proximal port of the delivery tube comprises passing through a haemostatic valve.

There is further provided in accordance with an exemplary embodiment of the invention, a medical implant, comprising an anchor portion including a plurality of arms and a wire connecting a group of the arms of the anchor portion in a manner which allows folding the group of arms by pulling the wire at a single point.

Optionally, the anchor portion has a folded state in which it has distal and proximal arms and wherein the wire is connected to the proximal arms. Optionally, the wire is connected to at least three arms. Optionally, the anchor portion is adapted to self expand from a folded state to an expanded state.

There is further provided in accordance with an exemplary embodiment of the invention, a medical implant, comprising an anchor portion including a plurality of arms adapted to anchor in internal tissue of a patient; and a flat sheet fixed to the arms.

Optionally, the plurality of arms are adapted to anchor to a tissue wall by having some of the arms located on one side of the walls and others of the arms on the other side of the wall. Optionally, the plurality of arms are adapted to define a passage. Optionally, the flat sheet is adapted to surround the passage but not cover the passage. Optionally, the flat sheet has a disc shape. Optionally, the inner perimeter of the flat sheet is distance from the defined passage by at least 1.5 millimeters. Optionally, the inner perimeter of the flat sheet is substantially leveled with the defined passage. Optionally, the flat sheet is adapted to cover the passage. Optionally, the plurality of arms are adapted to attach to the sheet with their length parallel the plane of the sheet.

The medical implant optionally includes an additional sheet on an opposite side of the anchor portion. Optionally, the plurality of arms are adapted to attach to the sheet with some slack, allowing for a wavy shaped skirt.

There is further provided in accordance with an exemplary embodiment of the invention, a method of generating a hole in an internal tissue wall of a patient, comprising puncturing a small orifice in a tissue wall, inserting an expander into the orifice; and applying substantially only radial forces by the expander to expand the hole.

Optionally, the expander comprises a balloon and/or an implant which is left in the orifice after it is expanded. Optionally, puncturing the small orifice comprises puncturing an orifice having a diameter of less than 2 millimeters. Optionally, applying the radial forces comprises increasing the diameter of the orifice by at least 20% or even by at least 50%.

There is further provided in accordance with an exemplary embodiment of the invention, an implant for internal tissue, comprising an anchor portion adapted to anchor the valve in a patient and a valve adapted to open for a first percentage of the cardiac cycle when subject to pressures between the left and right atrium of a healthy patient and for a second percentage of the cardiac cycle when subject to the pressures between the left atrium and the right atrium of a patient with a high pressure level. Optionally, the implant is adapted to open for pressures above a threshold which is lower than 7 mmHg.

BRIEF DESCRIPTION OF THE DRAWINGS

Exemplary non-limiting embodiments of the invention will be described with reference to the following description of the embodiments, in conjunction with the figures. Identical structures, elements or parts which appear in more than one figure are preferably labeled with a same or similar number in all the figures in which they appear, and in which.

DETAILED DESCRIPTION OF EXEMPLARY EMBODIMENTS

Overview

Figure 1:
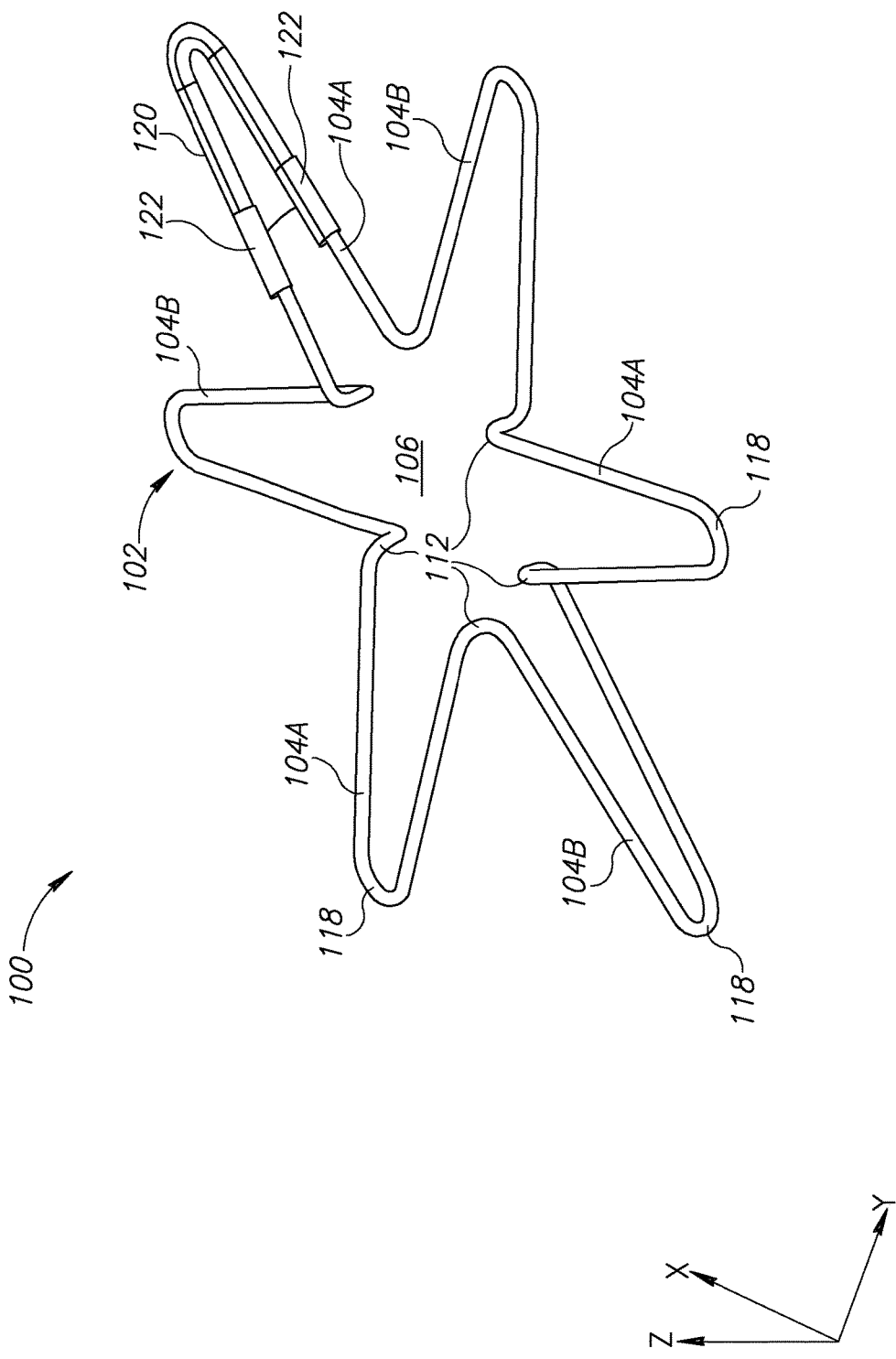
FIG. 1 is a schematic illustration of an anchoring device in a deployed configuration, in accordance with an exemplary embodiment of the present invention.

FIG. 1 is a schematic illustration of an anchoring device 100 in a deployed configuration, in accordance with an exemplary embodiment of the present invention. Device 100 is adapted for use within internal organs of a patient, for example in the heart. Anchoring device 100, as well as the other anchoring device embodiments described hereinbelow, may be used on its own to hold an orifice open or may carry one or more functional devices, such as a valve, a closure device, a tube and/or any other device requiring anchoring within a patient.

While device 100 is suitable for use in many body organs, it is especially useful for organs which move and endure varying pressures, such as the heart. Device 100 is optionally adapted for use in organs which are sensitive to formation of embolisms and is designed to minimize the chances of formation of embolisms.

Device 100 comprises a single wire 102 formed into a plurality of petals 104 (marked 104A and 104B) extending radially from a central orifice 106, defined by an imaginary circle, ellipse or any other shape (e.g., a polygon) connecting curve points 112, between petals 104. Petals 104A are optionally designed to be slightly higher than petals 104B (in the Z direction in FIG. 1), such that when deployed within an orifice in a wall, petals 104A are located on one side of the wall and petals 104B are on the other side of the wall. In some embodiments of the invention, the distance between the planes of petals 104B and pf petals 104A is less than 3 millimeters or even less than 1.5 millimeters. In an exemplary embodiment of the invention, the distance is about 2.5 millimeters. Alternatively, the distance is about 1 millimeter or more. Alternatively, petals 104A and 104B are included in a single plane, such that the profile of device 100 is equal to the thickness of the wire 102 or sheet from which the device is produced, for example about 0.3 millimeters or possibly even less than 0.1 millimeters.

Curve points 112 are designed to abut against the wall tissue facing orifice 106 and prevent the tissue from substantially extending into central orifice 106. Thus, when located within an orifice in a wall of the heart, the wall is caught between petals 104 and is held open by curve points 112. Curve points 112 are optionally designed to have a relatively large curve radius, so as to better endure the forces applied to wire 102 at the curve points. As discussed below, a wire of the same material as wire 102 or a different material such as fabric, optionally connects curve points 112.

In some embodiments of the invention, wire 102 is formed into its closed shape using two crimped tubes 122 which connect the ends of wire 102 together at two different points, defining an overlap portion 120 between the ends of wire 102. The use of two crimped tubes 122 adds to the stability of the device and locks against torque. Optionally, crimped tubes 122 are attached at middle points along the length of a petal 104A. Alternatively or additionally, crimped tubes 122 may be connected closer to the base or closer to the tip 118 of the petal 104A. Further alternatively or additionally, other devices may be added to device 100 to increase its stability and/or a simple attachment at the distal end of the petal is used, as described below with reference to FIG. 2B. Overlap portion 120 may optionally also be used to define and/or determine a preferred angle and/or position of device 100. Instead of crimp tubes 122, other methods and/or devices may be used, such as soldering, welding and/or glue bonding. Tubes 122 may be made from any suitable biocompatible material, such as nitinol, titanium or stainless steel.

Exemplary Structure and Sizes

In some embodiments of the invention, as shown in FIG. 1, petals 104A and petals 104B are arranged alternately around central orifice 106, such that each petal 104A is neighbored by two petals 104B on opposite sides. A different arrangement of petals, in which two petals on one side of the wall are not separated by petals on the other side of the wall is described below with reference to FIG. 12. Petals 104A and 104b are optionally adapted to the side of the wall they are to engage according to their height. Alternatively or additionally, petals 104A and 104B are adapted to their intended side of the wall by being pre-bent differently as to the configuration they are to have in the deployed state. Further alternatively or additionally, petals 104A and 104B are adapted to their intended side of the wall by being designed to be folded in a specific direction in delivery.

As shown in FIG. 1, device 100 includes six petals. In some embodiments of the invention, however, the device may have more petals, so as to better define a circular border for central orifice 106, as a circular shape is better compatible to the body in some cases, for example in not having sharp edges. On the other hand, fewer petals makes device 100 simpler, possibly allowing easier delivery. Exemplary numbers of petals include between 4 to 20, although more, and possibly fewer may be used under some circumstances. In some embodiments of the invention, the anchoring device includes an even number of petals, optionally half of the petals being intended for each side of the wall. It is noted, however, that anchoring devices in accordance with embodiments of the present invention may have odd numbers of petals, such as 5, 7 or 9 petals.

Petals 104 are optionally sufficiently long to stabilize on a tissue wall (e.g., prevent slippage), while not being too long as in general it is desired to minimize the material inserted into body organs. In an exemplary embodiment of the invention, one or more of petals 104 is longer than 3 mm, longer than 5 mm, or even longer than 8 mm as measured from curve points 112 to their tips radially farthest from the curve points. Possibly, however, petals 104 are shorter than 10 mm or even shorter than 6 mm.

Figure 12:
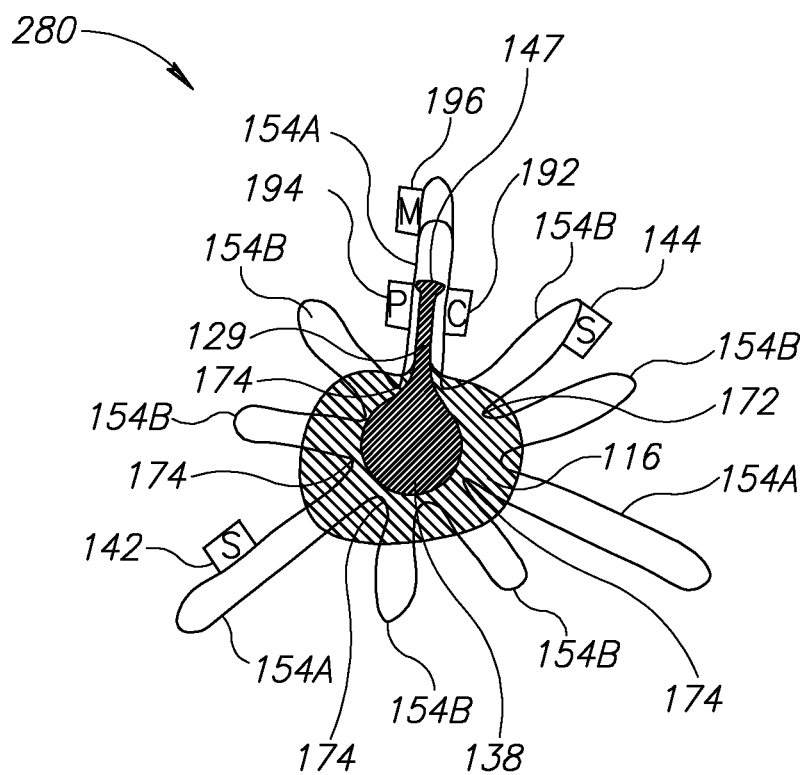
FIG. 12 is a schematic top view of an implantable flow control device, in accordance with an exemplary embodiment of the invention.

In some embodiments of the invention, all of petals 104 have a same shape, width and length. In other embodiments, however, different petals have different lengths, widths and/or shapes (for example as shown in FIG. 12). For example, petals 104A intended for a first side of the wall (e.g., the right atrium) may be longer than petals 104B for the other side of the wall (e.g., the left atrium), for example due to different expected pressures. In another exemplary embodiment, one of petals 104A may be made longer or wider than the other petals 104A in order to define a desired orientation of device 100. Further alternatively or additionally, one or more of petals 104 may be made shorter in order to conform to the geometry of the body organ in which device 100 is to be implanted.

As shown, petals 104 have a relatively wide base close to central orifice 106, which narrows toward their tips 118, possibly substantially monotonously. In some embodiments, having a wide base and narrower tip makes it easier to fold device 100 for delivery and for removal, if necessary. Alternatively, as discussed hereinbelow, petals 104 may have other shapes. For example, petals 104 may have a narrow base which monotonously expands, especially in embodiments including a skirt 116 (FIG. 4A below), as the expanding petals may prevent slippage of the skirt during delivery. In another exemplary embodiment of the invention, petals 104 have a constant width and/or have an expanded distal end.

Petals 104 are optionally biased to apply pressure toward the wall on which they are placed, so that the wall is firmly caught between petals 104A and 104B, which serve as a double spring. In addition to making the petals firmly hold the wall, the bias of petals 104 optionally tensions curve points 112 and thus increases the radial force applied by curve points 112. Alternatively, petals 104 are in a rest state against the wall, so as not to press hard against the wall which may be damaged by too much pressure. In some embodiments of the invention, petals may me curved away of the wall at their distal tips 118 or may be curved back to pressure the wall at tip 118. Possibly, petals 104 are coated with a material adapted to encourage tissue growth around device 100, such that device 100 is embedded in the wall, after a while.

The extent to which petals 104 are biased, the distance in the axial (Z direction) between petals 104A and 104B and possibly other parameters of device 100, such as the thickness of wire 102, the length of petals 104 and/or the number of petals, optionally depend on characteristics of the tissue in which the device is to be implanted. The characteristics of the tissue may include, for example, one or more of the thickness of the wall in which the device is to be deployed, the calcium content of the tissue, the electrical properties of the tissue and an extent of scarring of the tissue. In an exemplary embodiment of the invention, a plurality of devices 100 which differ in their parameter values are produced. The device actually used on a specific patient is selected according to the characteristics of the patient. For example, a device 100 with longer petals and/or a stronger bias of the petals toward the tissue is optionally used for softer tissue from which the device may slip.

The distance in the Z direction between petals 104A and 104B is optionally selected according to the thickness of the wall on which device 100 is implanted. In some embodiments of the invention, the total thickness of device 100, when deployed, is less than 3 millimeters, less than 2 millimeters or even less than a single millimeter. Alternatively or additionally, upon implantation on a wall, device 100 extends beyond the wall, on both sides of the wall together, by less than 2 millimeters, 1 millimeter or even less than 0.6 millimeters. The thickness of device 100 is optionally less than 3%, 1% or even less than 0.5% of the largest diameter of the area defined by the tips of petals 104.

Materials and Production

Wire 102 optionally has a circular profile, which does not have sharp edges. Alternatively, wire 102 may have any other convenient profile, for example a rectangular or square cross section. Wire 102 is optionally thin, having a thickness of less than 1 millimeter, less than half a millimeter or even less than 0.3 millimeters, in order to minimize the amount of foreign material in the patient's body and allow folding into a delivery device. In some embodiments of the invention, wire 102 has a thickness of more than 0.1 millimeters or even more than 0.25 millimeters, so that it has sufficient strength to resist tissue pressures in anchoring to a tissue wall. Optionally, over its entire length, wire 102 has a same thickness. Alternatively, the cross-section shape and/or thickness of wire 102 may vary over its length, for example to have additional strength at curve points 112. In some embodiments of the invention, the variable thickness of wire 112 is achieved in an etching process and/or an electropolishing process.

In some embodiments of the invention, device 100 is produced from a wire which is bent into the desired shape of device 100. Alternatively, device 100 is produced from a sheet which is etched or cut into the desired shape. This alternative may be considered advantageous in embodiments in which it is desired to have different stiffness of the wire of petals 104 in different directions.

Wire 102 may comprise substantially any bio-compatible material, such as nitinol, stainless steel or a flexible hard polymer. Wire 102 optionally comprises an elastic springy material, for example a super-elastic material.

Nitinol has several advantages for use in anchoring device 100. Its super-elasticity allows anchor device 100 to be collapsed for delivery into a small diameter and nitinol is considered highly bio-compatible.

Possibly, the outer surface or wire 102 is relatively smooth. Alternatively, the outer surface of wire 102 is roughened, for example, in order to induce growth of tissue cells thereon and thus cause wire 102 to be embedded partially or entirely in the wall. The roughening is optionally performed using any suitable method known in the art, such as applying micronic layers of a porous polymer such as polyurethane by, for example, electrospinning, applying fractal (e.g., ceramic) coatings such as Titanium Nitride (TiN) or Iridium Oxide (Irox) and/or applying other coatings which are used to increase capacitance of electrodes.

Alternatively or additionally, wire 102 is coated with one or more materials that encourage tissue growth and/or with other materials, such as anti-inflammation (e.g., steroids) and/or other drugs, such as a heparin-emitting polymer. The coating or roughening may be added over the entire wire 102 or may be added only on parts thereof. In an exemplary embodiment of the invention, only the petals 104 to be located on one side of the wall, e.g., intended to be located in the left atrium are coated. Alternatively or additionally, only the distal ends of the petals are coated, leaving the proximal ends of the petals without tissue growth, such that the orifice 106 is not blocked by tissue growth.

The portions coated are optionally selected in a manner which minimizes inflammation and/or adverse reaction of the body to device 100. In some embodiments of the invention, the portions coated are selected in a manner which is directed to achieve a desired size of orifice 106 and/or length of flow through orifice 106.

In some embodiments of the invention, metallic components of device 100, such as wire 102 and/or skirt 116, undergo processes such as electro-polish and/or passivation, on some or all of the surfaces in order to prevent chemical contamination and/or to prevent exposed surfaces from reacting with the environment. Alternatively or additionally, wire 102 is encased in a thin ePTFE (expanded polytetrafluoroethylene) cover, in order to improve the hemocompatibility of the wire without substantially changing its mechanical characteristics.

Device 100 optionally minimizes the amount of foreign material participating in defining an orifice in a patient and coming in contact with the blood stream passing through the orifice. In some embodiments of the invention, less than 20%, less than 15% or even less than 10% of the perimeter of the orifice is covered by parts of device 100. For example, an opening of 5 millimeters in diameter has a circumference of about 15 millimeters. If wire 102 has a thickness of 0.3 millimeters and crosses orifice 106 at six curve points 112, the total perimeter area covered by wire 102 is 1.8 mm, which is 12% of a 15 millimeter perimeter.

In some embodiments of the invention, device 100 does not include pins or spikes which penetrate body tissue, thus being less traumatic to the tissue wall in which the device is implanted. Alternatively, for example in order to provide a better coupling, device 100 includes pins or spikes which penetrate the tissue wall.

Additional Embodiments of Anchor Device

Figure 2A:
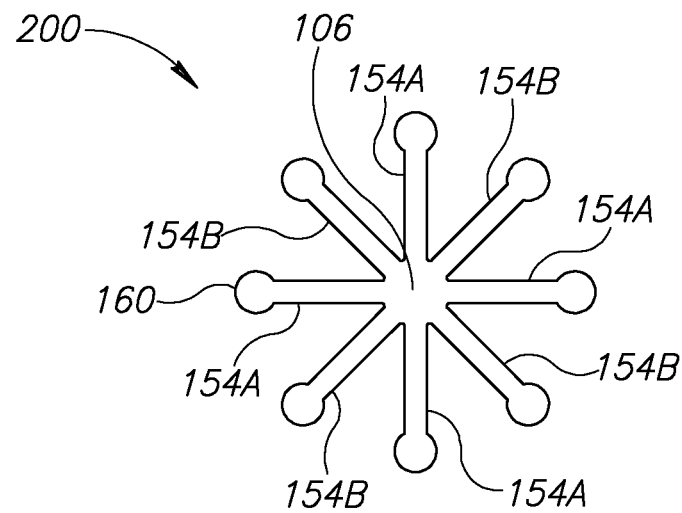
FIGS. 2A-2E are schematic illustrations of implant devices, in accordance with other exemplary embodiments of the invention.

FIG. 2A is a schematic illustration of an implant device 200, in accordance with another exemplary embodiment of the invention. Device 200 includes eight petals 154 (marked 154A and 154B), arranged intermittently around a central orifice 106. In device 300, the distal ends of petals 154 include a head of increased size 160, which better anchors the petals on the wall, for such cases in which additional anchoring is required.

Figure 2B:
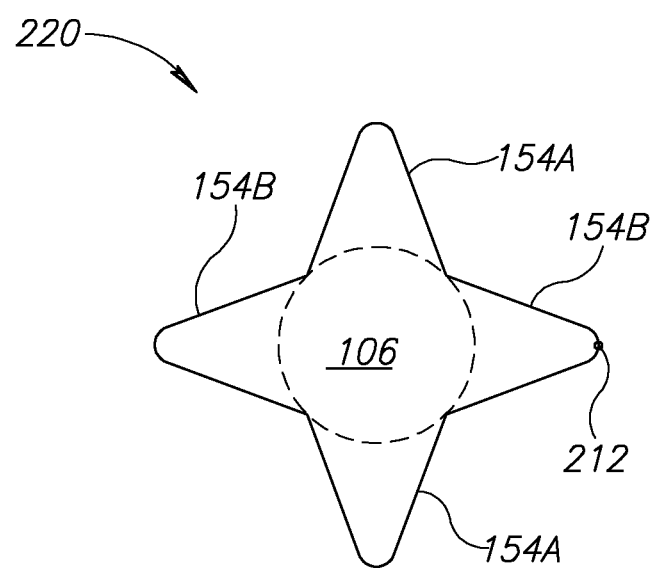

FIG. 2B is a schematic illustration of an implant device 220, in accordance with still another exemplary embodiment of the invention. Device 220 includes four petals 154, such that on each side of the wall there are only two petals. One of the petals has a connection point 212, at which the ends of the wire forming the device are connected.

Figure 2C:
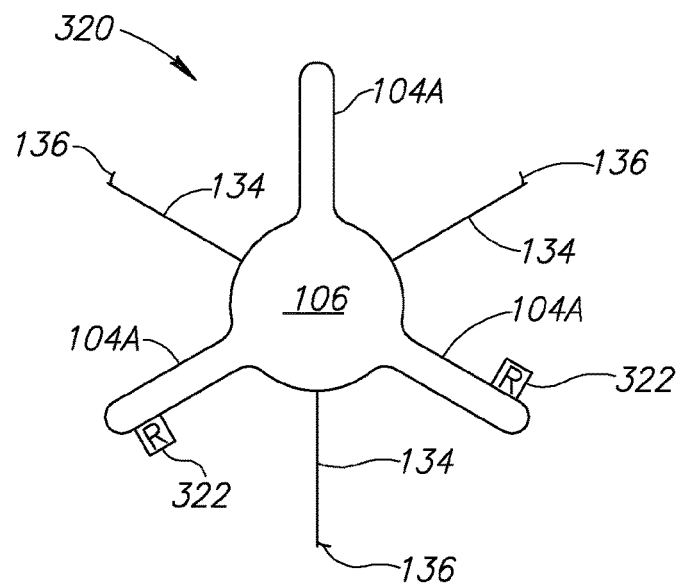

FIG. 2C is a schematic illustration of an implant device 320, in accordance with still another exemplary embodiment of the invention. Device 320 includes three petals 104A, for a first side of a wall on which device 320 is mounted, and three thin bars 134 for an opposite side of the wall. In an exemplary embodiment of the invention, device 320 is implanted in the septum, thin bars 134 are located in the left atrium and petals 104A are located in the right atrium. Thus, the amount of material in the left atrium is minimized. In some embodiments of the invention, one or more of bars 134 has a pin 136 along its length, for example at its distal end, which pin is used to anchor the bar in the septum.

Device 320 includes, in some embodiments of the invention, one or more drug reservoirs 322, for example mounted on one or more of petals 104A. The reservoirs 322 optionally contain a drug, such as a steroid, which is slowly released from the reservoir according to a predetermined scheme and/or according to instructions from a controller. Alternatively, the drug is contained in a coating of the device.

Figure 2D:
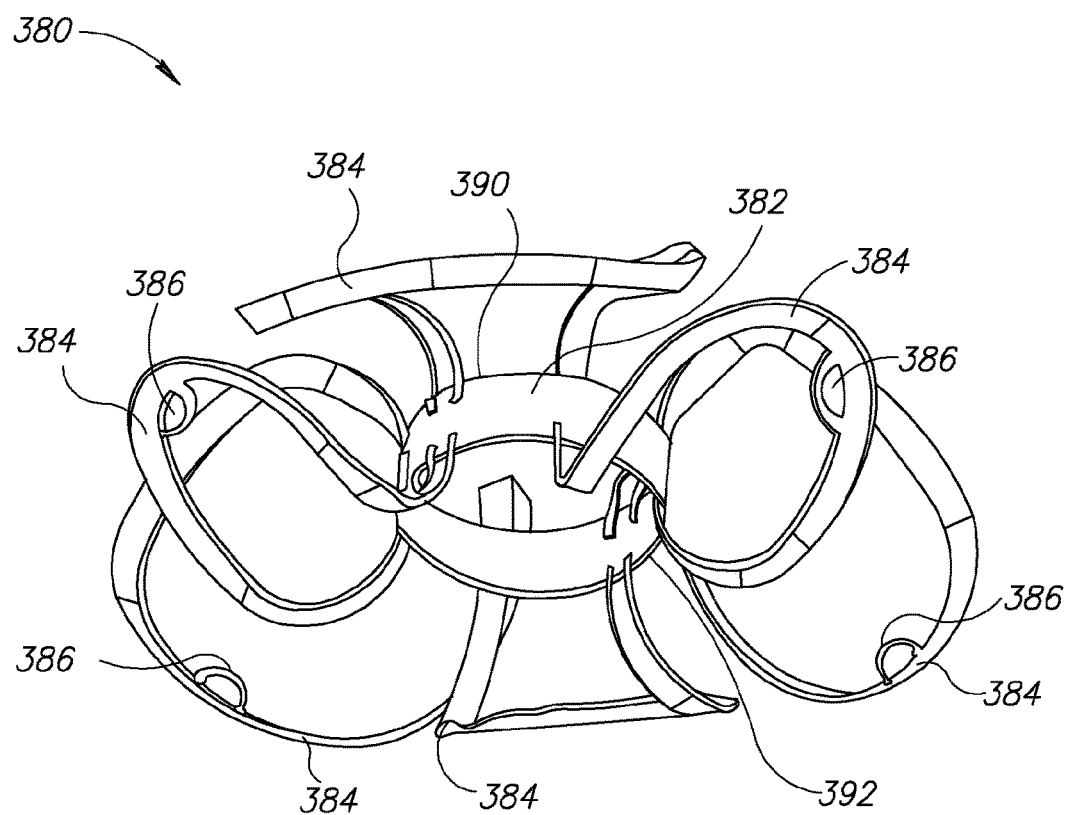

FIG. 2D is a schematic view of an anchoring device 380, in accordance with an exemplary embodiment of the invention. Anchoring device 380 comprises a central ring 382, which defines a passage and prevents tissue from entering and occluding the passage. A plurality of petals 384 extend radially from ring 382. Some of the petals extend from an upper side 390 of the ring 382, while others extend from a bottom 392 of the ring, such that petals 384 can engage a tissue wall, in which ring 382 is positioned, between them. Optionally, unlike petals 104, petals 384 are curved along their extent from ring 382 to their distal end, in a manner which avoids harsh bends, which may cause breakage and in a manner which increases the pressure of the distal ends of petals 382 against the tissue wall. In some embodiments of the invention, some or all of petals 384 define a respective loop 386 along their length, for example at their distal end. Loop 386 is optionally used for engagement of the petals during delivery. Device 380 is particularly suitable for production by laser cutting or etching out of a tube, although other methods of production may also be used. Device 380 is considered particularly suited for embodiments in which a tube is carried by the anchoring device, for example a tube having a length of more than 3 or even 5 millimeters. Device 380 is sufficiently massive to carry such a tube and its being less foldable is not a concern in view of the tube which it carries.

Optionally, as shown, ring 382 comprises a solid sheet, for example of nitinol or a thermoplastic material. Alternatively, ring 382 comprises a net texture, in order to minimize its material content and allow folding during delivery into the patient. Use of a net texture may also serve in anchoring ring 382 to the tissue. Ring 382 optionally has a minimal height, of less than 5 millimeters, less than 3 millimeters or even less than 1 millimeter, in order to minimize the extent of foreign material within the patient and the length of contact between blood flow and ring 382. Alternatively or additionally, ring 382 may be cut or slit, forming an open ring or being formed of a plurality of separate portions. In some embodiments of the invention, ring 382 is coated entirely or at specific areas of the ring, with a porous layer which enhances tissue growth. Alternatively or additionally, ring 382 defines an internal drug reservoir which gradually releases a drug, for example an anti-inflammatory drug.

Other symmetric or non-symmetric arrangements may be used for anchoring devices in accordance with embodiments of the invention.

In the above embodiments, petals intended to be on opposite sides of the tissue wall are not located directly on opposite each other, in order to avoid excess pressure on specific points of the wall. In other embodiments of the invention, petals are located partially or entirely parallel each other on opposite sides of the wall.

Figure 2E:
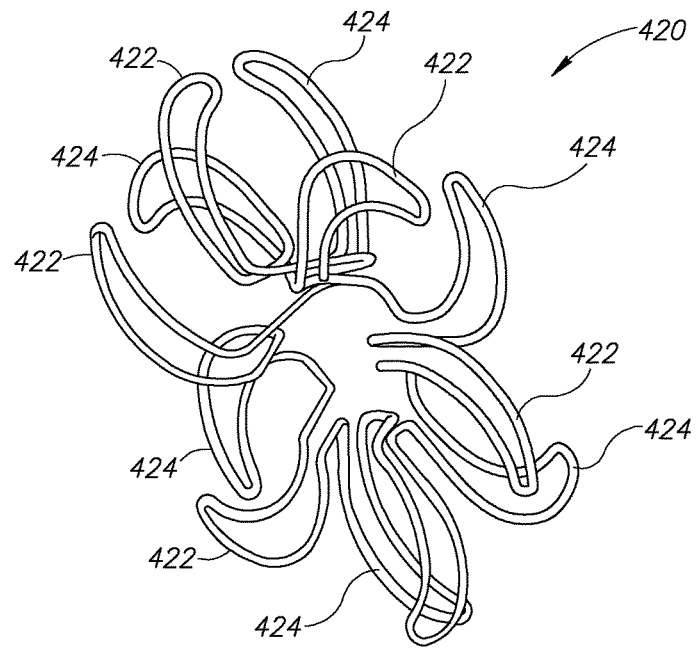

FIG. 2E is a schematic illustration of an anchoring device 420, in accordance with another exemplary embodiment of the invention. Device 420 includes banana shaped petals 422 and 424. As shown, the petals 422 and 424 have distal heads pointing clockwise, from a view directed at the petals in front of the wall. Thus, while the portions of the petals close to central orifice 106 are substantially parallel to each other on opposite sides of the wall, the heads of the petals are not parallel to each other. In some embodiments of the invention, however, the tips of different petals 422 and 424 are parallel each other on opposite sides of the tissue wall. Petals of other shapes, such as hoof shaped with a larger distal portion than proximal portion, may be used.

As with the above described embodiments, the petals 422 may be distributed evenly or unevenly around the central orifice 106. In addition, there may be the same number of petals 422 as petals 424 or there may be different numbers of petals 422 and 424.

Figure 3:
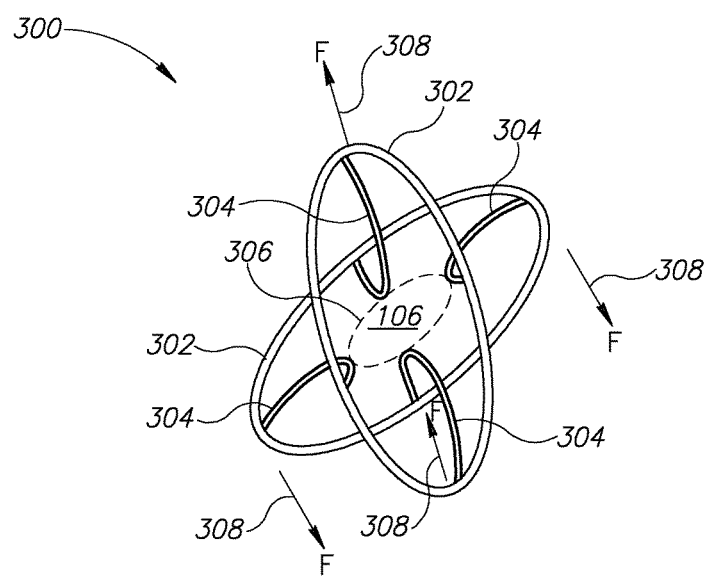
FIG. 3 is a schematic illustration of an implant device, in accordance with another exemplary embodiment of the invention.

FIG. 3 is a schematic illustration of an implant device 300, in accordance with another exemplary embodiment of the invention. Device 300 includes two external rings 302 which are to be located on opposite sides of the wall. A plurality of bands 304 connect between the two rings 302 in a manner which pressures the tissue of the wall to keep the orifice in the wall open. Device 300 is shown with four bands 304, although fewer or more bands may be used. Bands 304 may be formed from the same material as rings 302 or may be formed separately from a metal or plastic. Alternatively, bands 304 my be formed of a fabric, such as Dacron, ePTFE or PolyUrethane strips.

Alternatively or additionally to bands 304, rings 302 may be connected partially or entirely by a sheet of fabric or a mesh.

In some embodiments of the invention, in addition to rings 302, an additional smaller ring 306, which fits into or adjacent orifice 106, is included in device 300.

In some embodiments of the invention, rings 302 are elliptical and the longer axis of one ring 302 is located in a rest state of device 300, against the shorter axis of the second ring 302. This arrangement of rings 302 allows folding of rings 302, by applying pressure along arrows 308, for fitting into a narrow delivery tool, without disturbance between the rings. Alternatively, rings 302 are circular or have any other suitable shape.

FIGS. 1-3 illustrate various embodiments of flat anchoring devices. Combinations and variations of these embodiments may also be used in accordance with the present invention. Further embodiments of anchoring devices are described below, for example with reference to FIGS. 6A and 6B.

Keep Orifice Open

As mentioned above, the above described anchoring devices may be used on their own to keep an orifice open in internal tissue of humans or animals. For example, in some congestive heart failure (CHF) patients it is considered advantageous to perforate a hole between the right and left atria or between other inner chambers. Implanting of one of the above described anchoring devices holds the orifice open, with minimal intervention.

Valve

In some embodiments of the invention, device 100 carries a valve, which regulates the flow through the open orifice.

Figure 4A:
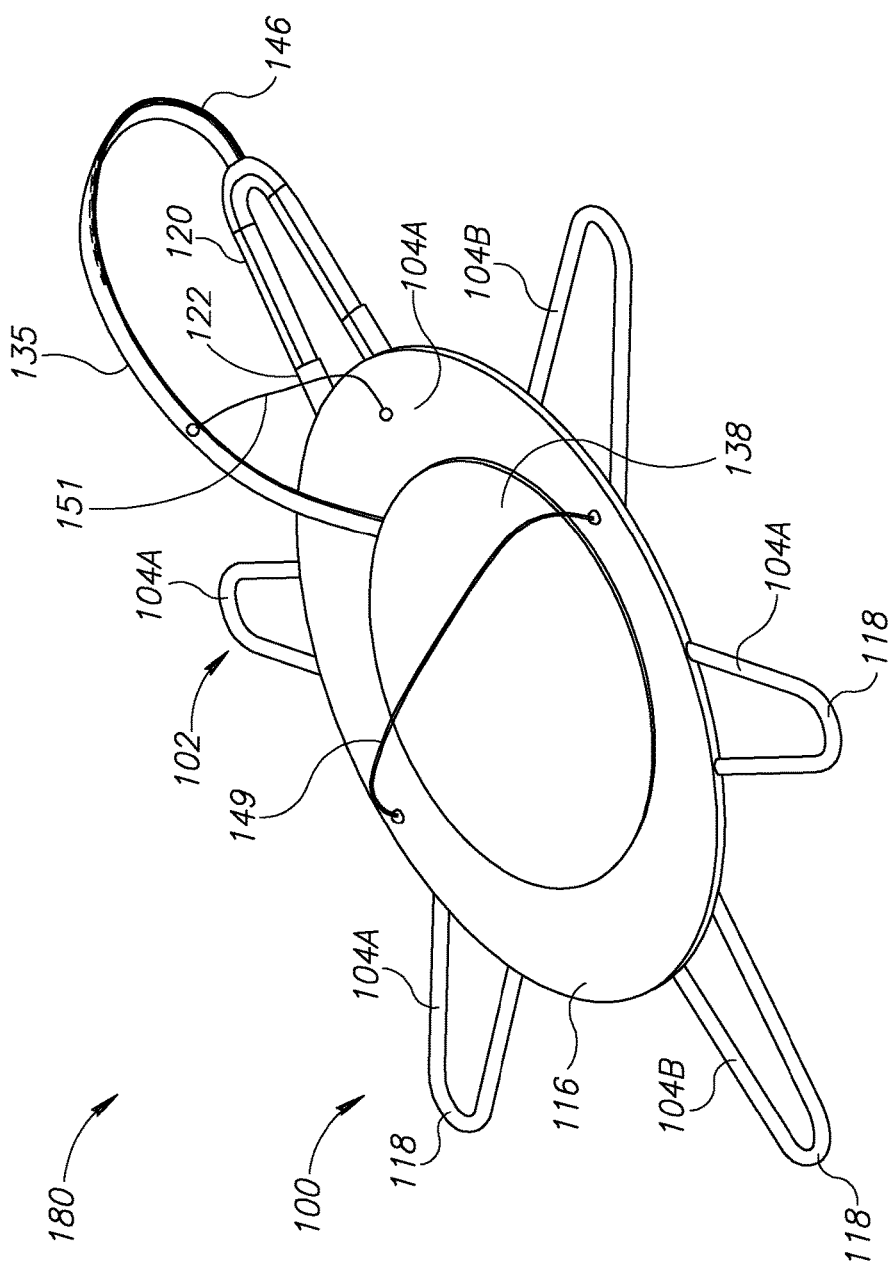
FIG. 4A is a schematic illustration of a valve formed of an anchor device carrying a flap, in accordance with an exemplary embodiment of the invention.

FIG. 4A is a schematic illustration of a valve 180 formed of an anchor device 100 carrying a flap 138, in accordance with an exemplary embodiment of the invention. Flap 138 is mounted on an elastic arm 135 connected to one of petals 104A of anchor device 100. Arm 135 is optionally preconfigured with a bent portion 146 serving as a hinge of flap 138. Arm 135 is adapted to allow flap 138 to shift between a closed state in which flap 138 is adjacent central orifice 106 and an open state in which the flap is distanced from the central orifice and allows flow through the orifice.

In some embodiments of the invention, a skirt 116 is mounted on anchor device 100 in a manner which protects the tissue wall from recurring strikes of flap 138. A wire 149 is positioned above flap 138 in a manner which prevents flap 138 from opening by more than an allowed extent.

Skirt

Skirt 116 optionally has a ring shape which surrounds orifice 106. Alternatively to a round skirt, a polygon shaped skirt may be used, for example having a number of sides equal to the number of petals 104 to which the skirt is to be connected. Use of such a polygon shaped skirt is expected to provide a good attachment of the skirt to device 100, when attached to all the petals intended to be on its side of the wall. Thus, skirt 116 is kept flat, which provides a better contact between skirt 116 and the tissue wall. For example, for a device 100 having three petals 104 on each side of the wall, a triangular skirt may be used. Alternatively, skirt 116 is attached in a manner which allows some slack, such that the skirt may have a wavy form, which could be better in some cases for achieving a desired tissue growth pattern. In some embodiments of the invention, skirt 116 is sufficiently wide and/or thick, optionally, at least 100 microns (e.g. 150 microns) thick, for example to prevent undesired tissue growth thereon and/or to protect against force applied by flap 138. Alternatively, skirt 116 may be thinner and/or be otherwise configured such that the skirt does not protect from force applied by the flap.

In an exemplary embodiment of the invention, skirt 116 is produced by dipping and has a thickness, without wire 102, of between about 180-300 microns (e.g., 200 microns). For implanting in the septum, skirt 116 optionally has an outer diameter including the central orifice 106 of at least 0.5 centimeters, 1 centimeter or even at least 1.3 centimeters. Optionally, skirt 116 does not extend up to central orifice 106, under an assumption that this may prevent additional obstruction of orifice 106 due to the edges of the skirt. In some embodiments of the invention, in accordance with this option, the inner edges of skirt 116 are distanced from the central orifice by at least 1 millimeter or even at least 2 or 3 millimeters. Alternatively, the inner edges of the skirt reach up to central orifice 106. Further alternatively or additionally, skirt 116 has soft and/or sharp edges to avoid tissue growth.

In embodiments in which device 100 is implanted in the wall between the left and right atria, the skirt is optionally located in the right atrium, which has lower pressures and is less disturbed by such an implant. In other embodiments of the invention, device 100 includes two skirts, for both sides of the wall on which device 100 is mounted.

In an exemplary embodiment of the invention, skirt 116 is produced from the same material as wire 102. In some embodiments of the invention, skirt 116 and wire 102 are produced together as a single piece, for example in an etching process from a single tube or sheet. In the etching process, different elements are optionally given different thickness. For example, petals 104 may be made relatively thick, while skirt 116, arm 135 and/or flap 138 are made thinner with the same or different thicknesses.

Alternatively, skirt 116 and/or flap 138 are produced in a deposit process. For example, skirt 116 is optionally produced by depositing a material on wire 102. In some embodiments of the invention, skirt 116 is formed of nitinol, a suitable polymer or of cloth (e.g., Dacron). Alternatively or additionally, skirt 116 comprises polyurethane (PU) and/or ePTFE. Skirt 116 and/or flap 138 may be produced using any method known in the art, including the methods described in U.S. Pat. No. 7,018,408 to Bailey et al., issued Mar. 28, 2006 and US patent publication 2006/0116751 to Bayle et al., the disclosures of which documents are incorporated herein by reference.

In another embodiment of the invention, skirt 116 is manufactured using a dipping and brushing technique. Optionally, a first skirt layer is dipped on a designated shaped mandrel. After a partial curing process, the petals 104 on the side of skirt 116 are held against the partially cured surface and additional layers of the polymer are applied by brushing to obtain full and smooth embedding of the petals in the skirt.

In some embodiments of the invention, skirt 116 comprises two layers formed of different materials, that are bonded together using any of the methods known in the art. One layer intended to face the wall is rough and/or is otherwise adapted to induce tissue growth and the other layer is optionally smooth and/or anti-thrombosis.

As shown, petals 104B are embedded within skirt 116. In other embodiments of the invention, skirt 116 is mounted on petals 104A on the opposite side from petals 104B. In still other embodiments of the invention, skirt 116 is located between petals 104A and 104B.

Any suitable method may be used to attach skirt 116 to petals 104A. In some embodiments of the invention, an adhesive is used to connect skirt 116 to wire 102. Optionally, micro pores are drilled in skirt 116 at the expected connection points using a laser, in order to increase the effectiveness of the adhesive. In some embodiments of the invention, wire 102 is woven through skirt 116, which is made in these embodiments of a suitable material to allow weaving therethrough (e.g., ePTFE). In another embodiment of the invention, skirt 116 is formed from two layers, the two layers are attached to each other with petals 104A between them. In other embodiments of the invention, skirt 116 is made of a metal and is welded, crimped or soldered to petals 104A.

In some embodiments of the invention, skirt 116 is a substantially solid flat surface. Alternatively, in order to minimize the amount of material, skirt 116 partially or entirely comprises a mesh.

While skirt 116 is described for use with flap 138, in other embodiments of the invention an anchoring device not carrying a valve carries skirt 116 to protect the tissue wall for other reasons, for example to prevent or induce tissue growth. In other embodiments of the invention, flap 138 is used without skirt 116, for example when the anchoring device 380 of FIG. 2D is used. Ring 382 of device 380 optionally has sharp edges, in embodiments in which flap 138 is mounted thereon, in order to prevent tissue growth on the ring.

Figure 4B:
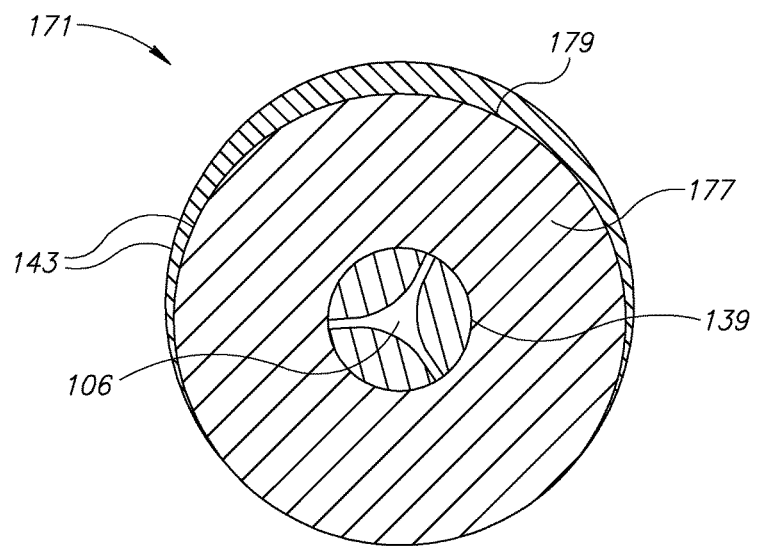
FIG. 4B is a schematic illustration of an anchor device, in accordance with an exemplary embodiment of the invention.

FIG. 4B is a schematic illustration of an anchor device 171, in accordance with another exemplary embodiment of the invention. In anchor device 171, rather than limiting the amount of material in the anchoring device to a minimum, two large skirts 177 and 179 connected together at a circle 139 surrounding orifice 106, are used. Skirts 177 and 179 are formed of a flexible material which allows minimally invasive delivery. In some embodiments of the invention, skirts 177 and 179 are reinforced by external rings 143 and optionally an internal ring at circle 139. Alternatively or additionally, other reinforcement structures are used, for example device 100 or any of the other anchoring devices described above. Inner circle 139 optionally has a diameter of at least 3, 5 or even at least 8 millimeters. In an exemplary embodiment of the invention, inner circle 139 has a diameter of about 10 millimeters and external rings 143 have a diameter of about 25 millimeters. Other dimensions may also be used.

The use of the embodiment of FIG. 4B is particularly useful when the wall in which the anchor device is embedded is weak and requires extra protection. Optionally, the inner surfaces of skirts 177 and 179 which face each other are coated with a growth enhancing coating which induces tissue growth and enhances the bond of the implant to the wall.

Skirt and Flap Coating

As discussed above regarding wire 102, skirt 116 is optionally coated on its surface intended to face the wall, with a drug which has desired therapeutic characteristics, such as an anti-inflammatory drug. Alternatively or additionally, skirt 116 is made rough or from a highly porous material on its face intended to be directed to the wall, in order to encourage tissue growth and/or better attach to the wall tissue.

In some embodiments of the invention, both skirt 116 and wire 102 are treated using the same materials and/or application techniques. Alternatively, wire 102 and/or areas of skirt 116 and wire 102 which are subject to high friction and/or extensive surface strain are treated with a porous polymer which endures such strain and friction, while other areas, such as the flat areas of skirt 106 are coated by a fractal coating.

The other face of skirt 116 is optionally made of a low porous material, optionally sealed or otherwise smooth, to prevent tissue growth thereon and/or adhesion of the flap to the skirt, flap failure or formation of clots. Alternatively, the face of skirt 116 not facing the wall is also coated to some extent, in order to form at least a partial barrier between the skirt and blood flow, in order to reduce coagulation. In some embodiments of the invention, the coating on the face of skirt 116 not facing the wall less induces tissue growth compared to the coating on the other face.

In some embodiments of the invention, one or more surface of skirt 116 is coated with an anti-inflammatory drug, like steroid to prevent inflammation formation, which may encourage tissue growth. Optionally, this layer is covered with blood diluting drugs, like heparin, to prevent formation of clotting. The release of the drugs may be immediate or slow for a short period of less than an hour, or for a long period of more than an hour, several days, more than two weeks or more.

Optionally, flap 138 is not coated to prevent tissue growth, for example in those embodiments in which it is in movement. Alternatively, for example in embodiments in which flap 138 only moves under special conditions, flap 138 is partially or entirely coated to prevent tissue growth. In some embodiments of the invention, skirt 116, arm 135 and/or flap 138 are covered by a thin ePTFE cover to improve their hemocompatibility.

In some embodiments of the invention in which a ring or other portion of the anchoring device defines the orifice, as illustrated in FIG. 2D, the ring may have a sharp edge in the direction facing the flap 138, in order to prevent tissue growth on the ring.

In some embodiments of the invention, flap 138 has a balloon mounted on its surface facing orifice 106. Optionally, the balloon is inflated before insertion into the patient. Alternatively, the balloon is inflated using the delivery tool used in delivering the flap into the patient. Further alternatively or additionally, the balloon is inflated by an osmotic gradient method. The inflated balloon may provide a better sealing of orifice 106 and/or cushion the repeated forces of flap 138 against skirt 116 or the tissue wall behind.

Flap and Arm

In some embodiments of the invention, the opening and closing of flap 138 depend on the relative pressure between the opposite sides of the wall on which valve 180 is mounted. The pressure required in order to open flap 138 is optionally selected according to the task of device 180 and is set, for example, by controlling hinge 146 and/or the elasticity of arm 135. Alternatively or additionally, the opening pressure of flap 138 is controlled by selecting a desired size of the flap, a suitable material from which the flap is manufactured, the length of arm 135 (i.e., a longer arm opens at lower pressure) and the width of the arm. In some embodiments of the invention, the opening pressure of valve 180 is set by setting the extent of preload of the flap 138, e.g., the amount of force applied by the flap against anchor device 100 in its rest state.

In some embodiments of the invention, flap 138 comprises a plastic or nitinol sheet cut into shape. The use of nitinol adds to viewability by medical imaging modalities such as fluoroscopy. In addition, nitinol has a high endurance to movements and can withstand large reoccurrences of opening and closing of flap 138, without suffering from substantial fatigue. Nitinol may also facilitate a monolithic design, optionally made from a sheet of the material.

It is noted, that other materials may also be used, optionally with miniature radio opaque markers to allow visibility in medical imaging methods. Such materials optionally have similar properties as nitinol, although not necessarily the same.

Alternatively, flap 138 comprises a metal (e.g., nitinol) frame, with a plastic or other material sheet held, optionally in tension, by the frame. The plastic or other material sheet may be rigid, flexible or elastic. In some embodiments of the invention, flap 138 is formed from the same material as wire 102 optionally being produced from a same sheet (e.g., foil), for example using an etching procedure. The thickness of flap 138 is optionally selected according to a desired stiffness of the flap. In some embodiments of the invention, flap 138 has a thickness of less than 100 microns, less than 60 microns or even less than 40 microns (e.g., 30 microns). Alternatively, flap 138 may have a thickness above 50 microns or even above 100 microns.

The length of arm 135 from the perimeter of flap 138 to a maximal curvature point of hinge 146 is optionally at least 0.5 millimeters, at least 3 millimeters or even at least 5 millimeters. In some embodiments of the invention, the length of arm 135 from the perimeter of flap 138 to the maximal curvature point of hinge 146 is at least greater than half the diameter of flap 138 or is even greater than the diameter of flap 138.

The maximal curvature point of hinge 146 is located, in some embodiments of the invention, beyond the outer perimeter of anchor device 100 in its flat deployed state. Optionally, in these embodiments, the maximal curvature point of hinge 146 is at least 0.5 millimeters, at least 3 millimeters or even at least 5 millimeters beyond the outer perimeter of anchor device 100.

In some embodiments of the invention, flap 138 and arm 135 are formed as a single piece of the same material, for example nitinol or a suitable polymer. Alternatively, flap 138 and arm 135 may be formed of separate pieces, possibly from different materials.

Alternatively to being connected to an end of a petal 104A, arm 135 may be connected to skirt 116. Further alternatively, instead of mounting flap 138 on an elastic arm, flap 138 is mounted on a pin hinge which rotates in a pin housing. Optionally, in accordance with this alternative, a spring of any suitable type is used to close the flap after it is opened.

In some embodiments of the invention, when the condition governing the opening of flap 138 is met, it opens to a specific extent, regardless of the pressure difference (i.e., pressure gradient) between its opposite sides or the conditions that caused it to open. Alternatively, the extent of opening of flap 138 depends on the pressure between the opposite sides of device 180. In some embodiments of the invention, the extent of opening increases linearly with the pressure, from a minimal pressure for which flap 138 opens to a pressure corresponding to a maximal opening extent of flap 138. Alternatively, the opening extent of flap 138 is a non-linear function of the pressure on its opposite sides. In some embodiments of the invention, a spiral spring is connected to arm 135 to govern the opening of flap 138. The spiral spring is optionally designed to allow opening to a small extent at low pressure levels but requiring very high pressure, which generally are never reached for large opening extents.

In the maximal opening extent of flap 138, the flap is optionally at an angle of less than 30°, 20°, or even less than 10° relative to the surface containing petals 104. Optionally, in the maximal opening extent, flap 138 is at an angle of at least 5° relative to the surface containing petals 104, for example 9°. The strain on arm 135 optionally does not exceed 0.5% or even does not exceed 0.3%, in order to avoid wear due to fatigue.

Optionally, in its maximally open state, the projection of flap 138 on central orifice 106 covers at least 50% or even at least 75% of the orifice. In some embodiments of the invention, at its maximal opening, the area of a surface between the tissue wall and the flap is about equal to the area of central orifice 106, allowing maximal flow. Accordingly, for example, the distance (H) from the farthest edge of flap 138 to the tissue wall, in the open state, is optionally substantially equal to a quarter of the diameter of the orifice in the wall. Alternatively or additionally, the maximal opening extent of flap 138 is selected to be small enough such that it allows a substantially infinite number of openings of the valve without causing arm 135 to break.

In some embodiments of the invention, in the maximal opening state, the rate of flow of blood through central orifice 106 is less than 2000 cc/min, less than 1500 cc/min or even less than 1000 cc/min in order to enable a sufficient amount of blood to go through other paths even when flap 138 is purposely and/or inadvertently maximally open. The blood flow rate through orifice 106 is optionally selected to achieve a required pressure drop while maintaining a required cardiac output level.

In an exemplary embodiment of the invention, when device 180 is placed in the wall between the left atrium and the right atrium, flap 138 is designed to open when the pressure gradient is above a predetermined value, which is not encountered during a normal cardiac cycle of a healthy patient. The opening is optionally designed to pass a sufficient amount of blood from the left atrium to the right atrium in order to alleviate high pressures associated with CHF.

Alternatively, flap 138 is designed to open at lower pressures, even pressures encountered during the normal cardiac cycle of the patient. Optionally, in this alternative, the opening at the lower pressure is for a short duration and/or to a small extent, so that only a small amount of blood passes through the orifice under normal conditions. The opening of flap 138 under normal conditions is considered advantageous as it prevents clotting, but does not have a substantial effect on the patient's cardiac output and/or chambers loading or otherwise on the patient's blood flow.

In some embodiments of the invention, flap 138 opens, when the pressure in the left chamber is greater than in the right chamber, even when there is only a small pressure gradient between the sides of the wall. In other embodiments of the invention, flap 138 is preloaded, such that it only opens when the pressure gradient is greater than zero, for example at least 1 mmHg, at least 3 mmHg or even about 6 mmHg. In some embodiments of the invention, flap 138 is preloaded to open only in response to high pressures, for example pressures above 12 mmHg or even 15 mmHg. Other pressure thresholds may be used according to the characteristics of the specific patient in which device 180 is implanted. In some embodiments of the invention, flap 138 is produced preloaded with a predetermined pressure by pulling flap 138 below skirt 116 at the time of setting the rest state of flap 138.

The pressure gradient at which flap 138 opens to its maximal extent, may be as low as 1 or 2 mmHg or lower, or may be higher, for example at least 5 mmHg, at least 7 mmHg or even at least 10 mmHg. In an exemplary embodiment of the invention, flap 138 opens to its maximal extent at a pressure gradient of about 12 mmHg.

In some embodiments of the invention, flap 138 has a slow opening response time, such that flap 138 opens only when the required opening pressure occurs for at least a minimal time, thus avoiding opening due to sporadic short term pressure peaks or pressure peaks occurring for short periods during the cardiac cycle. Alternatively, flap 138 has a fast response time which is faster than the heart pulse of the patient, for example less than 100 ms, or even less than 30 milliseconds, such that the valve will open for short periods at frequent pressure spike occasions. In accordance with this alternative, the frequent opening of flap 138 is considered advantageous in order to prevent clotting. In an exemplary embodiment of the invention, flap 138 has a response rate of about 30 Hz. Optionally, in these embodiments, flap 138 opens frequently, e.g., every cardiac cycle, for a short period of less than 100 milliseconds or even less than 60 milliseconds, for example about 30 milliseconds. In some of these embodiments of the invention, flap 138 is adapted to allow flow of between 400-600 cc/min, at times in which flap 138 is considered in a closed state, i.e., the heart is not subject to high pressures and the flap only opens for short periods. In some embodiments of the invention, flap 138 has a fast closing rate, e.g., less than 15 milliseconds, in order to prevent back flow in the wrong direction. Flap 138 optionally has a very low mass and/or spring constant in order to achieve the fast response time.

Optionally, when the pressures in the heart are normal, no more than 1200 cc/min, no more than 800 cc/min, possibly no more than 600 cc/min or even less than 400 cc/min is allowed to pass through central orifice 106. In an exemplary embodiment of the invention, about 600 cc/min is allowed to flow through central orifice 106 under normal conditions. In other embodiments, smaller amounts of blood are allowed to flow through the orifice under normal conditions, for example between 200-300 cc/min.

Alternatively or additionally to setting the opening profile of flap 138 to allow passage of a relatively small amount of blood through orifice 106 under normal conditions, flap 138 is kept slightly open by, for example, having an orifice or slit in flap 138 and/or by having flap 138 not close completely against orifice 106.

Figure 4C:
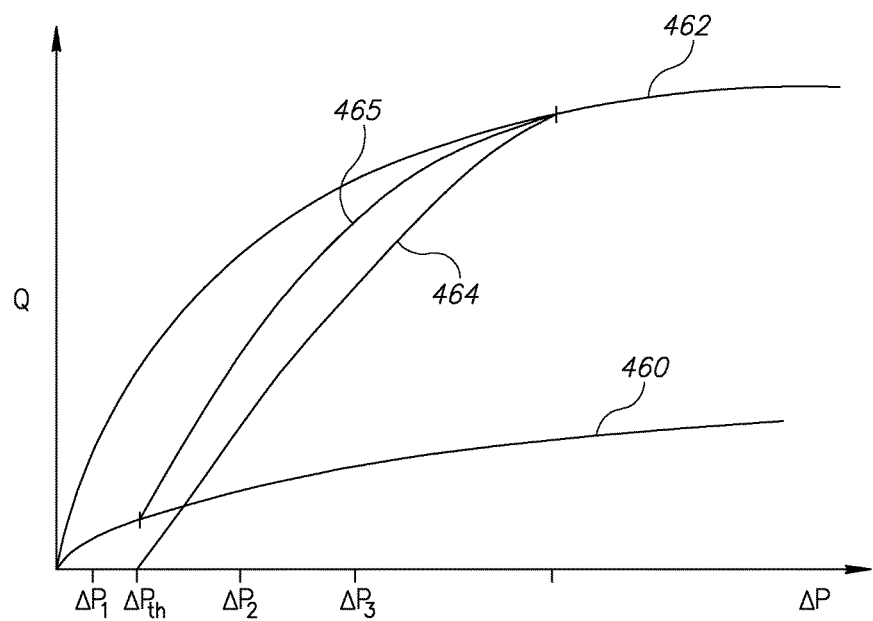
FIG. 4C is a schematic graph of operation schemes of a valve, in accordance with various exemplary embodiments of the invention.

FIG. 4C is a graph which shows the correlation between the pressure on flap 138 and the amount of blood shunting through orifice 106, in accordance with various exemplary embodiments of the invention. A first line 460 shows the flow through orifice 106 when flap 138 is fixed in a substantially closed state in which it leaves only a small opening for blood flow. This may be achieved, for example, by having a stopper keep flap 138 always slightly open or have a small window in flap 138, which allows continuous shunting of blood even when flap 138 is closed. As can be seen, as the pressure gradient ($\Delta P$) between the chambers on the opposite sides of the wall in which anchor 100 increases, the flow through the orifice moderately increases.

Line 462 represents the flow through orifice 106 when flap 138 is held maximally opened regardless of the pressure gradient between the chambers on opposite sides of the wall.

In some embodiments of the invention, flap 138 is set to open only when the pressure gradient $\Delta P$ is greater than a threshold value $\Delta P_{th}$. Line 464 represents the blood flow through orifice 106, in one of these embodiments, in which flap 138 entirely closes orifice 106 and line 465 represents the blood flow in another of these embodiments, in which flap 138 does not entirely prevent blood flow in its closed state.

The slopes of lines 464 and 465 are determined by the spring rigidity of flap 138. When the spring constant is low, flap 138 is easily opened and the lines have a steep slope. In some embodiments of the invention, when it is desired to open flap 138 maximally when the pressure on the flap is above threshold value $\Delta P_{th}$, arm 135 has a very low spring constant. In contrast, in some embodiments of the invention, a high spring constant is used, which in the graph of FIG. 4C is represented by a non-steep slope.

The structure of device 100 and flap 138 (FIG. 4A) mounted thereon is optionally used to adjust the threshold value $\Delta P_{th}$, for example by setting the preload extent of flap 138 and/or by adding a spring which adds to the pressure required in order to open flap 138. In addition, the structure of device 100 and flap 138 may be controlled in order to set a maximal opening extent of flap 138, for example by adding a non linear spring, e.g., a spiral spring, which makes the pressure required to exceed a predetermined opening extent, very high.

In some embodiments of the invention, threshold value $\Delta P_{th}$ is set sufficiently high in order that flap 138 opens only when pressure levels above those normally encountered in healthy patients during the cardiac cycle are encountered. Optionally, in accordance with these embodiments line 465 is used, such that blood regularly shunts through orifice 106 and prevents coagulation. Optionally, in accordance with these embodiments, threshold value $\Delta P_{th}$ is set to above 8 mmHg or even above 10 mmHg.

In other embodiments of the invention, threshold value $\Delta P_{th}$ is set relatively low, such that flap 138 opens in substantially every cardiac cycle. For example, under normal conditions, the pressure during the cardiac cycle varies between $\Delta P_1$ and $\Delta P_2$ allowing passage of blood at a rate of between 300-600 milliliters per minute. When, however, the patient suffers from left atrial excess blood pressure levels, the pressure varies between $\Delta P_1$ and $\Delta P_3$ allowing shunting of blood at a rate of between 800-1200 milliliters per minute. Optionally, in accordance with these embodiments, threshold value $\Delta P_{th}$ is set to below 7 mmHg or even below 6 or 5 mmHg.

In some embodiments of the invention, a physician treating a CHF patient selects a valve with a desired threshold value according to a state of the patient. Optionally, in a patient in which there is an expectance of reoccurrence of high pressures even after the pressures are reduced to a desired level, a valve with a low pressure threshold, for example less than 7 mmHg is used, so that the valve will open periodically even when the patient does not suffer from high pressures. Alternatively, when it is desired that the valve permanently close when the pressures go down, a valve with a high pressure threshold (e.g., above 7 or even above 9 mmHg) is used.

In some embodiments of the invention, flap 138 has a fast response time, which is much shorter than the cardiac cycle of patients. For example, the response time of flap 138 is optionally shorter than 100 milliseconds or is even shorter than 50 milliseconds. In accordance with these embodiments, threshold value $\Delta P_{th}$ is selected such that the average pressure difference in a healthy patient is below the threshold, but during the cardiac cycle the pressure reaches above the threshold. Due to the short response time, flap 138 opens during a partial portion of the cardiac cycle and thus provides washout of orifice 106.

In other embodiments of the invention, flap 138 has a slow response time of close to the length of a single cycle of the cardiac cycle. In these embodiments, threshold value $\Delta P_{th}$ is optionally selected to be above the average pressure during the cardiac cycle of a normal patient, such that the valve opens only when the patient suffers from a high pressure difference. Optionally, in accordance with these embodiments, flap 138 is held constantly slightly open or has a small window, which allows washout of the orifice 106. Optionally, in these embodiments, constant leakage due to a small opening can be used to assure proper washout of the orifice.

Alternatively, threshold value $\Delta P_{th}$ is set to be slightly below the average pressure between the right and left atrium in a healthy patient. Thus, flap 138 regularly opens during the cardiac cycle in healthy patients, but only small amounts of blood shunt through orifice 106 when the flap opens, because the opening extent is small. When, however, the patient suffers from a high pressure difference, flap 138 opens to a greater extent and allows passage of large amounts of blood.

Restriction Wire

Wire 149 (FIG. 4A) is optionally connected between two points on skirt 116. Alternatively or additionally, wire 149 may be connected between two of petals 104B. Wire 149 optionally prevents flap 138 from opening by more than an allowed extent, in order to prevent too much blood from passing through orifice 106 and/or in order to prevent stressing arm 135. Wire 149 optionally comprises Kevlar, nitinol or any other suitable biocompatible material.

Alternatively or additionally to wire 149, a string 151 connects skirt 116 or a petal 104B to arm 135 in a manner which restricts the maximal opening extent of flap 138.

Alternatively to a restriction wire, a restriction string, sheet or tab may be used.

Another Flap Embodiment

Figure 5:
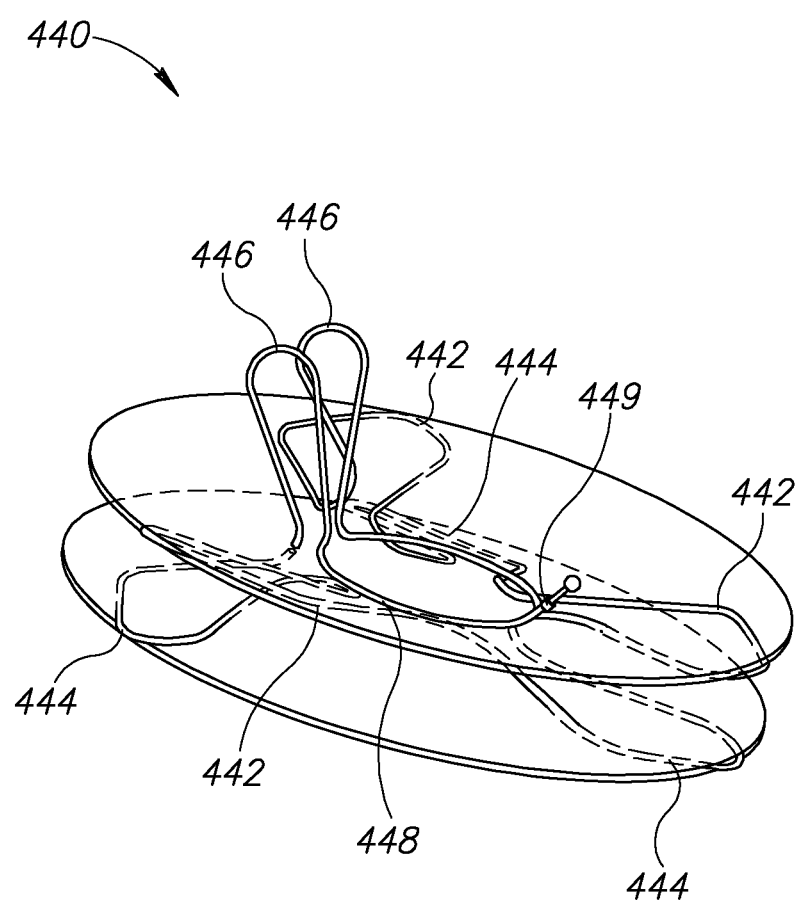
FIG. 5 is a schematic illustration of a flap valve, in accordance with another exemplary embodiment of the invention.

FIG. 5 is a schematic illustration of a flap valve 440, in accordance with another exemplary embodiment of the invention. Valve 440 comprises three petals 442 for one side of the tissue wall and three petals 444 for the other side of the wall. The petals have a non-symmetric shape, and are arranged such that they partially overlap on opposite sides of the wall, increasing the pressure applied on the wall. A flap 448, shown as being formed from a frame and internal sheet, is held by a pair of holders 446 which extend substantially perpendicular to orifice 106. A handle 449 is optionally used in delivery of valve 440 into the patient and/or removal of valve 440 from within the patient.

Alternatively to holders 446 extending substantially perpendicular to flap 448 at the point of their connection in the closed state, holders 446 may be connected at a smaller angle, optionally an angle of at least 30°, at least 45° or even at least 60°.

In other embodiments of the invention, a flap connects to its arm or handle at an angle of less than 30°, less than 20° or even less than 10°.

Other Valves

Although the single flap valve described above has many advantages, the present invention is not limited to any specific valve, and anchor device 100 as well as other embodiments of the present invention may be used with other types of valves, such as a duck valve, a bi-leaflet valve, a tri-leaflet valve and/or a parachute shaped valve. For example, for a leaflet valve, a short tube, with the valve therein, is optionally mounted on device 100 with the central axis of the short tube covering central orifice 106.

Figure 6A:
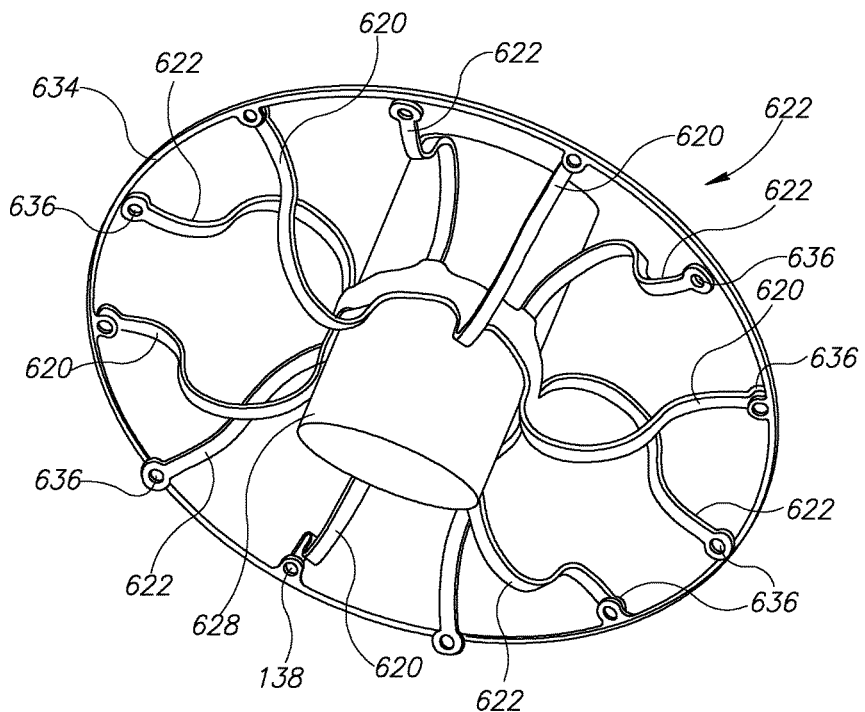
FIGS. 6A and 6B illustrate an anchoring device, carrying a shunt, in a deployed state and collapsed state, respectively, in accordance with an exemplary embodiment of the invention.
Figure 6B:
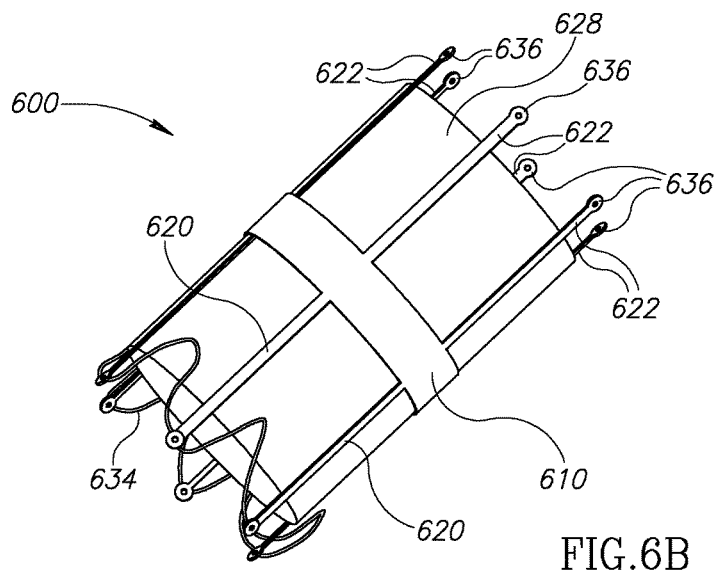

FIGS. 6A and 6B illustrate an anchoring device 600, carrying a shunt 628, in accordance with an exemplary embodiment of the invention. Anchoring device 600 includes a ring 610, which carries shunt 628. A plurality of bent arms 620 and 622 which are adapted to clamp between them a tissue wall. Optionally, arms 620 and/or 622 include loop elements 636 at their distal ends. Loop elements 636 provide an attachment mechanism for a delivery system, and also allow for reattaching the arms to the delivery system during a removal or other procedure, if necessary. Loop elements 636 optionally also increase the area enduring the force applied by the arms to the wall tissue and may further help to anchor device 600 in place by incorporating scar tissue within the loop area and over a greater surface area.

In some embodiments of the invention, a circumferential connecting wire 634 connects to arms 620 forcing the arms 620 to move together and thus prevent arms from falling to an opposite side of the wall, as well as to prevent arm entanglement and/or unintentional premature release of one or multiple arms, in release of anchoring device 600. Alternatively or additionally, wire 634 provides structural stability to the distal portion of device 600. For example, wire 634 optionally prevents one or more of arms 620 from applying excess force against the tissue wall and if necessary prevents one of the arms from migrating through the wall, to the other side of the wall. Optionally, wire 634 may be used to collapse arms 620 back into their folded state, for example if a release of the arms was not successful and it is desired to perform the release a second time.

Wire 634 is optionally formed from an elastic material, such as nitinol or a polymeric material.

Alternatively to including a single loop element 636 at its distal end, some or all of arms 620 and/or 622 may include a plurality (e.g., two) of loops at their distal end. Two loops may be used for example to pass wire 634 through both the loops. Loops 636 may be of substantially any suitable size, optionally having an outer diameter between 1-10 millimeters.

Further alternatively or additionally, some or all of arms 620 are connected to wire 634 using any other connection method, for example, permanently connecting (e.g., welding) arms 620 to wire 634. Wire 634 may be connected permanently to arms 620, or may be connected releasably (e.g., using snaps and/or adhesion), for example, allowing removal of wire 634 after device 600 is anchored on the tissue wall.

The number of arms in device 600 is optionally in accordance with any of the embodiments described above regarding petals 104 in device 100. It is noted, however, that more arms may be required than petals, due to the fact that the petals may be viewed as double arms. FIG. 6A illustrates 12 arms, six arms on each side of the device, but more or fewer arms may be used.

During delivery, device 600 is optionally led into the patient held in the orientation shown in FIG. 6B, by channel 500 (FIG. 14C), a delivery tool, or any other mechanism. When properly positioned, the device is gradually or at once released and device 600 assumes its natural state shown in FIG. 6A, engaging the tissue wall. Optionally, in the collapsed state of FIG. 6B, device 600 and shunt 628 can fit into a tube of a diameter of less than 24 French, optionally even not more than 18 or 15 French.

In some embodiments of the invention, shunt 628 comprises a same material as anchor device 600 on which it is mounted. Possibly, anchor device 600 and shunt 628 are formed from a single sheet or tube of material using cutting or etching.

While shunt 628 is described in conjunction with anchoring device 600, it is to be understood that it may be mounted on, or produced with, any of the other anchoring devices described herein.

Shunt 628 optionally comprises a valve, which regulates the flow of blood through the shunt. The valve of shunt 628 may operate in accordance with any of the opening schemes described above regarding flap 138 and/or any other opening schemes known in the art. Substantially any type of valve known in the art may be used, including both active and passive valves, for example, a disc attached to a spring, or a leaf opening. Examples of valves and operation patterns which may be used are described more fully in U.S. Patent publication US 2002/0173742, filed Apr. 20, 2001, in U.S. Provisional application 60/573,378, filed May 24, 2004, and in U.S. Patent Publication US 2005/0148925, filed Jul. 7, 2005, the disclosures of all of which are incorporated herein by reference in their entireties.

Figure 7A:
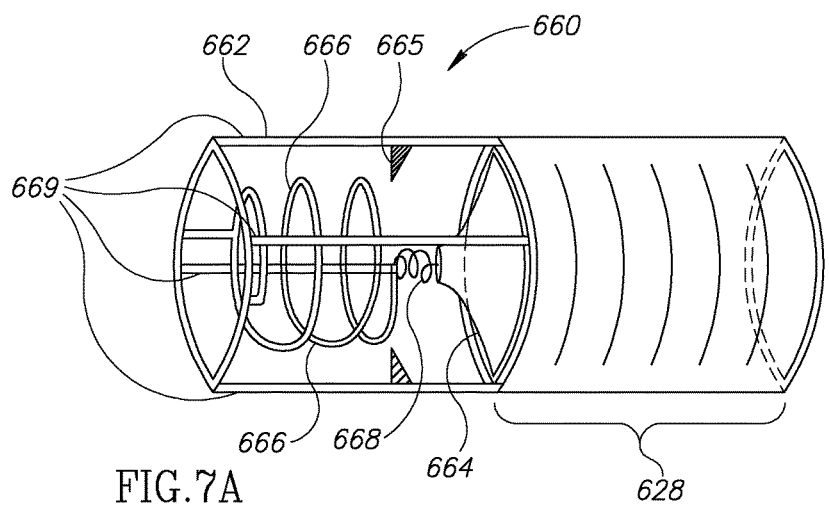
FIGS. 7A-7C describe a two stage valve, in accordance with an exemplary embodiment of the invention.
Figure 7B:
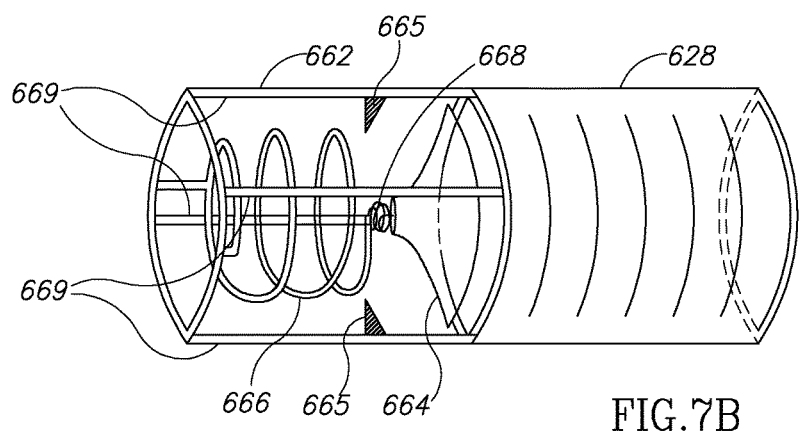
Figure 7C:
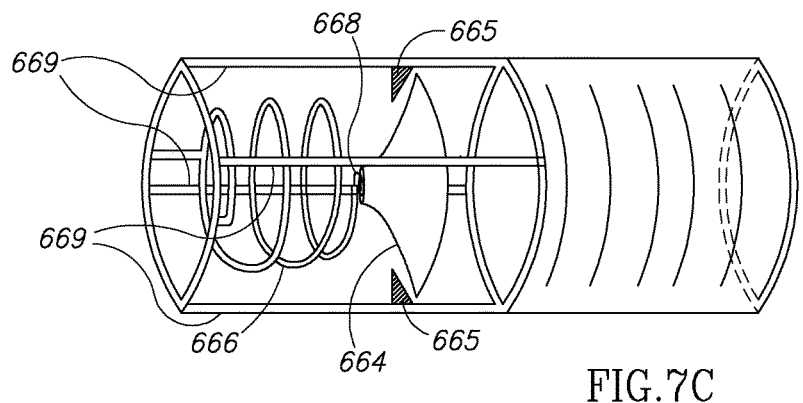

FIGS. 7A-7C describe a valve 660, which is mounted on shunt 628, in accordance with an exemplary embodiment of the invention. Valve 660 comprises a frame 662, which supports a shunt cover 664 mounted on the frame through a pair of springs 666 and 668. A stopper 665 optionally prevents spring 666 from expanding toward cover 664 and compressing spring 668. Absent pressure through shunt 628 onto cover 664, cover 664 entirely prevents flow of blood through the shunt. Alternatively, cover 664 in the closed state only allows passage of a small blood volume. When, however, the pressure increases to above a first threshold, spring 668, collapses, opening a small blood passage, as shown in FIG. 7B. Optionally, when spring 668 is collapsed, blood at a rate of between about 300-600 milliliters per minute can pass through shunt 628. Alternatively or additionally, the collapse of spring 668 moves cover 664 away from the edge of shunt 628 by less than 2 millimeters, less than 1 millimeter or even not more than 0.5 millimeters. If the pressure increases to above a second threshold, higher than the first threshold, also spring 666 gives way, as shown in FIG. 7C, allowing cover 664 to move farther from shunt 628 and allowing a much larger amount of blood to pass through the shunt. Optionally, the collapse of spring 666 allows cover 664 to move at least 3 millimeters, at least 5 millimeters or even at least 7 millimeters away from the edge of shunt 628. In some embodiments of the invention, the compressing of spring 666 allows cover 664 to move between 9-12 millimeters away from the edge of shunt 628.

In some embodiments of the invention, the force required to compress spring 668 is selected to be lower than the peak pressure during a normal cardiac cycle of the patient in which shunt 628 is implanted, such that in substantially every cardiac cycle cover 664 opens and allows flow of a small amount of blood which is believed to prevent blood clotting in shunt 628. Spring 666 is optionally selected, on the other hand, to require a pressure above the highest pressure normally appearing in the cardiac cycle, such that spring 666 is compressed only at clinically high pressures, such as occurring in CHF patients. Optionally, for each patient, a specific shunt 628 is selected from a plurality of shunts having springs of different force profiles, according to the patients specific characteristics.

Alternatively to only two springs, valve 660 may include three or even more springs, in order to implement a more complex opening profile.

Frame 662 is shown as including four support members 669 but may include more or fewer members or may be replaced by any other structure, such as a net.

Figure 8A:
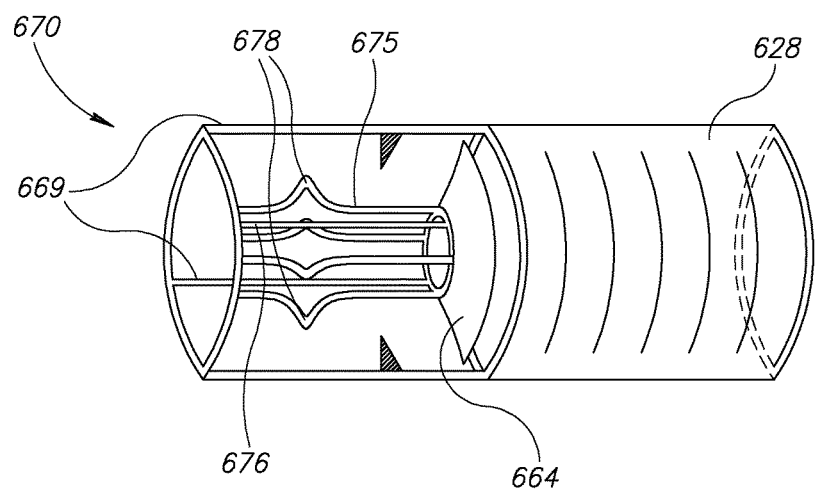
FIG. 8A is a schematic illustration of a valve, in accordance with another exemplary embodiment of the invention.

FIG. 8A is a schematic illustration of a valve 670, in accordance with an exemplary embodiment of the invention. In valve 670, the coil springs 666 and 668 of valve 660 are replaced by one or more thin springy elements 676 and a springy tube 675, which is compressed at protruding portions 678 only under high pressures. Thin springy elements 676 have a fraction of the thickness of springy tube 675, for example between 0.3 to 0.5 of the thickness. Springy tube 675 and thin springy elements 676 are optionally comprised of Nitinol or another shape memory alloy. Thin springy elements 676 are optionally bendable up to 90 degrees, and require less force for bending than protruding portions 678 of springy tube 675. Under low pressures, springy elements 676 give way and allow passage of a small amount of blood. Under high pressures, springy tube 675 collapses and gives way for larger amounts of blood.

Figure 8B:
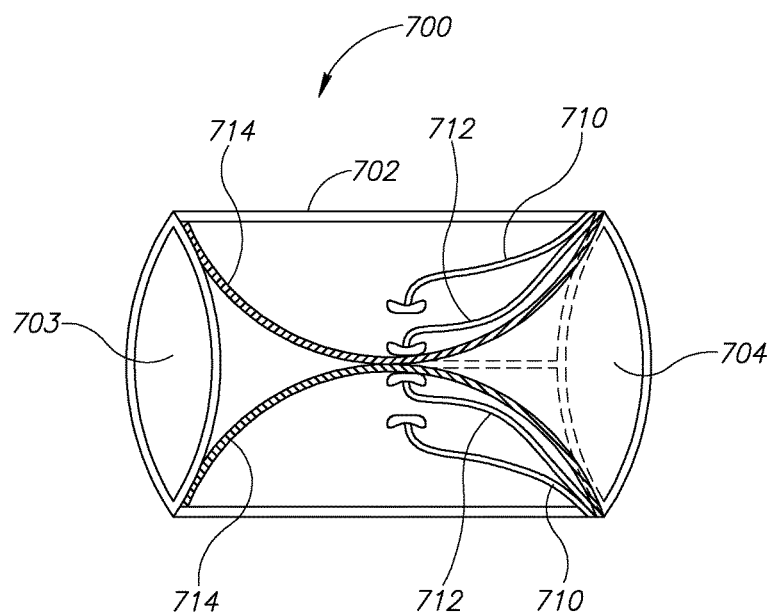
FIG. 8B is a schematic illustration of a shunt, in accordance with an embodiment of the present invention.

FIG. 8B is a schematic illustration of a shunt 700 in accordance with another embodiment of the present invention. Shunt 700 includes a frame 702 and an inner membrane 714. Membrane 714 is comprised of flexible material, such as Dacron. Frame 702 is open at a proximal end 703 and a distal end 704, but membrane 714 can be compressed and block flow of fluid through shunt 700. A first spring mechanism including inner spring arms 712 and a second spring mechanism including outer spring arms 710 hold membrane 714 in a closed position, and can be outwardly compressed, releasing membrane 714, thereby providing an opening for the flow of fluid therethrough. At small pressure differentials, inner spring arms 712 may be pushed outwardly until they hit outer spring arms 710. At higher pressures, such as during a CHF event, inner and outer spring arms 710 and 712 are pushed further outwardly, opening membrane 714 further, to allow for a greater amount of blood to pass through shunt 700.

Figure 9:
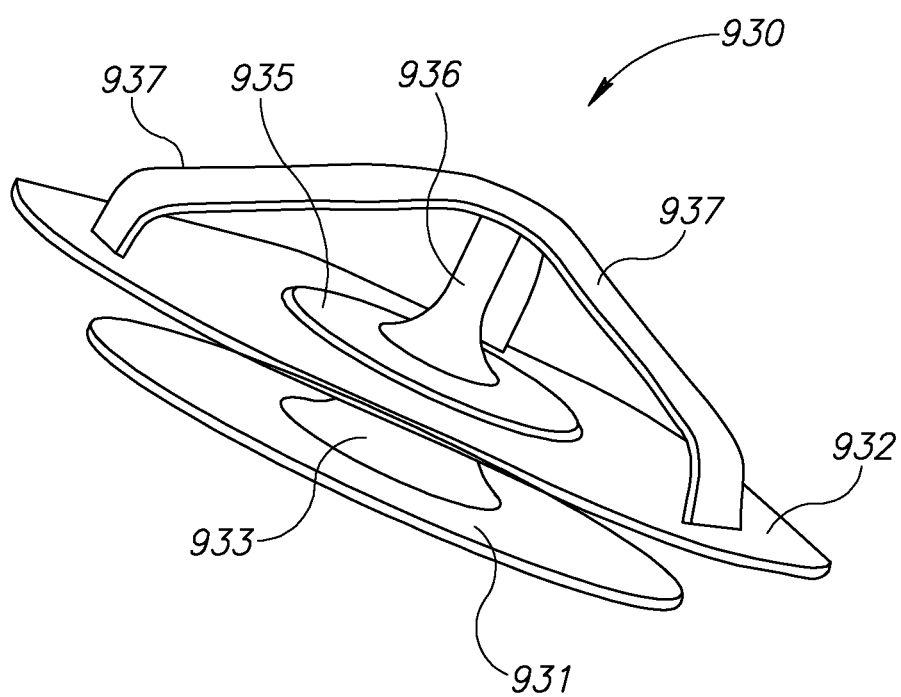
FIG. 9 is a schematic illustration of a valve, in accordance with an exemplary embodiment of the invention.

FIG. 9 is a schematic illustration of a valve 930, in accordance with an exemplary embodiment of the invention. Valve 930 is shown as being mounted on an anchor device similar to device 171 of FIG. 4B. In valve 930, skirts 931 and 932 are intended to capture a tissue wall between them. A rim 933 connects the skirts 931 and 932 and defines a blood passage between them. A cover 935 (corresponding to flap 138) mounted on a compressible rod 936 serves as a flap which controllably blocks flow through rim 933. Optionally, a plurality of members 937 connected to skirt 932, support compressible rod 936. Valve 930 may have any of the opening profiles discussed above regarding flap 138, including preload embodiments in which the rest point of cover 935 is below skirt 932 and even possibly below skirt 931.

Alternatively or additionally to rod 936 being compressible, members 937 provide elasticity allowing movement of cover 935. Cover 935 is mounted in accordance with this alternative on a plurality of members (or arms), optionally at least three arms.

It is noted that the valve arrangement of valve 930 does not necessarily need to be mounted on continuous skirts 931 and 932, but rather may be mounted on other anchors, such as anchor 100. In some embodiments of the invention, anchor 100 is embedded within skirts 931 and/or 932.

Closure Device

The above described anchor devices may also be used to carry a closure device for sealing undesired orifices in internal tissue walls of humans. For example, instead of flap 138 being mounted on central orifice 106 in a manner which allows opening of the orifice for flow, flap 138 may be mounted over central orifice 106 permanently or any other cover may be mounted on the anchoring device to cover orifice 106. Similarly, the other embodiments of anchor devices and valves described herein may be used with minimal changes in construction of closure devices.

Figure 10A:
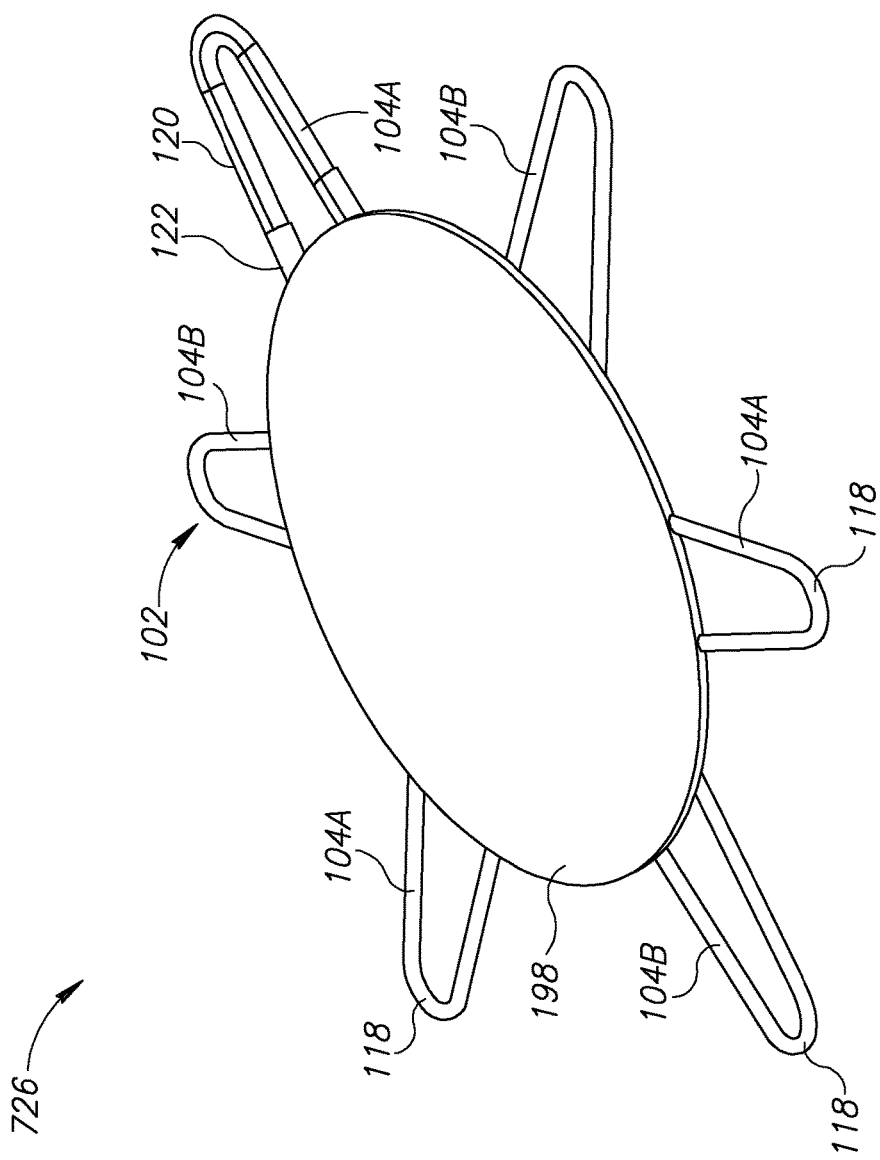
FIGS. 10A and 10B are schematic illustrations of closure devices, in accordance with exemplary embodiments of the invention.

FIG. 10A is a schematic illustration of a closure device 726, in accordance with an exemplary embodiment of the invention. Device 726 comprises an anchoring portion formed from petals 104A and 104B and a closure portion 198, which seals an orifice defined by petals 104. Closure portion 198 is optionally substantially larger than the area of orifice 106, for example having an area at least 10%, 20% or even at least 40% greater than orifice 106. Such a large closure portion achieves a substantially immediate closure of the hole upon deployment and there is no need to wait for tissue growth to achieve the seal.

Figure 10B:
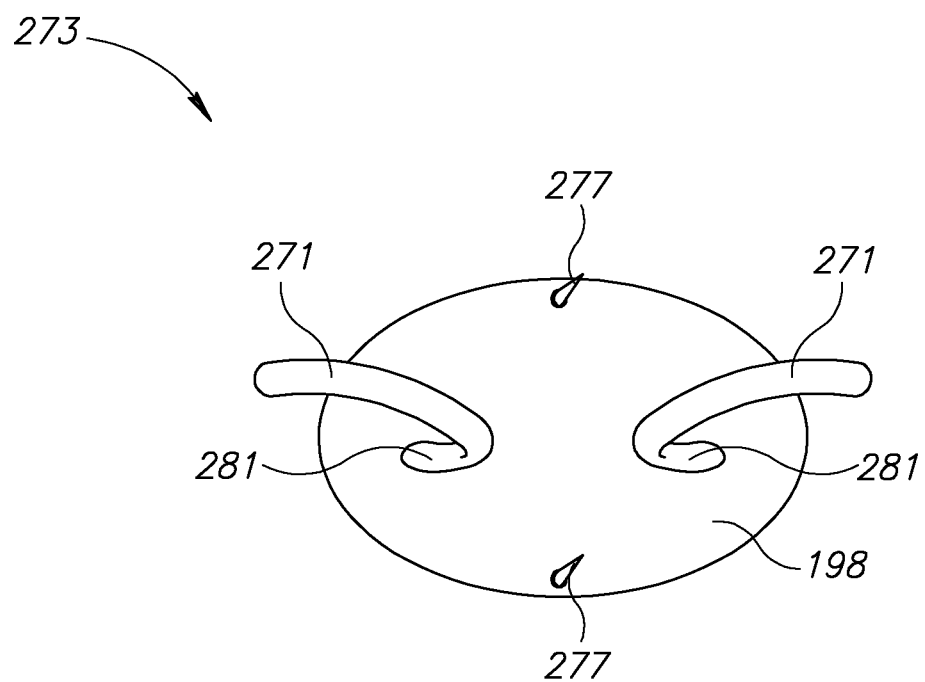

FIG. 10B is a schematic illustration of a closure device 273, in accordance with another exemplary embodiment of the invention. Closure device 273 comprises a closure portion 198 and a plurality of anchoring arms 271 adapted to engage tissue between the arms 271 and closure portion 198. Alternatively, a lower portion 281 of arms 271 may extend sufficiently long, such that wall tissue is caught between the ends of arms 271.

In some embodiments of the invention, arms 271 extend beyond the outer perimeter of closure portion 198. Alternatively, arms 271 are shorter. As shown, arms 271 are located relatively close to the outer perimeter of closure portion 198. Alternatively, arms 271 may be located in the center of closure portion 198, adjacent each other.

While two arms are shown, closure device 273 may include more arms, possibly at least four or even at least six arms. The arms are optionally elastic, for example formed from a suitable polymer or metal. In some embodiments of the invention, the arms are pre-shaped in an open state which engages tissue and are delivered in a folded state. Upon release, the arms engage the tissue wall. Alternatively, the arms are bent by a delivery tool into their engaging state.

Alternatively or additionally, closure device 273 may include one or more pins 277 which engage tissue by penetration therein.

In an exemplary embodiment of the invention, in treating an aneurism, for example in the septum, an orifice is perforated in the aneurism and a closure device is implanted in the orifice, to strengthen the wall suffering from the aneurism.

The closure devices may be produced using any of the methods discussed above regarding the skirt 116 and flap 138, for example using nitinol, stainless steel and/or thermoplastic polymers. In some embodiments of the invention, a closure device as in FIG. 10A or FIG. 10B is produced as a monolithic unit from nitinol or a polymer.

Gradual Closure

In some embodiments of the invention, valve 180 (FIG. 4A) is used to achieve a gradual closure device. Flap 138 is set to require a very large pressure in order to open, thus keeping it permanently closed absent an additional opening force. A bio-degradable stopper optionally holds flap 138 open, until it dissolves. Alternatively or additionally, skirt 116 and/or other surfaces of valve 180 are coated with a bio-degradable material, which prevents tissue growth. Once the bio-degradable material dissolves, tissue begins to grow on skirt 116 until the tissue growth causes valve 180 to be permanently closed. In some embodiments of the invention, beneath the bio-degradable material skirt 116 has a tissue growth enhancing drug, in order to speed up the tissue growth. Alternatively or additionally, the smoothness of skirt 116 and/or other surfaces of valve 180 are selected according to a desired closure time. Further alternatively or additionally, closure device 726, closure device 273 or a variation thereof is used with a mesh instead of closure portion 198. The density of the mesh optionally determines the time between implant and achieving the complete closure, possibly together with other parameters, such as anti-coagulation drug administration.

The time during which the material keeping the flow path open dissolves is optionally selected according to the needs of the patient. In an exemplary embodiment of the invention, the time passing until the flap permanently closes is at least a week or even at least 2 or 3 weeks.

The bio-degradable material may include, for example PEG (Poly Ethylene Glycol), although other materials may be used.

Cannula Carrier

Figure 11:
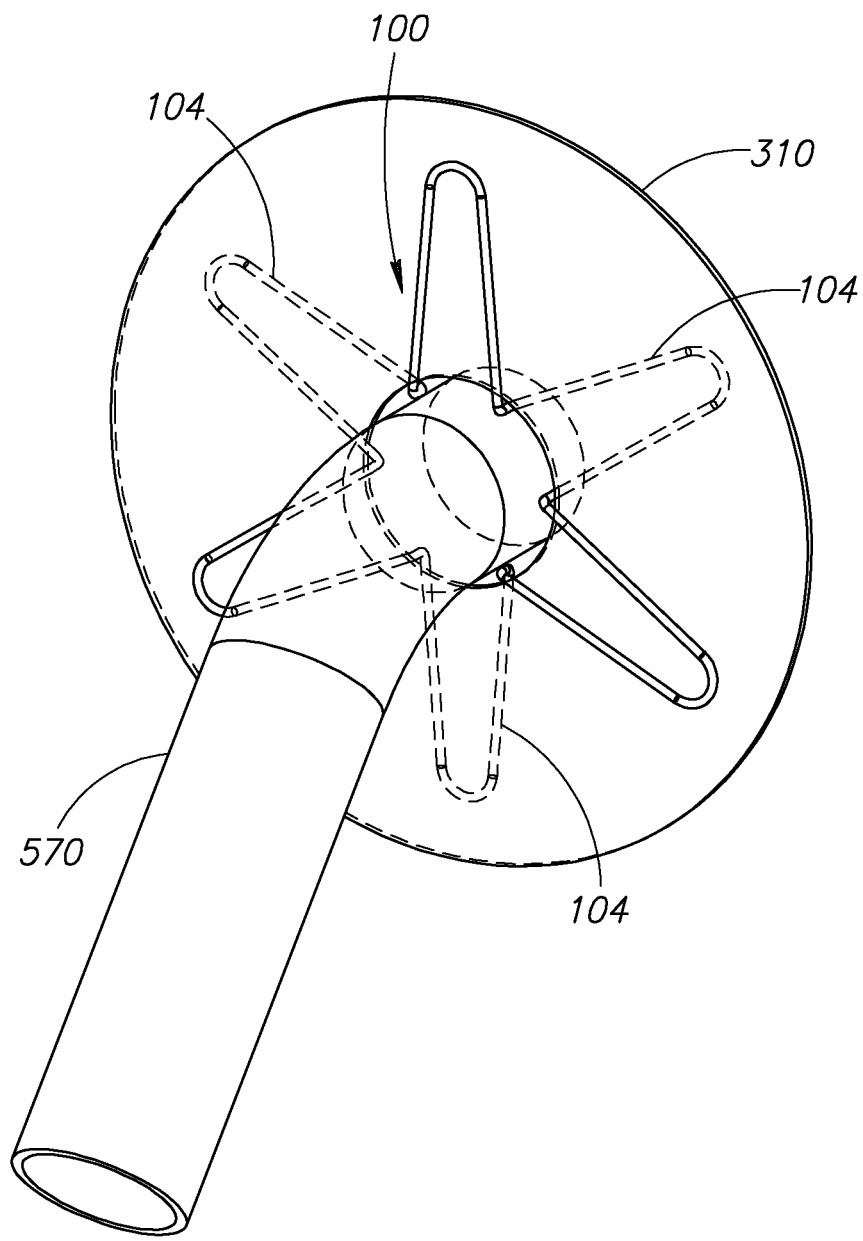
FIG. 11 is a schematic illustration of an anchoring device holding a cannula, in accordance with an exemplary embodiment of the invention.

FIG. 11 is a schematic illustration of using anchoring device 100 to hold a cannula 570, in accordance with an exemplary embodiment of the invention. Cannula 570 may be held, for example, in the inter-atrial septum 310 for draining blood from the left atrium to the arterial system, for example as part of a cardiac assist device. Alternatively, device 100 may be used in holding tubes in other locations, for example a tube leading from the left atria to the right atria.

Valve with Controller

FIG. 12 is a schematic top view of an implantable flow control devise 280, in accordance with an exemplary embodiment of the invention. Device 280 comprises three petals 154A adapted to be located on one side of a wall and three petals 154B adapted to be located on another side of the wall. FIG. 12 illustrates that petals 154A and 154B may be of different lengths and that each two petals 154A may be separated by a plurality of petals 154B. In this arrangement, points 174 between petals 154A and 154B serve to prevent wall tissue from entering the central orifice, while proximal points 172 between adjacent petals 154B do not serve in preventing tissue from extending into the central orifice, since the petals 154B on both their sides are on the same side of the wall. While points 172 do not add to the functionality of device 180 upon implantation, they optionally add to the anchoring of the device when tissue begins to cover device 180. FIG. 12 further illustrates a flap 138 mounted on a hinge 147 which serves as a valve, sensors 142 and 144, a motor 196 and a controller 192.

In some embodiments of the invention, the opening and closing of flap 138 is controlled by a controller 192, which controls the opening and closing according to predetermined settings and/or according to readings of one or more sensors, for example any of the sensors detailed hereinbelow. Controller 192 optionally controls the valve using any method known in the art, such as using an electromagnet and/or a motor 196. The sensors may be located adjacent device 180, or may be remote from the device. In some embodiments of the invention, controller 192 allows a human operator to provide override commands which open, close or otherwise set the state of flap 138, without relation to the predetermined schemes for opening and closing the flap. The override commands may be provided, for example, through wires leading along the patient to a surface port on or beneath the patient's skin. Other methods of externally controlling flap 138 include magnetic and/or RF coupling. Operation energy may be provided to controller 192 by an embedded battery and/or by an external source. In some embodiments of the invention, an anchor device is coupled to a pacemaker or ICD and shares with its power source.

The control may be performed according to any of the schemes known in the art and/or any of those described in US patent publication 2002/0173742, filed Apr. 20, 2001 and/or PCT publication WO 2005/074367, filed Feb. 3, 2005, the disclosures of which patent documents are incorporated herein by reference. For example, the opening of flap 138 may depend on the absolute pressure in one or more of the chambers of the heart, on the temperature in one or more chambers of the heart, on the patient's blood pressure and/or on the patient's blood oxygen content. The control may also depend on any of the parameters used by pacemakers, for example in synchronized pacing.

In some embodiments of the invention, device 180 may include a pump 194, which aids in passing blood through the central orifice, for example under instructions from controller 192. Possibly, pump 194 and/or motor 196 are used in the normal operation of device 180, substantially every time flap 138 is opened or opened to a large extent. Alternatively, pump 194 and/or motor 196 operate responsive to sensors that identify that flap 138 did not sufficiently open. Further alternatively, pump 194 and/or motor 196 are used substantially only to override the normal operation of flap 138 according to external human instructions. Alternatively to the override being performed by an internal device (e.g., motor 196), possibly battery operated, the override is performed by an external device, for example by magnetic external control.

Sensors

Device 280 further illustrates the mounting of sensors 142 and 144 on the implanted device. As shown, a first sensor 142 is mounted on petal 154A and is located on one side of the wall, while a second sensor 144 is mounted on petal 154B, located on the other side of the wall. Thus, readings from both of sensors 142 and 144 may be read and compared in order to determine the relative conditions on opposite sides of the wall. In an exemplary embodiment of the invention, sensors 142 and 144 comprise one or more temperature sensors and the relative temperature is used to determine the flow pattern of blood in the patient or any other characteristic of the patient's state. Alternatively or additionally, any other sensors may be used and more or fewer sensors may be mounted on device 180. For example, the sensors may include one or more pressure sensors, oxygen ($O_2$) sensors, B Natriuretic Peptide (BNP) sensors, a sensor of toxic components, flow sensors and/or pH sensors.

In some embodiments of the invention, the readings of sensors 142 and/or 144 are used by controller 192 or an external controller, in directly determining when flap 138 is to be opened/closed. Alternatively or additionally, controller 192 or any other controller, monitors the health state of the patient using readings of one or more internal and/or external sensors, and accordingly sets the opening profile of flap 138 as a function of the pressure difference. Optionally, when it is determined that the patient has recovered entirely, or when otherwise advantageous, controller 192 instructs the valve to remain closed permanently. Possibly, when necessary, controller 192 changes the minimal or maximal pressure required to open the valve. In an exemplary embodiment of the invention, when the state of the patient deteriorates, the amount of blood allowed to flow through the valve in its "closed" state is decreased. In other embodiments, controller 192 may respond in other ways to the patient deterioration, according to the specific medical intervention considered best for the patient.

Alternatively or additionally, the readings of the sensors are transmitted to a monitoring station outside the patient's body, using wire and/or wireless transmission methods, for example using any of the methods in the above described patent publications US patent publication 2002/0173742, filed Apr. 20, 2001 and/or PCT publication WO 2005/074367, filed Feb. 3, 2005.

Exemplary Deployment Method

Figure 13:
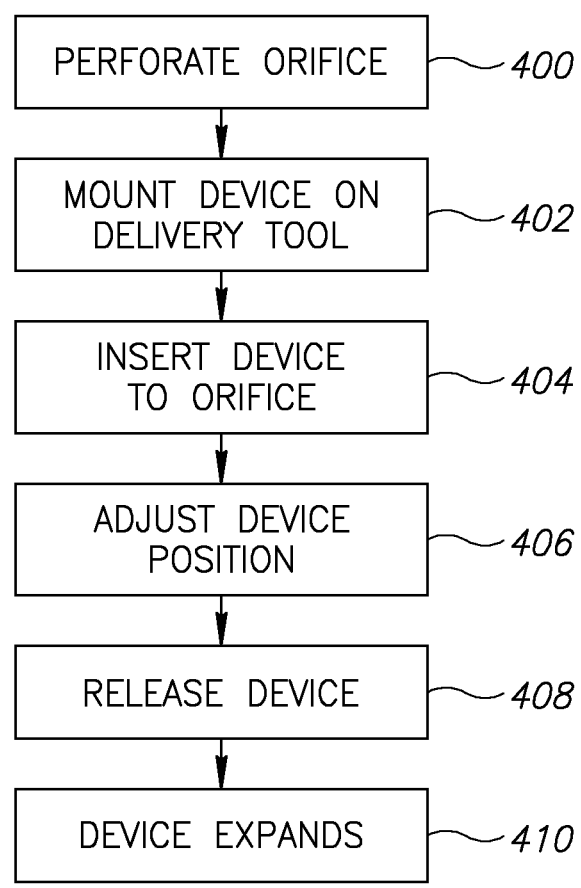
FIG. 13 is a flowchart of acts performed in implanting an anchoring device in a heart, in accordance with an exemplary embodiment of the invention.

FIG. 13 is a flowchart of acts performed in implanting an anchoring device (e.g., device 100) in a heart in a minimally invasive procedure, in accordance with an exemplary embodiment of the invention. Device 100 is optionally delivered to the heart on a delivery device, through a peripheral vein or artery, such as the femoral vein or the right or left jugular veins in animals, or the right or left subcalvian in humans.

If not already existent, an orifice is optionally formed (400) in a wall of the heart, at a required location. In an exemplary embodiment of the invention, the orifice is created using a transeptal puncture tool, for example one including a needle and a dilator catheter. In some embodiments of the invention, the orifice is gradually enlarged, for example with a series of diameter increasing dilators and/or with a non-compliant balloon, until it reaches the desired size for the anchoring device used. The balloon may be provided on the delivery tool of the anchor or on a different tool. Alternatively, when a self expanding device, such as anchoring device 100, is used, gradual enlarging is not required and the entire medical procedure is shorter. The orifice may be formed in muscle but is preferably formed in a membrane which is easier to perforate. While device 100 may be used to expand the orifice in which it is implanted, in some embodiments of the invention device 100 does not expand the orifice and the expansion is performed using dilating methods known in the art.

Alternatively, the device is implanted in an existing orifice, for example in place of an inoperative natural valve and/or in an undesired orifice for example in order to close the orifice or to monitor the flow therethrough.

In some embodiments of the invention, the orifice is created in the patient immediately before the implantation of the anchor device, for example less than six hours, two hours or even less than 30 minutes before the implantation. Alternatively, the anchor device is implanted in the patient more than a day, more than a week or even more than a month after the orifice was created and/or identified.

The device 100 is provided (402) in a folded state mounted on a distal end of a delivery medical tool. The minimally invasive tool is then inserted (404) into the patient and the device is brought to the orifice into which it is to be implanted. Optionally, the position of the device is accurately adjusted (406) and/or the device is rotated, until the device is in place, within an orifice in a wall, for example between two heart chambers. The device is then released (408) from the delivery tool and optionally self opens into its open state, such that some of the petals are on one side of the wall and some are on the other side of the wall.

In some embodiments of the invention, device 100 continues to expand (410) in place with curve points 112 radially pushing against the tissue of the wall and expanding the orifice. Thus, the size of the orifice is radially increased, reducing the chances of trauma from shear forces in forming the orifice. Possibly, the formed orifice has a diameter of less than 4 millimeters, less than 3 millimeters or even less than 2 millimeters and the expansion of the device increases its diameter by at least 20%, 40% or even at least 60%. Alternatively or additionally to self expanding, the anchoring device may be expanded by a balloon, possibly a balloon delivered on the same delivery tool as the anchoring device or on a different tool guided on a same guide wire as the delivery tool of the anchor device. Further alternatively, any other method of generating the orifice may be used.

The implanting of device 100 in the heart is optionally performed while the area is imaged by a real time imaging modality, such as Intracardiac Echo (ICE), Angio and/or Trans-esophageal Echocardiogram (TEE). In some embodiments of the invention, crimp bar 120 and/or any other marker (e.g., radio-opaque marker) is used to aid in properly orienting and/or positioning device 100 in place. Radio-opaque markers, when used, are optionally positioned at extreme locations of the anchoring device, for example at the most radially distal points and/or the most radially inner points.

As described below, the medical delivery tool is optionally designed such that the device may be moved back and forth as much as required for accurately adjusting (406) the location of the device. Possibly, once the device is released in place, it cannot be easily removed.

Device Release

In some embodiments of the invention, the release of the device is performed all at once, such that all of petals 104 open from their folded state substantially concurrently. Alternatively, the release is performed gradually, in a plurality of steps. In an exemplary embodiment of the invention, petals 104 of a distal side of the wall from the direction in which the delivery tool approaches the orifice (referred to herein without loss of generality as petals 104A) are released first, and thereafter the petals 104B of the proximal side of the wall are released. In other embodiments of the invention, each of the petals is held separately and released separately, for example as described below with reference to FIG. 17 and/or in U.S. provisional applications 60/761,192, titled "Delivery System for Flow Regulation Device", filed Jan. 23, 2006 and 60/777,315, titled "Arm Configuration for Flow Regulation Device", filed Feb. 28, 2006, the disclosures of which documents are incorporated herein by reference. In an exemplary embodiment of the invention, device 100 is folded non-symmetrically, so that each petal is released separately.

Device 100 is optionally preset in the open state, such that absent an external force it moves to and remains in the open state, using spring loading, pre-shaping, heat shrinking or any other method known in the art. Possibly, device 100 is elastically packaged, such that petals 104 spread out on their own when released from the delivery tool. Alternatively or additionally, external forces are used to induce the spreading out of the petals, for example an externally applied magnetic force. Further alternatively or additionally, a force applied through a minimally invasive tool, such as a catheter balloon, is used to expand device 100 to its open state.

Exemplary Delivery Mechanism

Figure 14A:
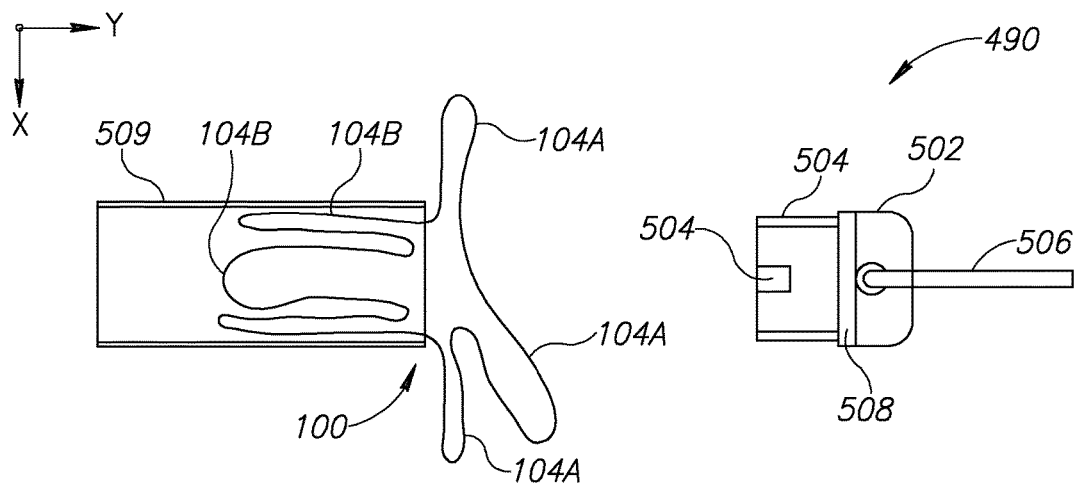
FIG. 14A is a schematic illustration of anchoring device being mounted into a magazine, in accordance with an exemplary embodiment of the present invention.

FIG. 14A is a schematic illustration of anchoring device 100 being mounted into a delivery tool 490, in accordance with an exemplary embodiment of the present invention. Delivery tool 490 comprises an outer channel 500 (FIGS. 14C and 14D), a core 502 and a rod 506, adapted to push and pull core 502 within outer channel 500. In FIG. 14A, device 100 is partially inserted into a proximal side of a magazine 509 in a folded shape having a small diameter convenient for leading into the patient in a minimally invasive tool. Optionally, magazine 509 has a size of less than 18 French, less than 15 French or even less than 12 French. Petals 104B are inserted distally into magazine 509, as petals 104B are intended to be located on a distal side of the wall on which device 100 is mounted. In an exemplary embodiment of the invention, the distal side of the wall comprises the left atrium which is to receive as little as possible foreign materials. Alternatively or additionally, the side of the wall considered as the distal side is selected according to the direction in which delivery tool 490 is brought to the vicinity of the wall.

In some embodiments of the invention, core 502 comprises a stiff material sufficiently hard to engage petals 104, but not too hard so as not to damage delicate surfaces with which it may come in contact, such as ceramic and/or oxidized surfaces of skirt 116, arm 135 or flap 138 (FIG. 4A). Optionally, the material of core 502 has low friction with channel 500, and is suitable for acute contact with tissue. In an exemplary embodiment of the invention, core 502 comprises Delrin, Teflon, Nylon, Pebax and/or any other suitable plastic. Alternatively, core 502 is formed of a metal or alloy.

Figure 14B:
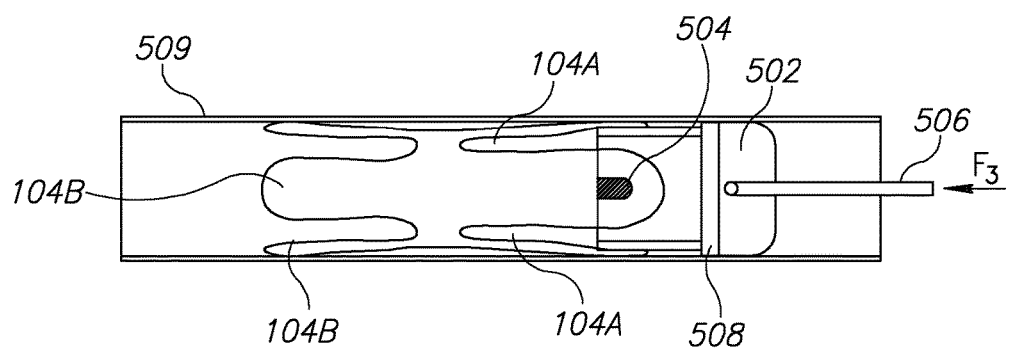
FIG. 14B is a schematic illustration of an anchoring device within a magazine, in accordance with an exemplary embodiment of the present invention.

FIG. 14B is a schematic illustration of anchoring device 100 within magazine 509, in accordance with an exemplary embodiment of the present invention. Core 502 comprises a plurality of protrusions 504, optionally a protrusion for each petal 104A. Petals 104A are placed in magazine 509 in a manner such that they are caught between protrusions 504 and magazine 509. protrusions 504 allow device 100 to be pulled proximally within magazine 509 and channel 500, by pulling rod 506 proximally. Core 502 further optionally comprises a shelf 508 which pushes device 100 distally within magazine 509 and channel 500, when rod 506 is pushed distally. In some embodiments of the invention, as shown in FIG. 14B, there is a short extent of axial freedom between pulling and pushing device 100 by core 502. Alternatively, core 502 firmly catches device 100 substantially without any axial freedom.

It is noted that device 100 may be provided from a manufacturer already mounted within magazine 509 or may be mounted by a physician or a medical staff member before the implantation procedure. For example, immediately before (e.g., on the same day, less than an hour before) the implantation procedure, the state of the patient may be determined and accordingly a specific device 100 to be used may be selected and mounted in magazine 509.

Figure 14C:
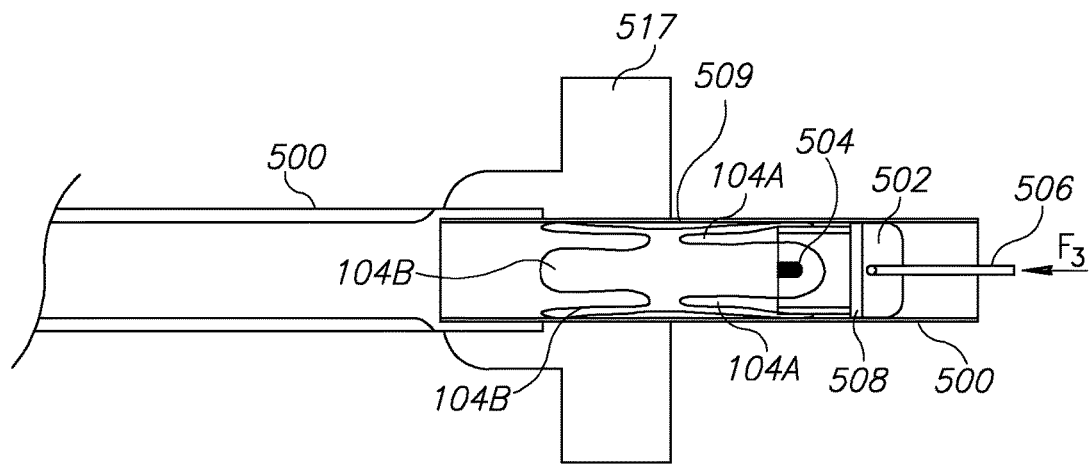
FIG. 14C is a schematic illustration of an anchoring device being moved from a magazine to a delivery channel, in accordance with an exemplary embodiment of the present invention.

FIG. 14C is a schematic illustration of the transfer of anchor device 100 from magazine 509 to channel 500, in accordance with an exemplary embodiment of the invention. The inner diameter of magazine 500 is optionally designed to be substantially equal to the inner diameter of channel 500. Magazine 500 with anchor device 100 folded within it is inserted into a haemostatic valve 517 of delivery tool 490 (FIG. 14A). Rod 506 is then pushed forward to move anchor device 100 out of magazine 509 into channel 500. Thus, the inner diameter of channel 500 does not need to be large enough to receive magazine 509 and there is more room for folded anchor device 100 and/or channel 500 can have a smaller outer diameter.

Figure 14D:
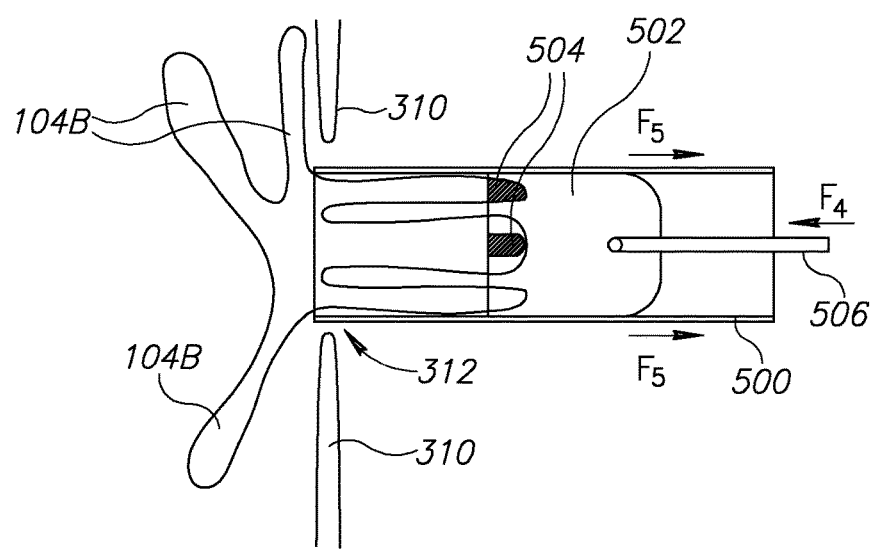
FIG. 14D is a schematic illustration of anchoring device within a delivery channel in the vicinity of a wall in which it is to be implanted, in accordance with an exemplary embodiment of the present invention.

FIG. 14D is a schematic illustration of anchoring device 100 within delivery tool 490 in the vicinity of a wall 310, in accordance with an exemplary embodiment of the present invention.

Optionally, channel 500 is inserted into the patient using any method known in the art and then rod 506 is pushed through channel 500 and brought adjacent an orifice 312 in a wall 310.

After the distal end of channel 500 is passed through orifice 312, rod 506 is carefully pushed distally for a small extent, sufficient to release petals 104B from the distal end of channel 500, but not to an extent which will allow petals 104A to escape channel 500. Petals 104B optionally elastically expand to the flat open configuration, which prevents pulling device 100 proximally from wall 310. Channel 500 and rod 506 are optionally pulled proximally together such that petals 104B rest against wall 310. Channel 500 is then pulled proximally, while rod 506 is held stationary, so as to release petals 104A from the channel. Petals 104A optionally self expand, such that device 100 moves to the expanded state shown in FIG. 1. Thereafter, channel 500 and rod 506 are removed from the patient and the implant procedure is complete.

In some embodiments of the invention, even after petals 140B are released, rod 506 can be pulled proximally so as to pull petals 104B back into channel 500.

In some embodiments of the invention, during the insertion, petals 104A and/or 104B and/or other portions of device 100 are covered by a bio-degradable material, such as poly ethylene glycol, which prevents the petals from tangling during the insertion process. When device 100 is released from channel 500, the bio-degradable material is dissolved and the petals open.

Optionally, if desired to release each petal separately, protrusions 504 are located on core 504 at different axial levels and each protrusion catches a different petal. In some embodiments of the invention, one or more protrusions hold a plurality of petals 104 together.

Although the above described method may be performed manually by a physician carefully controlling rod 506 and channel 500 from their proximal ends, in some embodiments of the invention, a proximal control handle is provided for control of the delivery process, at the proximal end of channel 500, as is now described with reference to FIGS. 15A-15C.

Figure 15A:
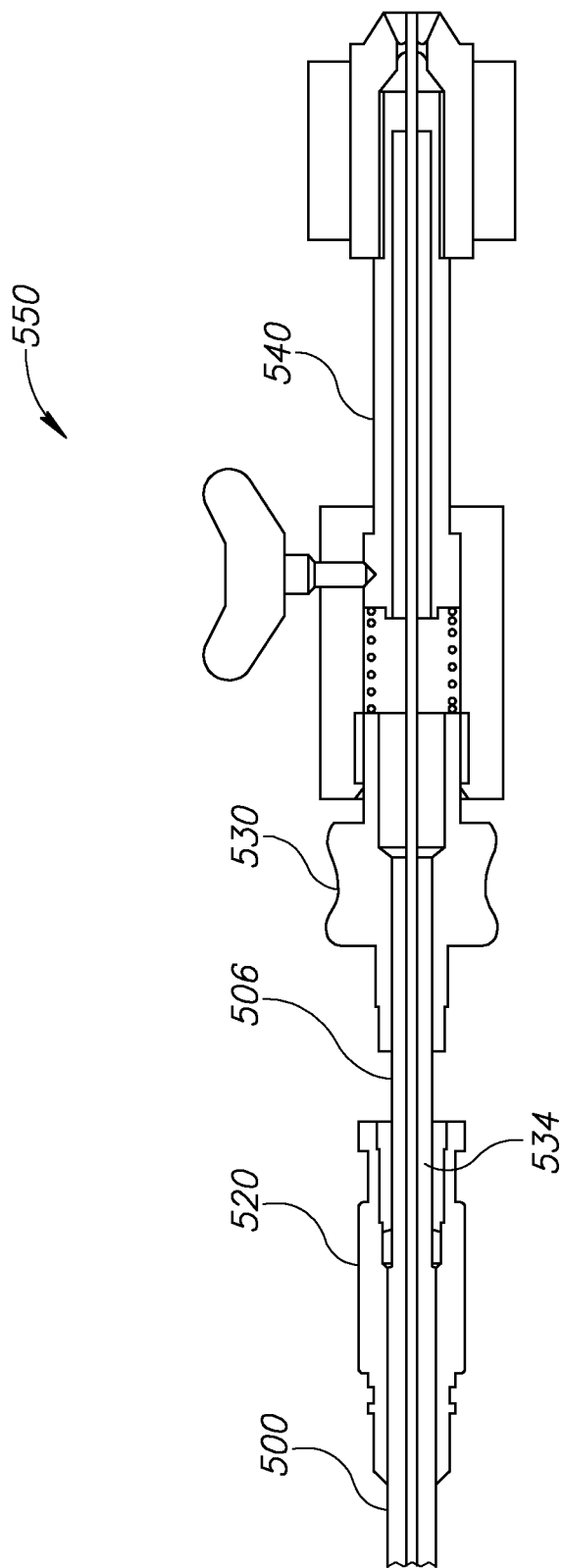
FIGS. 15A-15C are schematic illustrations of a handle of a minimally invasive delivery tool, in a process of implanting an anchoring device, in accordance with an exemplary embodiment of the invention.
Figure 15B:
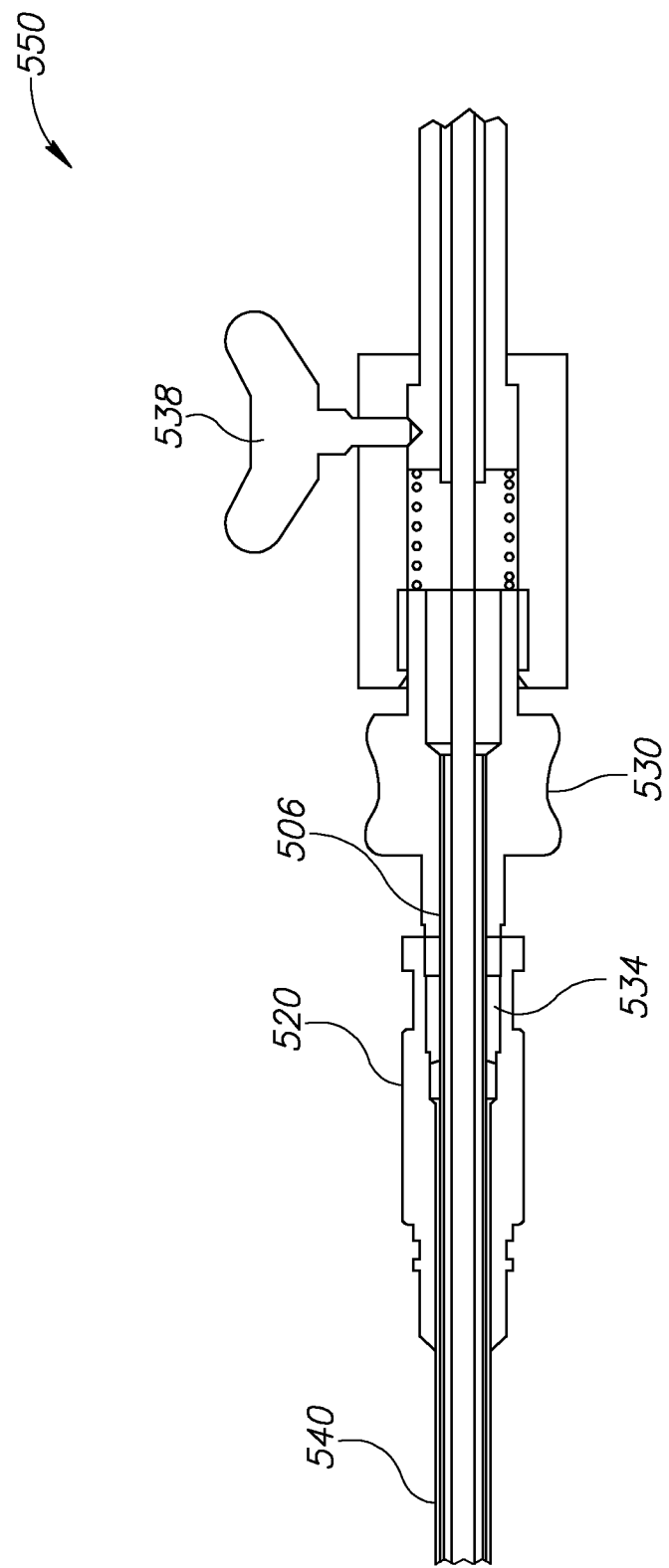
Figure 15C:
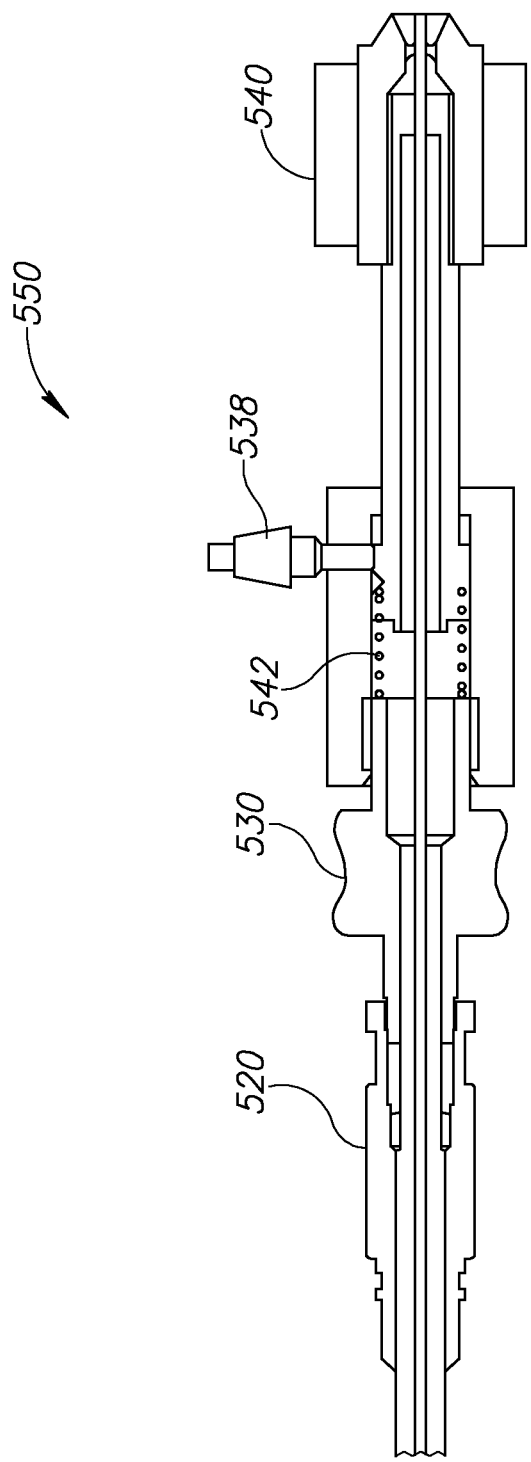

FIGS. 15A-15C are schematic illustrations of a handle 550 of a minimally invasive delivery tool, in a process of implanting an anchoring device, in accordance with an exemplary embodiment of the invention. Handle 550 includes a proximal channel handle 520 which is used to push and pull channel 500. A rod handle 530 is used to move rod 506 backwards and forwards. In inserting delivery tool 490 (FIG. 14A) into the patient, both of handles 520 and 530 are optionally used to push channel 500 and rod 506 together into the patient. In order to release petals 104B from channel 500 (FIG. 14C), handle 530 is pushed distally into a niche 534 within handle 520, which only allows advancement of handle 530 with rod 506 to an extent, shown in FIG. 15B, which allows release of petals 104B and not petals 104A. Thereafter, handles 520 and 530 are pulled proximally together to bring expanded petals 104B against wall 310. Optionally, handles 520 and 530 may be rotated together, to bring device 100 to a desired orientation. At this point, it is required to pull channel 500 proximally relative to rod 506, in order to release petals 104A. In an exemplary embodiment of the invention, this is achieved, by first opening a safety lock handle 538, which allows movement of a back handle 540, relative to handle 530. Back handle 540 is optionally held stationary, while handles 520 and 530 are pulled proximally, so as to pull channel 500 proximally relative to rod 506 and release petals 504A. In some embodiments of the invention, the relative movement of handle 530 relative to back handle 540 is damped by a spring 542 which prevents undesired rough movements which may pull petals 104B out of place.

In some embodiments of the invention, rod 506 is not hollow. Alternatively, a hollow channel passes within rod 506, which may be used for passing fluids into and/or out of the patient. For example, a channel within rod 506 may be used for rinsing and/or applying suction to remove air bubbles. In some embodiments of the invention, a channel through rod 506 may be used for passing tools, e.g., a wire, to the vicinity of anchoring device 100. Optionally, core 502 also has a channel defined through it, serving as a continuation of the channel passing through rod 506. In some embodiments of the invention, rod 506 comprises a catheter.

It is noted that the details of the delivery tool may be varied and other types of delivery tools may be used. For example, while in FIGS. 14A-14C each petal 104 is held by a separate protrusion 504, in some embodiments of the invention fewer protrusions may be used, although less controlling the delivery process.

Delivery of Additional Elements

Optionally, in embodiments in which device 100 carries additional elements, such as skirt 116, flap 138 and crimped tube 120, these elements are mounted on proximal petals 104A, such that they are delivered on the proximal side of the wall 310. Optionally, skirt 116 is folded into channel 500 between petals 104A, such that the petals 104A catch skirt 116 between them. Alternatively, the skirt is folded around the petals, from the outside. Further alternatively or additionally, any other delivery methods may be used, for example any of the methods described in above mentioned PCT publication WO 2005/027752.

Figure 16:
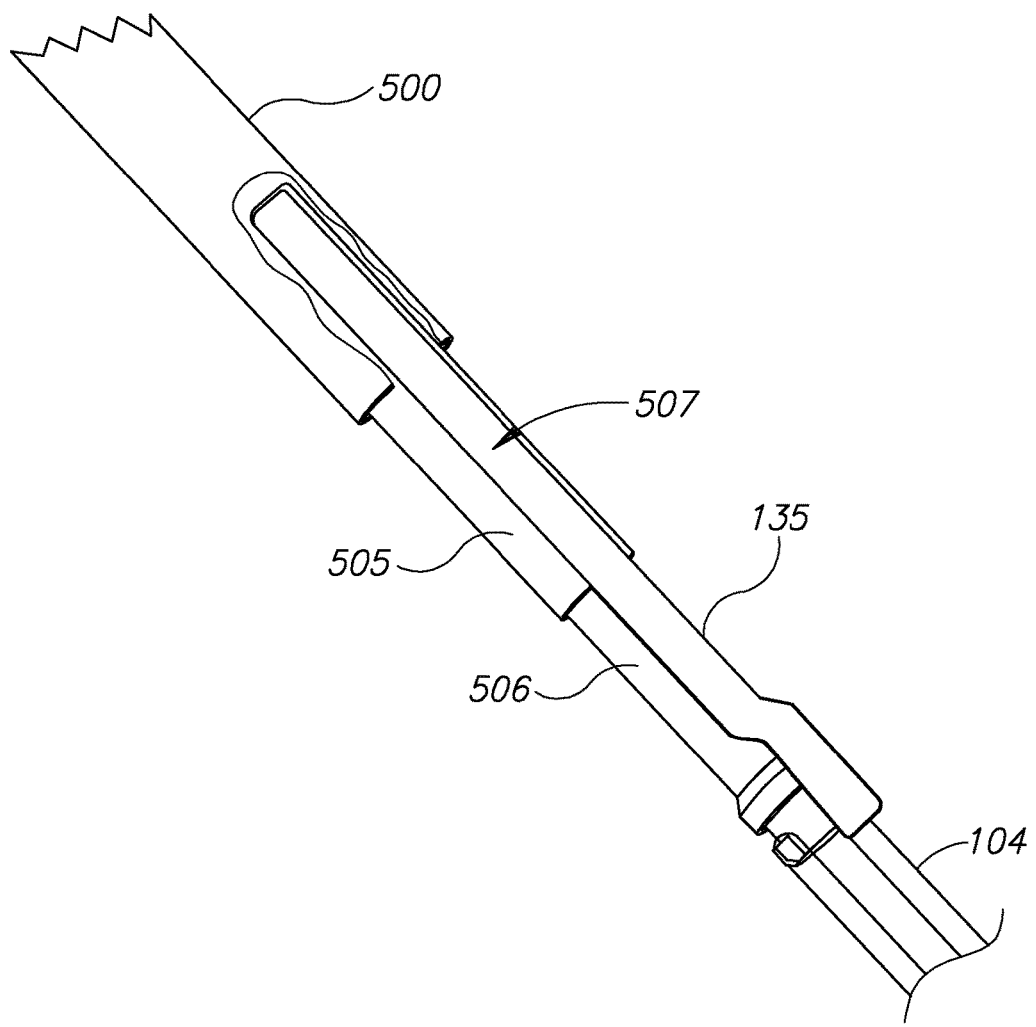
FIG. 16 is a schematic view of a distal end of a delivery tool carrying a valve flap, in accordance with another exemplary embodiment of the present invention.

FIG. 16 is a schematic view of a distal end of delivery tool 490, in accordance with another exemplary embodiment of the present invention. In FIG. 16, delivery tool 490 is used to deliver an anchoring device 100 together with flap 138 and arm 135 (FIG. 4A). In FIG. 16, delivery tool 490 includes in addition to channel 500 and rod 506, a slotted tube 505 which is partially cut out toward its distal end. Flap 138 and arm 135 are held between tube 505 and rod 506 spread out on the rod. The use of tube 505 protects channel 500 from sharp edges of flap 138, for example when it is formed from nitinol.

The cut out portion 507 of tube 505 optionally spans over less than the width of flap 138, possibly even less than the width of arm 135, such that the edges of the flap (and arm 135) come in contact with tube 505 rather than with channel 500. In some embodiments of the invention, cut out portion 507 spans over at least 40°, 60° or even at least 90° of the perimeter of rod 506. In an exemplary embodiment of the invention, rod 506 has a diameter of between about 8-12 French, although smaller or larger sizes may be used. Channel 500 optionally comprises a soft material which is simple to produce, use and move against body tissue, but is easily cut by sharp edges. For example, channel 500 may comprise PTEE, PEBAX or other polymer materials. Tube 505 optionally comprises a more durable material than channel 500. Alternatively, tube 505 is formed from the same material as channel 500, possibly being thicker.

While tube 505 is within channel 500, flap unit 189 is held in its flat state, as shown in FIG. 16, and optionally does not substantially come in contact with channel 500. When cut out portion 507 of tube 505 is pushed distally out of channel 500, or when channel 500 is retracted, flap unit 189 is allowed to exit through cut out portion 507. In some embodiments of the invention, flap unit 189 is adapted to bend in a manner in which it narrows and exits through cut out portion 507. Alternatively or additionally, tube 505 comprises a soft, flexible and/or elastic material, although preferably not as soft as channel 500, and flap unit 189 is designed to apply pressure against tube 505. Cut out portion 507 optionally expands under the pressure and allows flap unit 189 to move radially out of tube 505, perpendicular to, and away from, rod 506. Once released, flap unit 189 optionally sets into its predetermined state in which it is employed. Using a soft material for tube 505 additionally allows flap 138 to slightly dig or cut into tube 505 and thus stabilizing flap unit 189 while it is delivered within channel 500.

Alternatively to tube 505 allowing flap 138 and arm 135 to exit once it is pushed out of channel 500, other triggers may be required to cause tube 505 to allow flap 138 to be released. For example, tube 505 may be made from a stiff material which softens when cooled or heated. When it is desired to release flap 138, the tube 505 is heated or cooled in order to release the flap unit. Alternatively or additionally, a biodegradable material is used to hold tube 505 in a state which prevents release of flap 138.

Alternatively to delivering flap 138 and arm 135 spread out flat, valve 180 is delivered in a folded state similar to that shown in FIG. 4A. Optionally, flap 138 is rolled into a rod which is a continuation of arm 135 and petals 104 with skirt 116 are folded over the rolled up flap. In this state, device 180 is inserted into a delivery tool for delivery to an internal organ of the patient. In a variation of this embodiment, rather than being folded at the maximal curvature point of hinge 146, during delivery, arm 135 is folded during delivery at a point closer to flap 138, to prevent the flap for passing through the orifice and getting stuck therein.

Additional Delivery Embodiments

In the embodiment described above with reference to FIG. 14C, all of the petals 104A on one side of the wall are released together. While this is preferred for some anchoring devices, other devices may have a risk of petal (or arm) entanglement when allowing all the petals to be released together.

Figure 17:
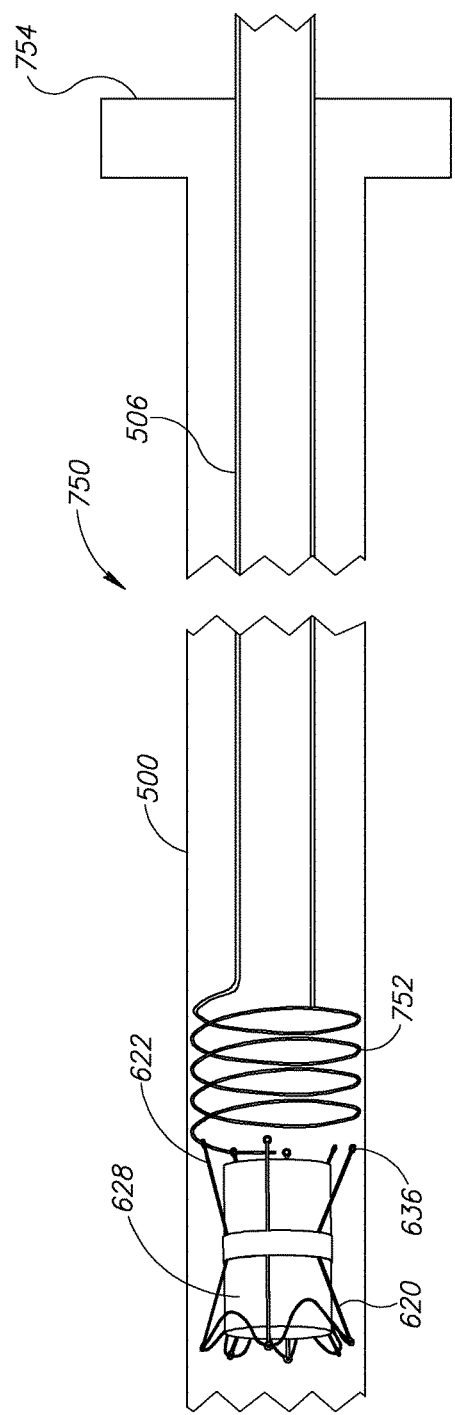
FIG. 17 is a schematic illustration of a delivery tool, in accordance with another exemplary embodiment of the invention.

FIG. 17 is a schematic illustration of a delivery tool 750 of anchoring device 600 (FIGS. 6A and 6B), in accordance with an exemplary embodiment of the invention. Delivery tool 750 comprises an outer channel 500 and an inner rod 506 with a curled wire 752 in the shape of a coil at its distal end. A handle 754 is used to move channel 500 relative to inner rod 506 and/or to entirely move delivery tool 750 into the patient. In use, anchoring device 600, with shunt 628 mounted on it, is mounted in its folded state within channel 500. Proximal arms 622 are mounted on curled wire 752, curled wire 752 passing through loops 636.

When anchoring device 600 is properly positioned in an orifice in which it is to be deployed, channel 500 is retracted allowing arms 620 to expand. Thereafter, rod 506 is rotated in a manner which releases arms 622 from curled wire 752. The rotation is optionally performed slowly and/or in steps, allowing a physician to carefully determine that a released arm 622 is properly positioned, before releasing another arm 622. When all of arms 622 have been released, rod 506 and channel 500 are removed together from the patient.

Rod 506 is optionally sufficiently stiff to allow proximal and distal movement relative to channel 500. Alternatively, rod 506 is only used for proximal movement relative to channel 500. On the other hand, rod 506 is optionally sufficiently flexible to allow its insertion percutaneously into inner organs of patients, such as the heart.

Curled wire 752 is optionally formed of a strong material, such as nitinol, stainless steel or titanium, which does not deform and change its shape under the pressure of arms 622

In some embodiments of the invention, all of arms 622 are of the same length. Alternatively, the arms have different lengths, according to their locations on curled wire 752. It is noted that other arrangements for gradually releasing arms 622 may be used in accordance with embodiments of the invention. For example, arms 622 may have different lengths such that gradual retraction of channel 500 causes separate release of the arms.

Any of the delivery tools used for the anchoring devices may include in addition to the elements required for the delivery, other tools and/or elements such as working channels, a protective sheath, one or more cameras and/or sensors. Thus, in addition to performing the delivery, the delivery tool may be used to diagnose the patient before or after the implant. For example, immediately before the anchoring device is released, a last minute diagnosis, for example by sensing pressure, blood flow and/or temperature may be performed to by the same delivery tool to determine that the implant procedure is safe. Alternatively or additionally, after the anchoring device is implanted, sensors on the delivery device determine whether there were problems in the implant and if problems were encountered, the anchoring device may be removed, for example as is now described with reference to FIG. 18. In some embodiments of the invention, when a closure device is implanted, a sensor on the delivery tool may determine whether the orifice sufficiently sealed the orifice.

Figure 18:
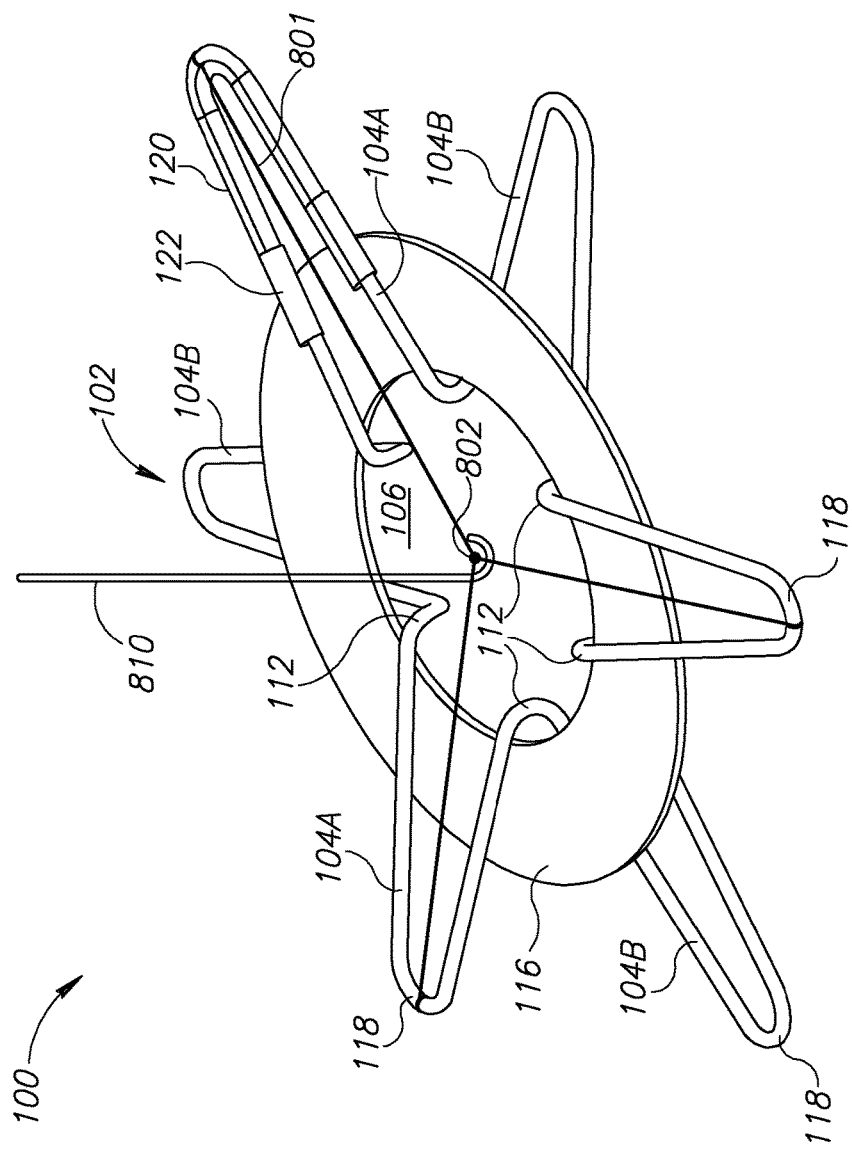
FIG. 18 is a schematic illustration of an anchoring device with a removal string, in accordance with an exemplary embodiment of the invention.

FIG. 18 is a schematic illustration of an anchor device 100 with a retrieval string 801, in accordance with an exemplary embodiment of the invention. A retrieval string 801 connects distal points 118 of petals 104A to a central junction 802. If necessary, a hook 810 is passed through a working channel of the delivery device, or is otherwise brought to central junction 802 and is pulled proximally so as to fold petals 104A and pull them back into channel 500. In some embodiments of the invention, in order to insert hook 810, rod 506 is removed from channel 500. Thereafter, channel 500 is advanced to push also distal petals 104B into channel 500 and remove anchor device 100 from the patient.

Alternatively or additionally, petals 104 are long enough to allow attachment of a patch to them from inside the heart, e.g., the right chamber, to aid in the removal.

Optionally, in embodiments in which an anchoring device carries a closure portion 198, retrieval string 801 is connected to closure portion 198. Optionally, in embodiments including flap 138, a same string is used for restricting movements of the flap (wire 149, FIG. 4A) and for retrieval.

In some embodiments of the invention, petals 104A are inclined toward central junction 802 in order to allow easier collapse.

Although anchor device 100 is described herein as being suitable for insertion in minimally invasive procedures, the anchor devices of the present invention may also be delivered in open surgery and in some embodiments of the invention, anchor devices not suitable for minimally invasive surgery are used.

CONCLUSION

It will be appreciated that the above-described methods may be varied in many ways, including, changing materials, sizes and shapes. For example, rather than folding device 100 in an organized manner, device 100 may be packaged by an irregular folding and/or by a collapsing of the device without any preplanned folding scheme. Furthermore, device 100 may have a structure which conforms to a wavy or other shaped tissue wall surface.

It should also be appreciated that the above described description of methods and apparatus are to be interpreted as including apparatus for carrying out the methods, and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Particularly, the delivery tools described for one anchoring device may be used for other anchoring devices. Also, the valves, closure devices and tubes described as being mounted on a specific anchoring device may be mounted on any of the other described anchoring devices and/or combination or variations thereof.

Variations of embodiments described will occur to persons of the art. Furthermore, the terms "comprise," "include," "have" and their conjugates, shall mean, when used in the claims, "including but not necessarily limited to".

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims.

The invention claimed is:

1. A medical implant, comprising:
    an anchor portion comprising a first plurality of arms adapted to engage a face of an atrial septum of a body and a second plurality of arms adapted to engage an opposing face of the atrial septum, wherein the anchor portion is configured such that at least one of the arms of the first plurality does not have an entirely overlapping arm in the second plurality on the opposing face of the atrial septum, and wherein the anchor portion does not penetrate the atrial septum; and
    an opening portion adapted to define an opening for blood flow through the atrial septum, when the anchor portion engages the atrial septum.

2. A medical implant according to claim 1, wherein the opening portion is adapted to radially expand in changing from a collapsed state to a deployed state.

3. A medical implant according to claim 1, wherein a largest end to end extent of the anchor portion in a deployed state is at least twice the largest end to end extent of the opening defined by the opening portion.

4. A medical implant according to claim 1, wherein the first and second pluralities of arms are formed of a super-elastic material.

5. A medical implant according to claim 1, wherein the opening portion comprises a ring surrounding the defined opening.

6. A medical implant according to claim 1, wherein the anchor portion and opening portion are configured to have a low profile of less than 3 millimeters in a deployed state not on a tissue wall.

7. A medical implant according to claim 1, wherein the first and second pluralities of arms comprise flexible elongate elements.

8. A medical implant according to claim 1, wherein the first and second pluralities of arms comprise petals.

9. A medical implant according to claim 1, wherein in the deployed state at least one of the arms of the first plurality of arms does not have a partially overlapping arm from the second plurality of arms.

10. A medical implant according to claim 1, wherein the first and second pluralities of arms are configured to surround the opening in a deployed state and wherein most of the arms in the first plurality of arms are neighbored along a line surrounding the opening by two arms in the second plurality of arms.

11. A medical implant according to claim 1, wherein most of the arms of the first plurality of arms do not have arms overlapping them in the second plurality of arms, in the deployed state.

12. A medical implant according to claim 1, wherein the anchor portion and the opening portion are comprised in a single element.

13. A medical implant according to claim 1, wherein the opening is configured to remain clear from elements mounted therein.

14. A medical implant according to claim 1, comprising a valve mounted on the anchor portion in a manner which regulates flow through an opening defined by the opening portion.

15. A medical implant according to claim 14, wherein the valve is formed together with the anchor portion from a same sheet, wire or tube.

16. A medical implant according to claim 14, wherein the valve is at least partially formed from a different material from the anchor portion.

17. A medical implant according to claim 14, comprising a sensor mounted on the anchor portion.

18. A medical implant according to claim 1, wherein portions of the implant are covered by ePTFE or polyurethane.

19. A medical implant according to claim 1, wherein the first and second pluralities of arms are arranged alternately around the opening, such that each arm of the first plurality of arms is neighbored by an arm of the second plurality of arms on one side and another arm of the second plurality of arms on the opposite side.

20. A medical implant according to claim 1, wherein the medical implant has a collapsed state and a deployed state and wherein the opening portion is adapted to apply a radial force when released from the collapsed state.

21. A medical implant according to claim 1, wherein at least one of the arms of the first or second plurality of arms comprises a wire with a curved shape.

22. A medical implant, comprising:
an anchor portion adapted to attach to an atrial septum of a body without penetrating the atrial septum, the anchor portion comprising a plurality of arms adapted to be located on opposite sides of the attachment to the atrial septum by including parts adapted to be located on opposite sides of the atrial septum; and
an opening portion adapted to define an opening for blood flow when deployed within the body, which opening has a length of less than 3 millimeters, in which blood passing through the opening comes in contact with the implant.

23. An implant according to claim 22, wherein the plurality of arms located on opposite sides of the attachment to the atrial septum do not entirely overlap with one another.

24. An implant according to claim 22, wherein the anchor portion comprises a plurality of elongate elements extending radially from the opening portion, wherein a first group of the elongate elements are adapted to be located on one side of the atrial septum and a second group of the elongate elements is adapted to be located on a second side of the atrial septum.

25. An implant according to claim 24, wherein each of the first and second groups comprises at least three elongate elements.

26. An implant according to claim 24, wherein at least some of the elongate elements comprise petal shaped elements.

27. An implant according to claim 24, wherein at least some of the elongate elements comprise hoof shaped elements.

28. An implant according to claim 22, wherein the anchor portion and opening portion are formed from a single piece.

29. An implant according to claim 22, wherein the anchor portion and opening portion are configured to have in a deployed state a low profile of less than 3 millimeters.

30. An implant according to claim 22, comprising a skirt surrounding the opening defined by the opening portion.

31. An implant according to claim 22, comprising a closure unit adapted to block blood flow through the opening.

32. An implant according to claim 31, wherein the closure unit is part of a valve which controls the extent of blood flow through the opening.

33. A medical implant, comprising:
an anchor portion adapted to attach to an atrial septum of a body without penetrating the atrial septum; and
an opening portion adapted to define an opening for blood flow when deployed within the body, which opening has a length of less than 3 millimeters, in which blood passing through the opening comes in contact with the implant,
wherein the opening portion is adapted to cover less than 20% of the perimeter of the opening it defines.

34. A medical implant, comprising:
an anchor portion adapted to attach to an atrial septum of a body without penetrating the atrial septum; and
an opening portion adapted to define an opening for blood flow when deployed within the body, which opening has a length of less than 3 millimeters, in which blood passing through the opening comes in contact with the implant,
wherein the anchor portion is configured to engage the atrial septum such that a length in which blood passing through the opening comes in contact with the implant is less than 1 millimeter thicker than the atrial septum.

35. A medical implant, comprising:
an anchor portion adapted to attach to an atrial septum of a body without penetrating the atrial septum; and
an opening portion adapted to define an opening for blood flow when deployed within the body, which opening has a length of less than 3 millimeters, in which blood passing through the opening comes in contact with the implant,
wherein the anchor portion and opening portion are configured to have a low profile of less than 15% of an end to end extent of the anchor portion in a deployed state.

36. A medical implant, comprising:
an anchor portion adapted to attach to an atrial septum of a body without penetrating the atrial septum; and
an opening portion adapted to define an opening for blood flow when deployed within the body, which opening has a length of less than 3 millimeters, in which blood passing through the opening comes in contact with the implant,
wherein in the deployed state, the implant does not include parts within the opening defined by the opening portion, beyond parts of the opening portion defining the opening.

37. A method for delivering the medical implant of claim 1, the method comprising:
creating an orifice in the atrial septum of the body via a transeptal puncture tool; and
deploying the medical implant within the orifice such that the anchor portion engages the atrial septum and the opening portion defines an opening for blood flow through the orifice of the atrial septum.

38. A method according to claim 37, wherein the transseptal puncture tool comprises a needle and a dilator catheter.

39. A method according to claim 37, wherein deploying the medical implant within the orifice comprises percutaneously deploying the medical implant such that the medical implant self-expands within the orifice and expands the orifice.

* * * * *